US010189856B2

(12) United States Patent
Hirth-Dietrich et al.

(10) Patent No.: US 10,189,856 B2
(45) Date of Patent: Jan. 29, 2019

(54) USE OF SGC STIMULATORS, SGC ACTIVATORS, ALONE AND COMBINATIONS WITH PDE5 INHIBITORS FOR THE TREATMENT OF SYSTEMIC SCLEROSIS (SSC)

(75) Inventors: Claudia Hirth-Dietrich, Wuppertal (DE); Peter Sandner, Wuppertal (DE); Johannes-Peter Stasch, Solingen (DE); Andreas Knorr, Erkrath (DE); Georges Von Degenfeld, Leverkusen (DE); Michael Hahn, Langenfeld (DE); Markus Follmann, Wülfrath (DE)

(73) Assignee: Adverio Pharma GMBH, Schönefeld (DE)

( * ) Notice: Subject to any disclaimer, the term of this patent is extended or adjusted under 35 U.S.C. 154(b) by 202 days.

(21) Appl. No.: 13/816,020

(22) PCT Filed: May 24, 2011

(86) PCT No.: PCT/EP2011/058433
§ 371 (c)(1),
(2), (4) Date: Jun. 4, 2013

(87) PCT Pub. No.: WO2011/147810
PCT Pub. Date: Dec. 1, 2011

(65) Prior Publication Data
US 2014/0038956 A1 Feb. 6, 2014

(30) Foreign Application Priority Data
May 26, 2010 (DE) .................. 10 2010 021 637
Jul. 22, 2010 (EP) ..................... 10170413

(51) Int. Cl.
*A61K 31/437* (2006.01)
*A61K 31/197* (2006.01)
*A61K 31/427* (2006.01)
*A61K 31/4439* (2006.01)
*A61K 31/506* (2006.01)
*A61K 31/519* (2006.01)
*A61K 31/5377* (2006.01)
*A61K 45/06* (2006.01)
*C07D 495/04* (2006.01)
*C07D 471/04* (2006.01)
*A61K 31/426* (2006.01)
*C07C 229/38* (2006.01)
*C07D 261/10* (2006.01)
*C07D 277/30* (2006.01)
*C07D 333/34* (2006.01)
*C07D 401/04* (2006.01)
*C07D 417/06* (2006.01)
*C07D 487/04* (2006.01)

(52) U.S. Cl.
CPC .......... *C07D 495/04* (2013.01); *A61K 31/197* (2013.01); *A61K 31/426* (2013.01); *A61K 31/427* (2013.01); *A61K 31/437* (2013.01);
*A61K 31/4439* (2013.01); *A61K 31/506* (2013.01); *A61K 31/519* (2013.01); *A61K 31/5377* (2013.01); *A61K 45/06* (2013.01); *C07C 229/38* (2013.01); *C07D 261/10* (2013.01); *C07D 277/30* (2013.01); *C07D 333/34* (2013.01); *C07D 401/04* (2013.01); *C07D 417/06* (2013.01); *C07D 471/04* (2013.01); *C07D 487/04* (2013.01)

(58) Field of Classification Search
CPC .. A61K 31/437; A61K 31/197; A61K 31/427; A61K 31/4439; A61K 31/506; A61K 31/519; A61K 31/5377; A61K 45/06
See application file for complete search history.

(56) References Cited

U.S. PATENT DOCUMENTS

| | | | |
|---|---|---|---|
| 5,380,945 A | 1/1995 | Murad et al. | |
| 6,180,656 B1 | 1/2001 | Furstner et al. | |
| 6,335,334 B1 | 1/2002 | Schnindler et al. | |
| 6,538,023 B1 | 3/2003 | Ohnishi | |
| 6,693,102 B2 | 2/2004 | Stasch et al. | |
| 6,743,798 B1 | 6/2004 | Straub et al. | |
| 6,833,364 B1 | 12/2004 | Straub et al. | |
| 6,864,287 B1 | 3/2005 | Alonso-Alija et al. | |
| 7,087,644 B1 | 8/2006 | Alonso-Alija et al. | |
| 7,173,037 B2 | 2/2007 | Alonso-Alija et al. | |
| 7,674,825 B2 | 3/2010 | Alonso-Alija et al. | |
| 7,705,043 B2 | 4/2010 | Alonso-Alija et al. | |
| 2002/0173514 A1 | 11/2002 | Stasch et al. | |
| 2004/0087591 A1 | 5/2004 | Garvey et al. | |

(Continued)

FOREIGN PATENT DOCUMENTS

| | | |
|---|---|---|
| WO | 2000/02851 | 1/2000 |
| WO | 03/063875 A1 | 8/2003 |

(Continued)

OTHER PUBLICATIONS

Gore et al. "Oral sildenafil for the treatment of Raynaud's phenomenon and digital ulcers secondary to systemic sclerosis" Ann Rheum Dis, 2005, vol. 64, pp. 1387.*
Tamby et al. "New insights into the pathogenesis of systemic sclerosis" Autoimmunity Reviews, 2003, vol. 2, issue 3, pp. 152-157 (Year: 2003).*

(Continued)

*Primary Examiner* — Kendra D Carter
(74) *Attorney, Agent, or Firm* — Ice Miller LLP

(57) ABSTRACT

The use of sGC stimulators, sGC activators alone, or in combination with PDE5 inhibitors for the prevention and treatment of fibrotic diseases, such as systemic sclerosis, scleroderma, and the concomitant fibrosis of internal organs.

Figure 1:
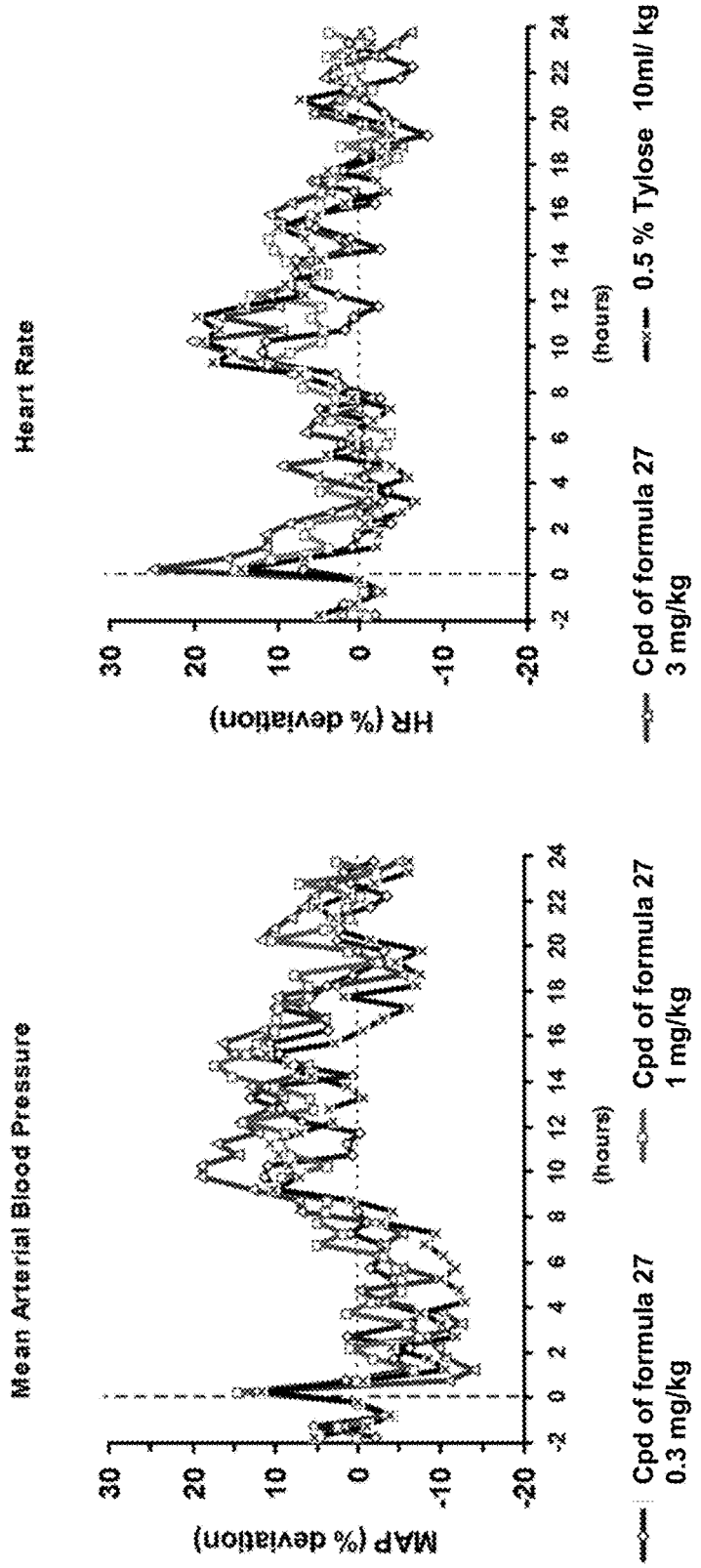
Figures 1, 1A:
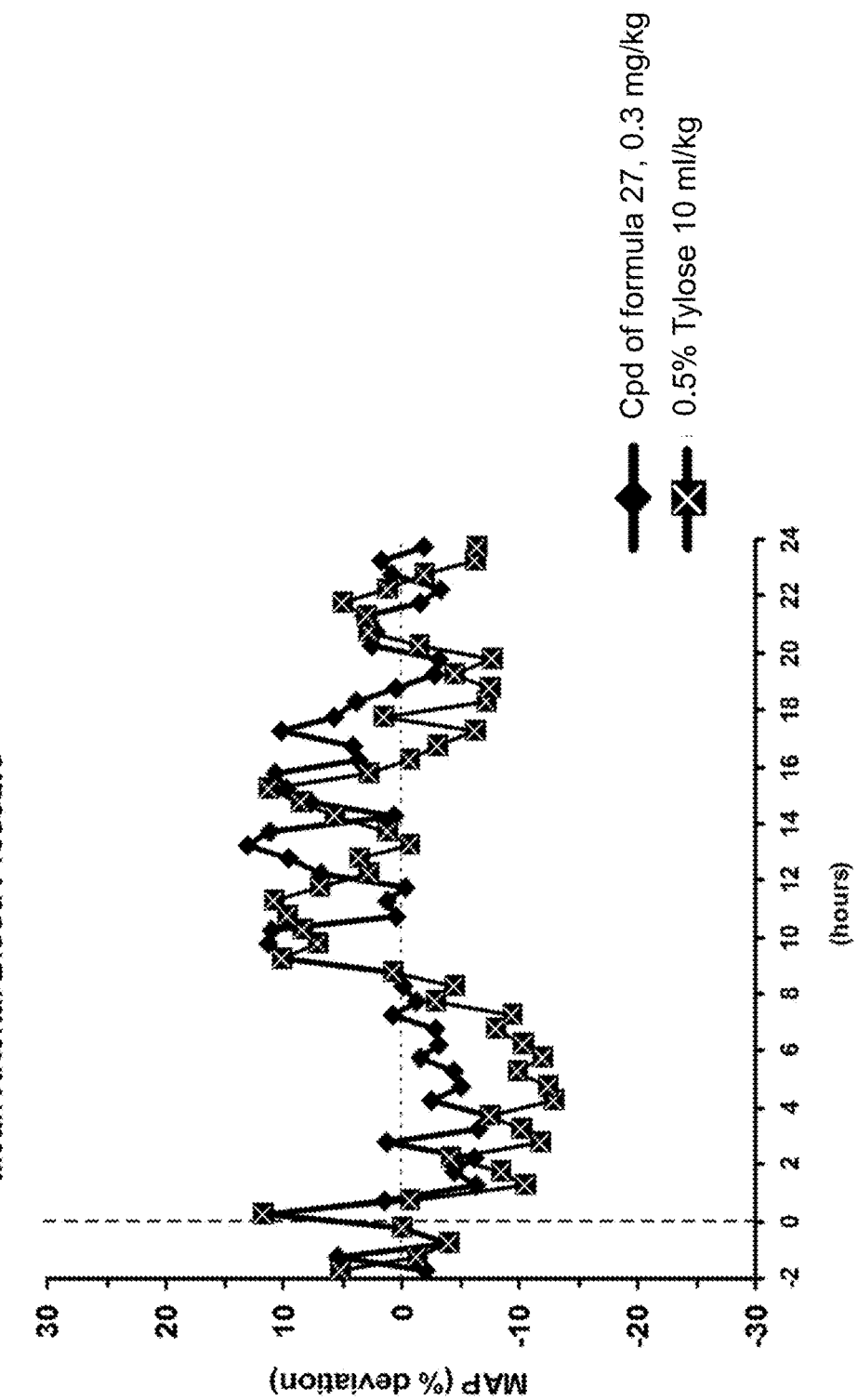

7 Claims, 35 Drawing Sheets
Specification includes a Sequence Listing.

(56) References Cited

U.S. PATENT DOCUMENTS

| | | | |
|---|---|---|---|
| 2004/0176446 | A1 | 9/2004 | Alonso-Alija et al. |
| 2004/0224945 | A1 | 11/2004 | Straub et al. |
| 2005/0267032 | A1 | 12/2005 | Fulp et al. |
| 2006/0052397 | A1 | 3/2006 | Alonso-Alija et al. |
| 2006/0094769 | A1 | 5/2006 | Alonso-Alija et al. |
| 2009/0209556 | A1 | 8/2009 | Bittner et al. |
| 2009/0215769 | A1* | 8/2009 | Krahn et al. ............... 514/234.2 |
| 2009/0221570 | A1 | 9/2009 | Haning et al. |
| 2009/0286782 | A1 | 11/2009 | Ibrahim et al. |
| 2010/0016305 | A1 | 1/2010 | Krahn et al. |
| 2010/0210643 | A1 | 8/2010 | Sandner et al. |
| 2011/0028493 | A1 | 2/2011 | Matsunaga et al. |
| 2011/0159474 | A1 | 6/2011 | Stasch et al. |
| 2011/0195992 | A1 | 8/2011 | Savory et al. |
| 2012/0022028 | A1 | 1/2012 | Sandner et al. |
| 2012/0116060 | A1 | 5/2012 | Bogdanova et al. |
| 2013/0053393 | A1* | 2/2013 | Frangakis et al. ....... 514/252.16 |
| 2013/0035340 | A1 | 7/2013 | Sandner et al. |
| 2014/0038956 | A1 | 2/2014 | Hirth-Dietrich et al. |

FOREIGN PATENT DOCUMENTS

| | | | |
|---|---|---|---|
| WO | 2007/009607 | A1 | 1/2007 |
| WO | 2008/138483 | A1 | 11/2008 |
| WO | 2008/148474 | A2 | 12/2008 |
| WO | 2009/068652 | | 6/2009 |
| WO | 2009/071504 | | 6/2009 |
| WO | 2010/065275 | | 6/2010 |
| WO | 2010/081647 | A2 | 7/2010 |
| WO | 2010/121973 | A1 | 10/2010 |

OTHER PUBLICATIONS

Raat et al., "Direct sGC Activation Bypasses NO Scavenging Reactions of Intravascular Free Oxy-Hemoglobin and Limits Vasoconstriction", Antioxidants and Redox Signaling, (2013) pp. 1-12, vol. 00, No. 00.

National Institute of Health, "The Management of Sickle Cell Disease" National Heart, Lung, and Blood Institute, Division of Blood Diseases and Resources, (1984) pp. 108-110.

Cokic et al., "Hydroxyurea nitrosylates and activates soluble guanylyl cyclase in human erythroid cells," Blood 2007, vol. 111, No. 3, 1117-1123.

Goldberg et al., "Stimulation of Human Platelet Guanylate Cyclase by Fatty Acids," J. Biol. Chem., 1977, 252, pp. 1279-1285.

Ko et al., "YC-1, a Novel Activator of Platelet Guanylate Cyclase;" Blood, 1994, 84: 4226-4233.

Hsu et al, "Hemolysis in sickle cell mice causes pylmonary hypertension due to global impairment in nigric oxide bioavailability," Blood, 2007, 198: 3088-3098.

Müsch et al., "Effect of YC-1, an NO-independent, Superoxide-Sensitive Stimulator of Soluble Gyanylyl Cyclase, on Smooth Muscle Responsiveness to Nitrovasodilators;" Brit. J. Pharm., 1997, 120, pp. 681-689.

Pettibone et al., "A Structurally Novel Stimulator of Guanylate Cyclase with Long-Lasting Hypotensive Activity in the Dog," Euro. J. of Pharmacology, 1985, 116, pp. 307-312.

Stasch et al., "Targeting the heme-oxidized nitric oxide receptor for selective vasodilation of diseased blood vessels," J. Clin. Invest. 2006, 116(9): 2552-2561.

Weiskopf et al., "Hemoglobin-Based Oxygen Carriers: Compassionate Use and Compassionate Clinical Trials," Anaesthesia & Analgesia, 2010, 110(3):659-662.

Yu et al., "Vasorelaxant Effect of Isoliquiritigenin, A Novel Soluble Guanylate Cyclase Activator, in Rat Aorta," Brit. J. of Pharmacology, 1995, 114, pp. 1587-1594.

Bayer Pharmaceuticals Corporation, LEVITRA® (vardenafil HCl) Tablets, 2007, pp. 1-30.

Evgenov et al., "NO-Independent Stimulators and Activators of Soluble Guanylate Cyclase: Discovery and Therapeutic Potential," Nature Reciews Drug Discovery, 2006, 5(9):755-768.

Ferrini et al., "Effects of long-term vardenafil treatment on the development of fibrotic plaques in a rat model of Peyronie's disease," BJU Int. 2006, 97:625-633.

Kaplan et al., "Phospodiesterase Type 5 Inhibitors for the Treatment of Male Lower Urinary Tract Symptoms," Rev. in Urology, 2007, 9(2):73-77.

Khanna et al., "Evidence-based management of rapidly progressing systemic sclerosis," Best. Pract. Res. Clin. Rheumatol. 2010, 24:387-400.

Knorr et al., Nitric Oxide-independent Activation of Soluble Guanylate Cyclase by BAY 60-2770 in Experimental Liver Fibrosis, Arzneimittel-Forschung (Drug Research), 2008, 58(2):71-80.

McVary et al., "Sildenafil Citrate Improves Erectile Function and Urinary Symptoms in Met with Erectile Dysfunction and Lower Urinary Tract Symptoms associated with Benign Prostatic Hyperplasia: a Randomized Double-Blind Trial," J. Urol. 2007, vol. 177, 1071-1077.

McVary et al., "Tadalfil Relieves Lower Urinary Tract Symptoms Secondary to Benign Prostatic Hyperplasia," J. Urol. 2007, vol. 177, 1401-1407.

Mittendorf et al., "Discovery of Riociguat (BAY 63-2521): A potent, Oral Stimulator of Soluble Guanylate Cyclase for the Treatment of Pulmonary Hypertension," Chem Med Chem 2009, 4: 853-865.

Nagayama, et al., "Sustained Soluble Guanylate Cyclase Stimulation Offsets Nitric-Oxide Synthase Inhibition to Restore Acute Cardiac Modulation by Sildenafil," J. of Pharmacology and Experimental Therapeutics, 2008, 326 (2):380-387.

Ong et al., "Innovative therapies for systemic sclerosis," Curr. Opinion in Rheumatol. 2010, 22:264-272.

Porst et al.,"Vardenafil in the Treatment of Lower Urinary Tract Symptoms Secondary to Benign Prostatic Hyperplasia," Current Urology Reports, 2008, 9:295-301.

Sandner et al., "Erectile Dysfunction and Lower Urinary Tract," Handbook Exper. Pharmacol. 2009, vol. 191:507-531.

Sandner et al.,"PDE5 Inhibitors Beyond Erectile Dysfunction," International Journal of Impotence Research, 2007, 19 (6):533-543.

Spiera et al., "Imatinib mesylate (Gleevec) in the treatment of diffuse cutaneous systemic sclerosis: results of a 1-year, phase IIa, single-arm, open-label clinical trial," Ann. Rheum. Dis. Epub Mar. 2011, 70:1003-1009.

Stasch et al., "NO- and haem-independent activation of soluble guanylyl cyclase: molecular basis and cardiovascular implications of a new pharmacalogical principal," British Journal of Pharmacology (2002), 136 (5), 773-783.

Stasch et al., "NO-Independent Regulatory Site on Soluble Guanylate Cyclase," Nature, 2001, 8:212-215.

U.S. Appl. No. 13/144,929, filed Sep. 29, 2011.
U.S. Appl. No. 13/577,135, filed Oct. 24, 2012.
U.S. Appl. No. 13/806,270, filed Feb. 28, 2013.

Beyer, C. et al., "Stimulation of soluble guanylate cyclase reduces experimental dermal fibrosis," Ann Rheum Dis (2012) 71: 1019-1026.

Beyer, C. et al., "Stimulation of the soluble guanylate cyclase (sGC) inhibits fibrosis by blocking non-canonical TGFβ signalling," Ann Rheum Dis (2015) 74: 1408-1416.

Dees, C. et al., "Stimulators of soluble guanylate cyclase (sGC) inhibit experimental skin fibrosis of different aetiologies," Ann Rheum Dis (2015) 74:1621-1625.

Zenzmaier, C. et al., "Activators and stimulators of soluble guanylate cyclase counteract myofibroblast differentiation of prostatic and dermal stromal cells," Experimental Cell Research (2015) 338: 162-169.

* cited by examiner

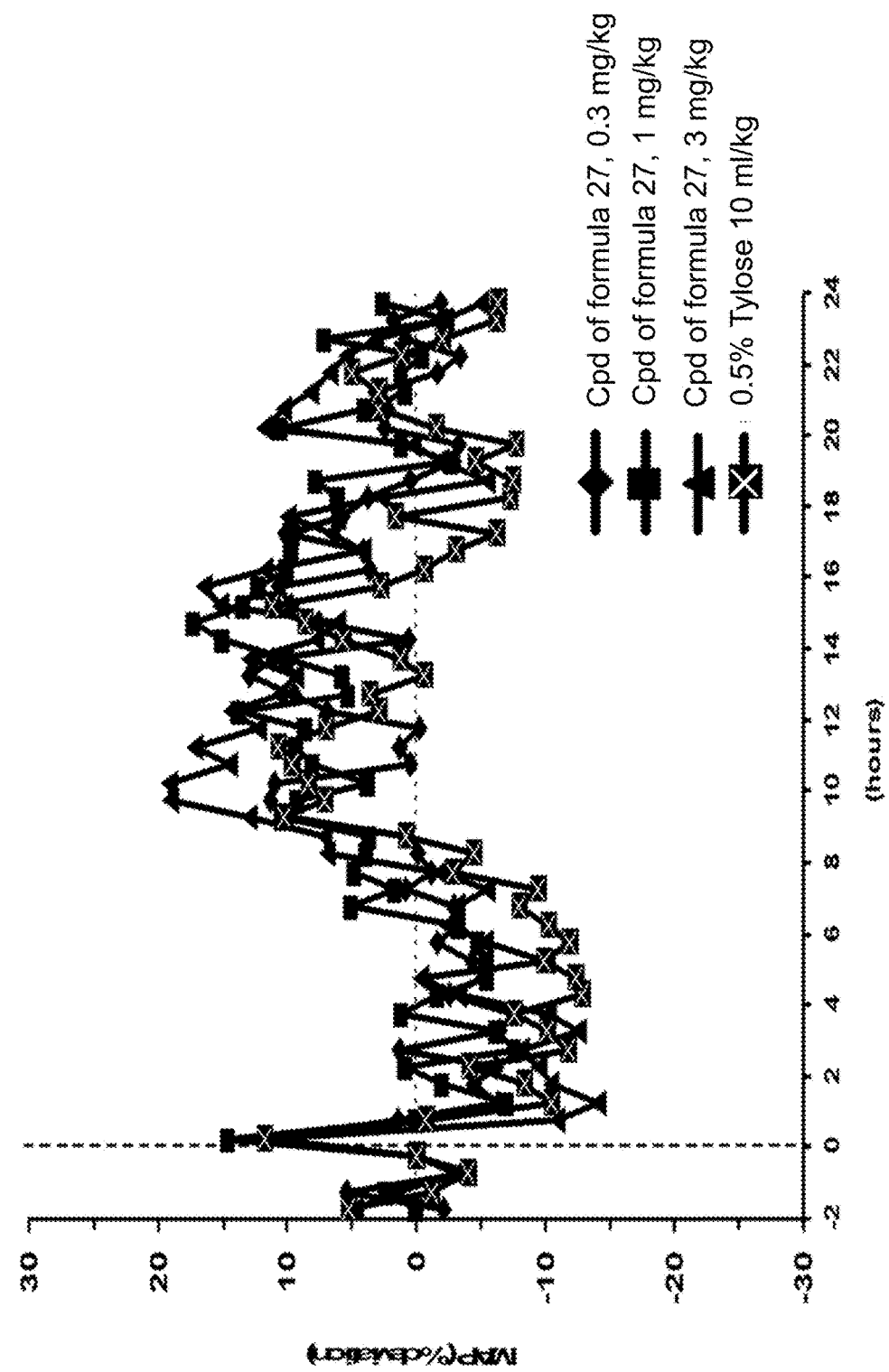

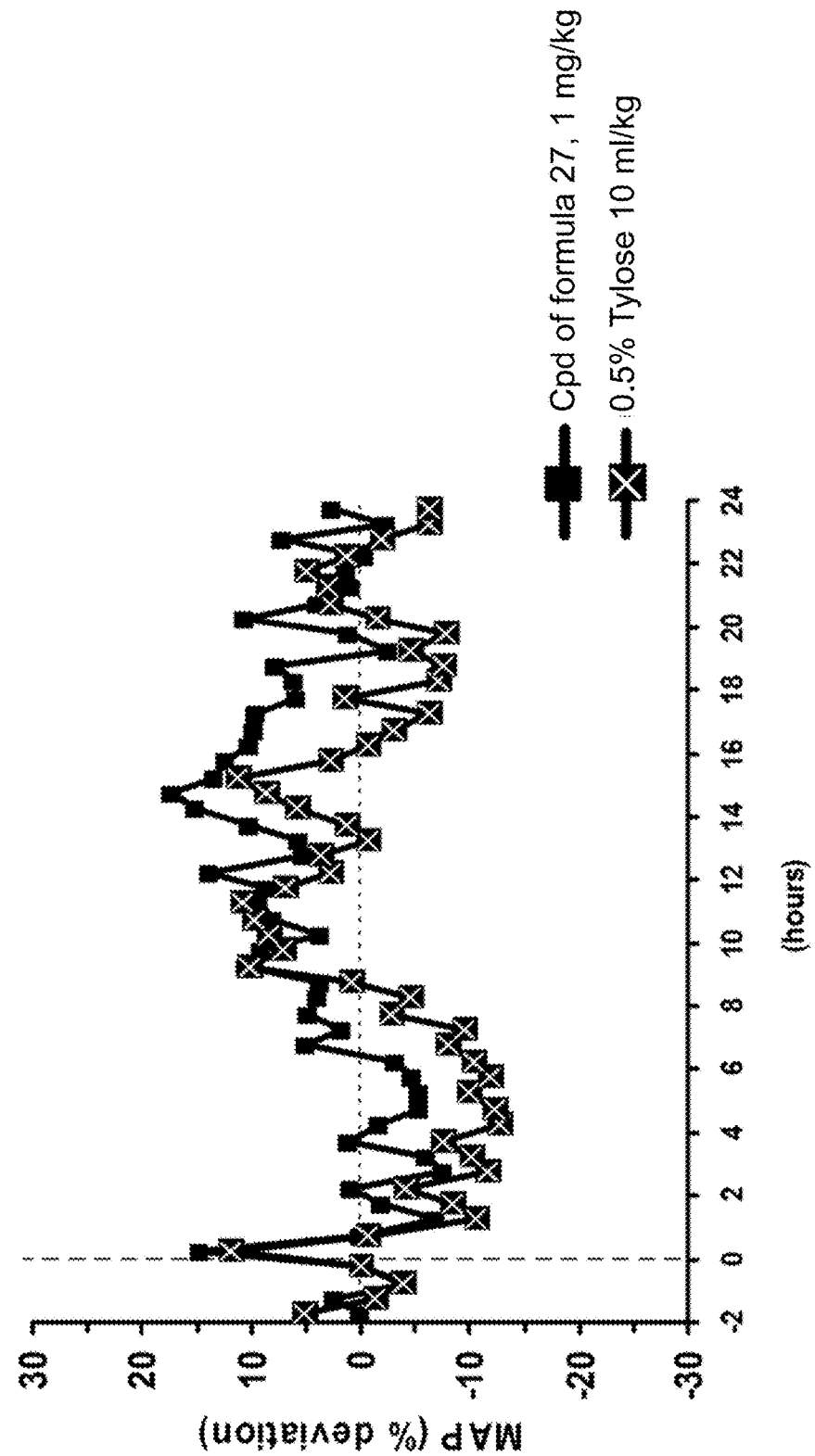

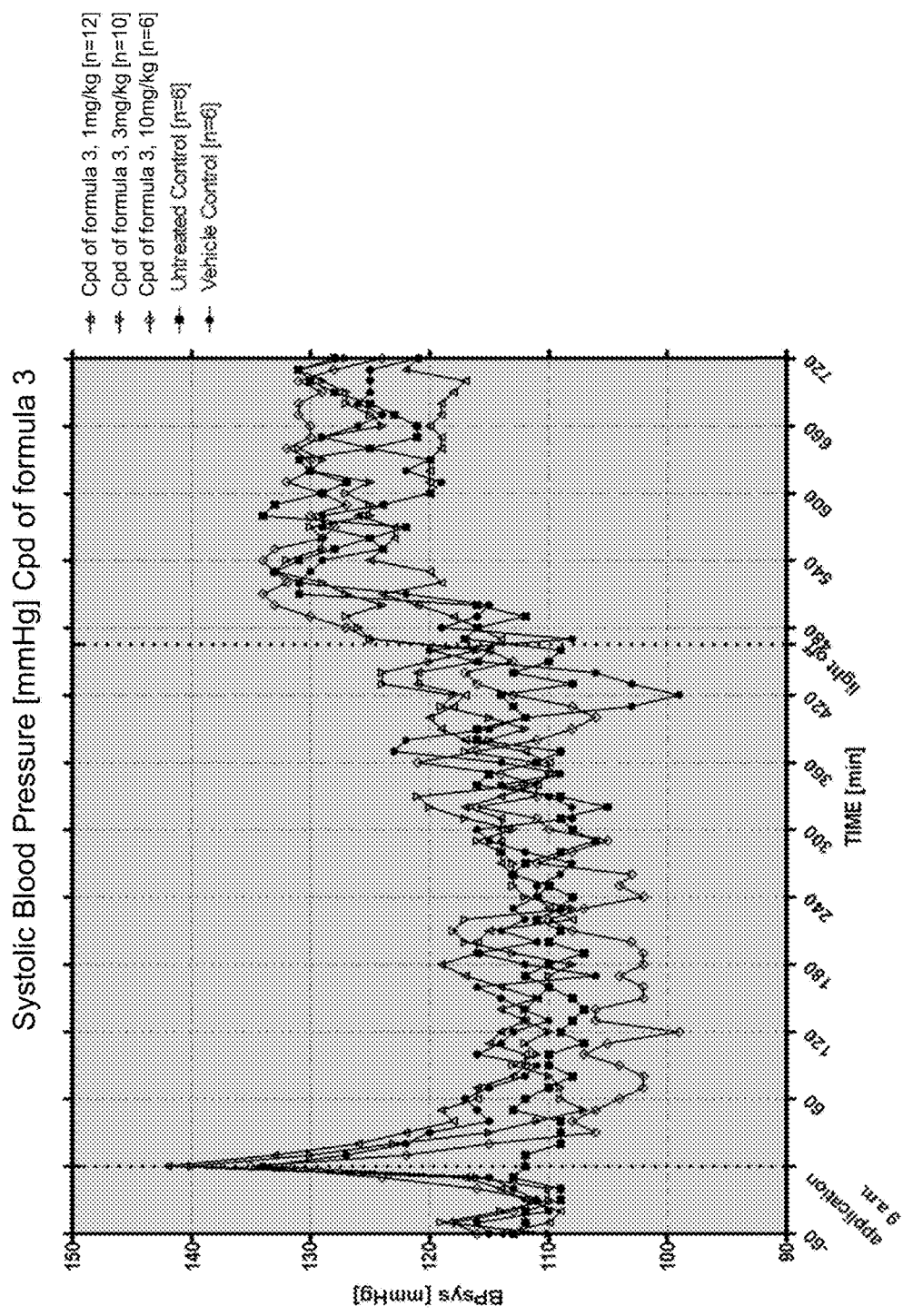

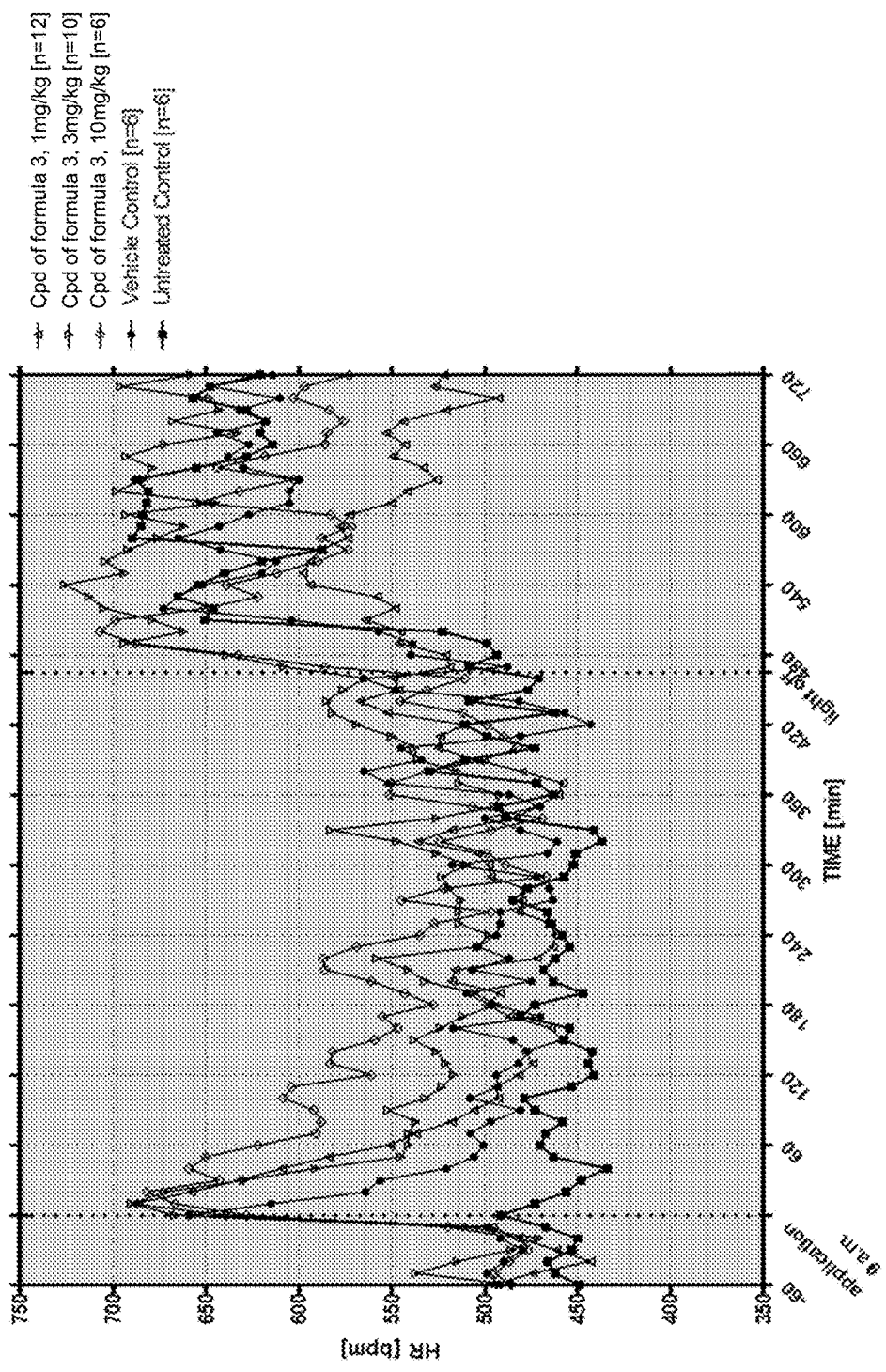

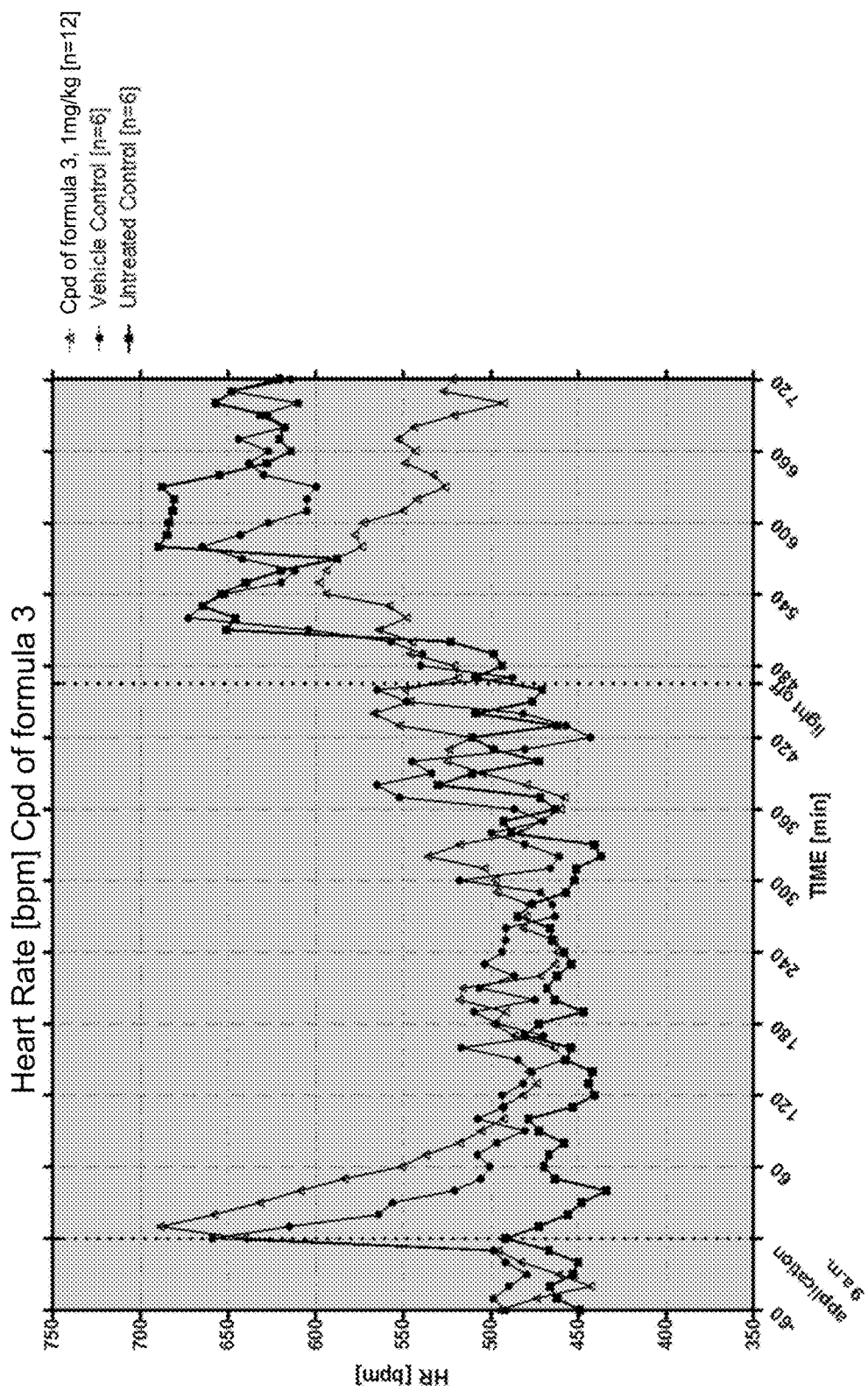

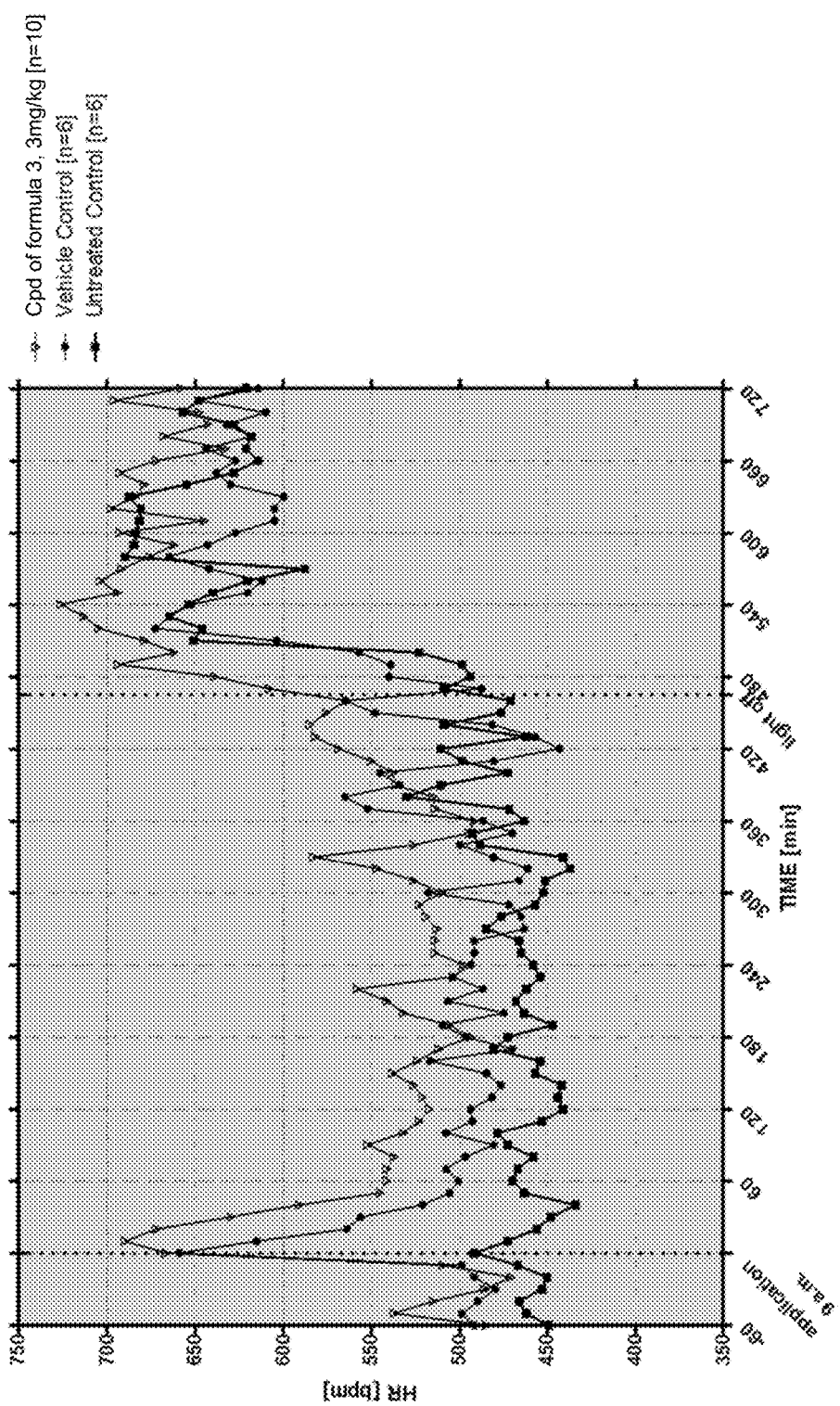

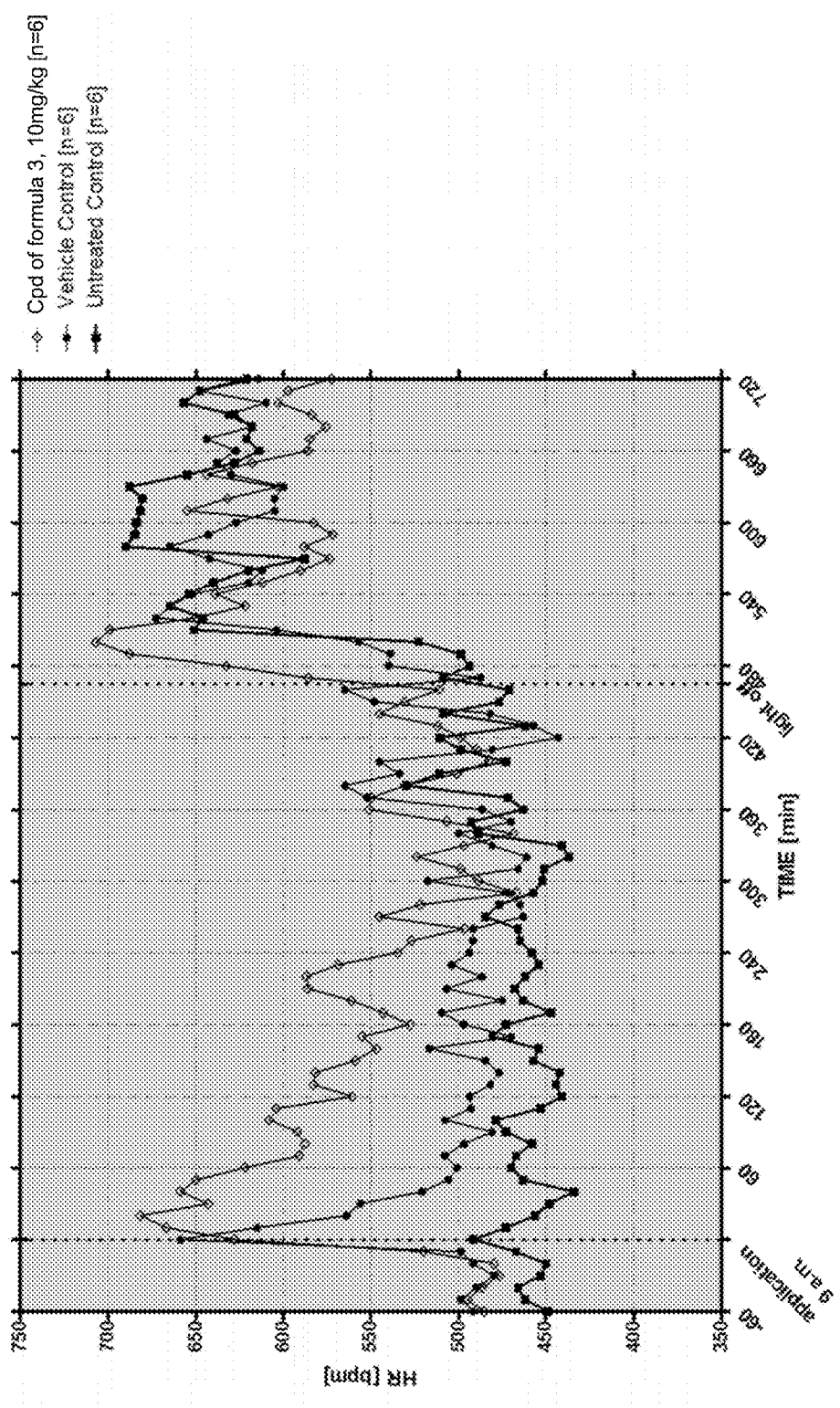

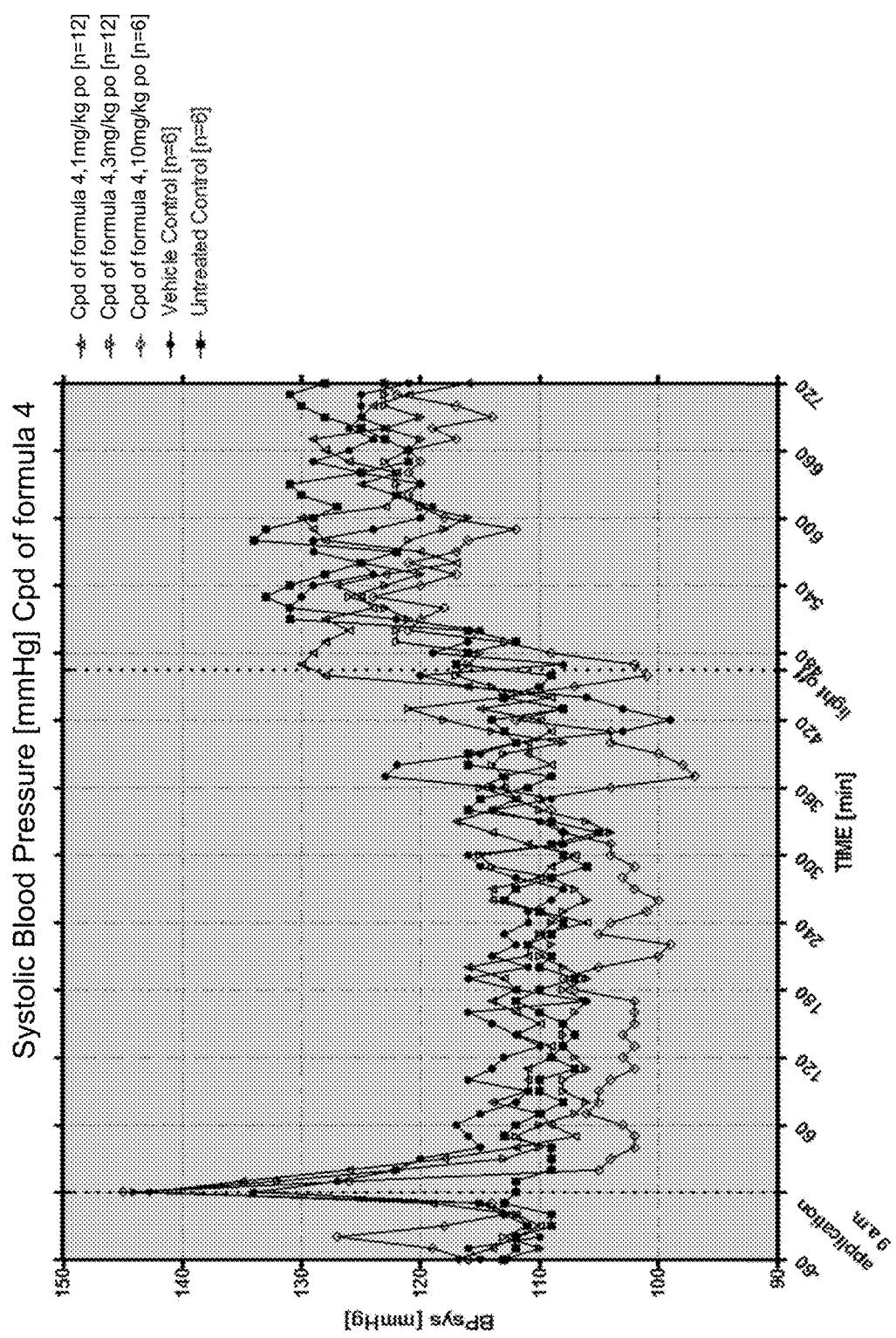

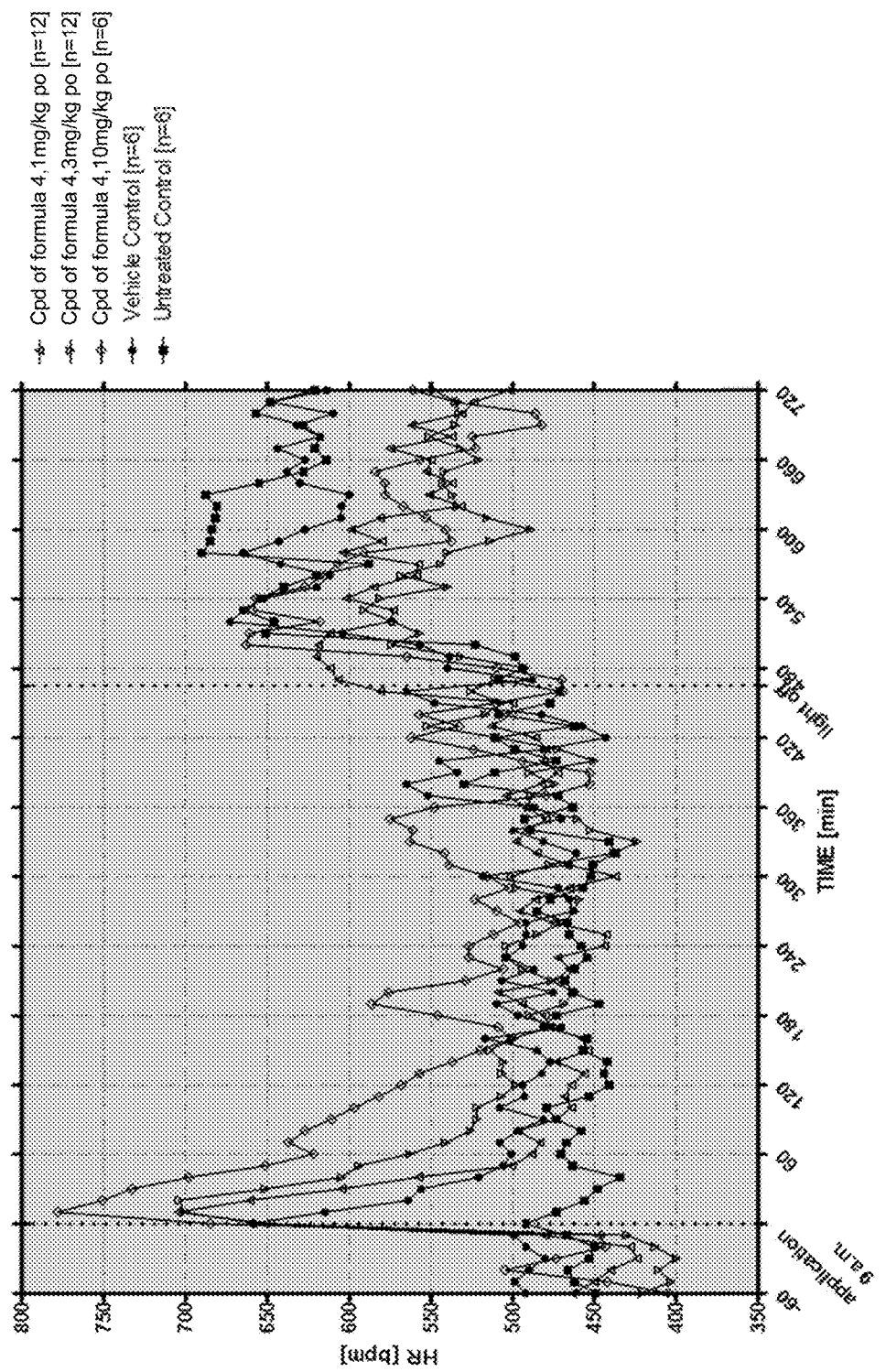

Heart Rate [bpm] Cpd of formula 4

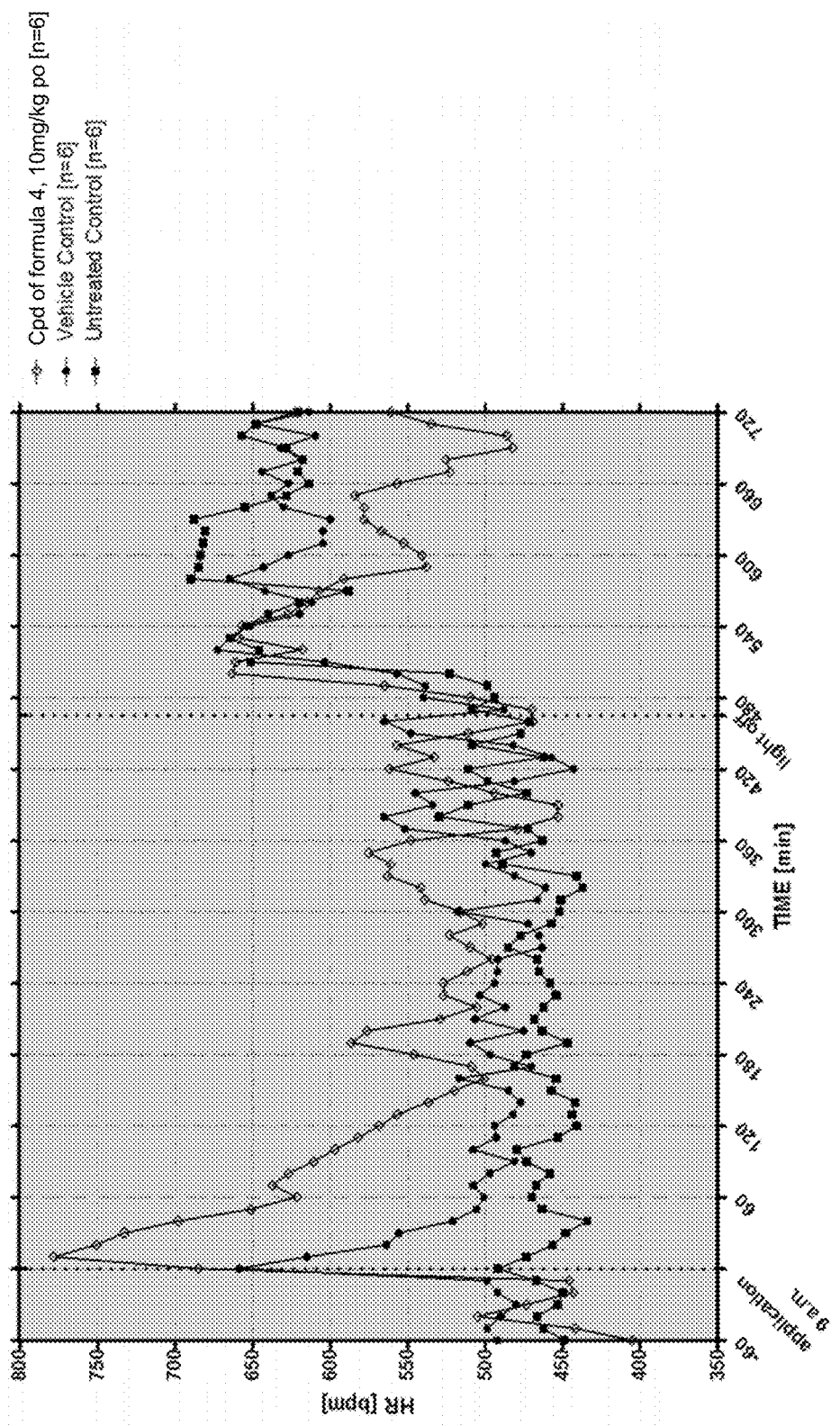

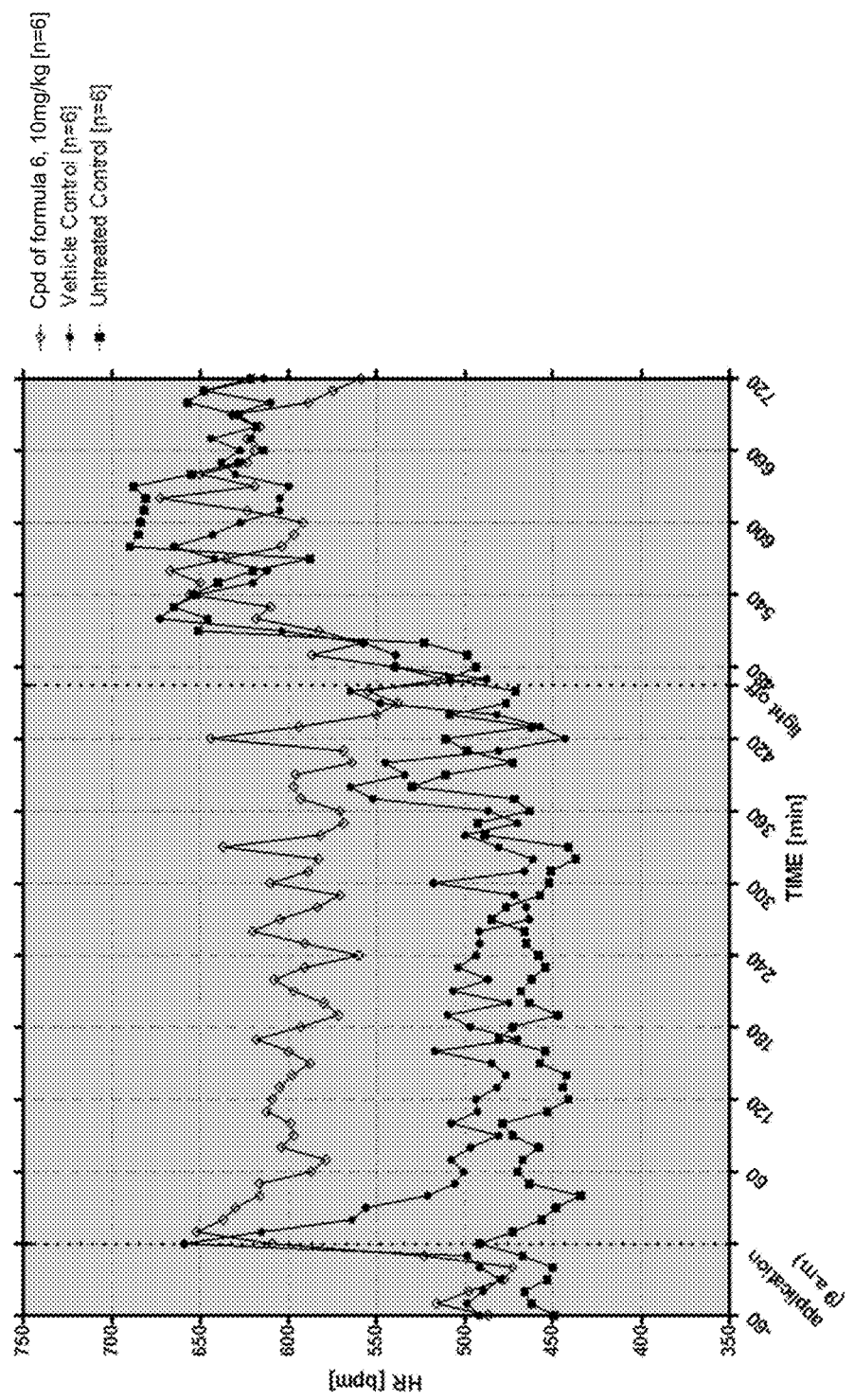

USE OF SGC STIMULATORS, SGC ACTIVATORS, ALONE AND COMBINATIONS WITH PDE5 INHIBITORS FOR THE TREATMENT OF SYSTEMIC SCLEROSIS (SSC)

The use of sGC stimulators, sGC activators alone, or in combination with PDE5 inhibitors for the prevention and treatment of fibrotic diseases, such as systemic sclerosis, scleroderma, and the concomitant fibrosis of internal organs.

BACKGROUND OF THE INVENTION

Systemic Sclerosis

The pathogenesis of Systemic Sclerosis (SSc) is still unclear and remains elusive. However, scleroderma is a non-inherited, noninfectious disease and thought to be an autoimmune disease. SSc has a broad variety of symptoms triggered by excessive deposition of extracellular matrix in the dermis resulting in skin fibrosis. In later stages SSc is characterized by progressive tissue fibrosis affecting other internal organs as the gut, the lung or the kidneys. Therefore scleroderma is the hallmark of the disease comprising also e.g. lung fibrosis, renal fibrosis, fibrosis of the heart, the gut or the blood vessels. It is suggested that inflammation, autoimmune disorders or vascular damage activates fibroblasts. Fibroproliferation is accompanied by excessive extracellular matrix production, dominated by Collagen type I resulting in progressive tissue fibrosis which can cause end organ failure and lead to high morbidity and mortality in patients with end-stage SSc (Harris et al. 2005—Kelley's Textbook of Rhematology $7^{th}$ edition. Elsevier Saunders, Philadelphia Pa.).

There is still no causative treatment for Systemic Sclerosis (SSc) available and the current therapy is based on suppression of the immune system via corticosteroids, cyclophosphamide, methotrexate. More recently kinase inhibitors are under investigation as immunosuppressant and antifibrotic agents in SSc, but tolerability is limited in SSc patients (Khanna and Denton 2010—Best. Pract. Res. Clin. Rheumatol. 24:387-400, Ong and Denton 2010—Curr. Opin. Rheumatol. 22:264-272, Spiera 2011—Ann. Rheum. Dis. Epub March 2011). These therapies either used as stand alone treatment or combined are of limited efficacy and exhibited considerable side effects. Therefore alternative treatment options in SSc which are efficacious and safe are urgently needed.

Antifibrotic Effects of cGMP:

The cyclic nucleotides, cyclic adenosine monophosphate (cAMP) and cyclic guanosine monophosphate (cGMP), were discovered decades ago and represent one of the most important second messenger pathway within cells. It is well established that the regulation of intra-cellular cGMP pools have substantial impact on physiology, and pathophysiology and is one basic principle of pharmacological intervention (Evgenov et al. 2006—Nat. Rev. Drug. Discov. 5(9):755-768). Besides the treatment of cardiovascular, lung or CNS-disorders there is ample evidence that an increase in cGMP is a very effective treatment option for urological disorders as well (Sandner et al. 2009—Handbook Exper. Pharmacol. 191:507-531). PDE5 inhibitors are the gold-standard for the treatment of erectile dysfunction (ED) but it was shown that PDE5 inhibitors could be useful for the treatment of symptomatic BPH which is characterized by Overactive Bladder (OAB) and Lower Urinary Tract Symptoms (LUTS) (Porst et al. 2008—Curr. Urol. Rep. 9:295-301; McVary et al. 2007—J. Urol. 177:1071-1077, J Urol. 177:1401-1407, Kaplan and Gonzalez. 2007—Rev. Urol. 9:73-77). The antifibrotic effects of Vardenafil, sGC stimulators and sGC activators is not understood yet. There are some descriptions about antifibrotic effects of Nitric-Oxide which are presumably mediated by cGMP in other organs and PDE5 inhibitors or guanylate cyclase stimulators have shown efficacy in penile fibrosis (Peyronie's disease) (Ferrini et al. 2006—B. J. Urol. 97:625-633) and liver fibrosis (Knorr et al. 2008—Arzneimittelforschung 58:71-80) respectively.

It is not known if the NO/cGMP system is involved in SSc and if cGMP increase provides a treatment option for this disease. We hypothetized that—independent from endogenous NO/cGMP production—sGC stimulators and activators might be an effective treatment option for Systemic Sclerosis (SSc).

We therefore investigated sGC stimulators and sGC activators, i.e. the compound of formula 27 according to compound of the formula

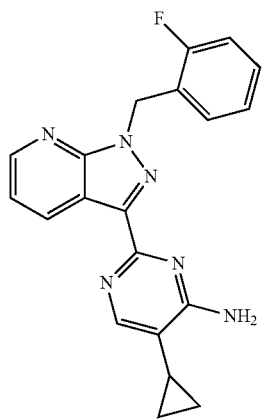

(27)

and combinations with PDE5 inhibitors thereof in vitro and in vivo in animal models for SSc. The in vivo experiments are including studies in bleomycin-induced skin and lung fibrosis in mice and studies on skin fibrosis in TSK-mice. In addition, the dose range tested on antifibrotic potential was also analyzed in mice with telemetric implants for blood-pressure and heart rate analysis.

We found in vivo in our animal models that:
sGC stimulators or sGC activators, i.e. the compound of formula 27, the compound of formula 3, the compound of formula 6, significantly reduced dermal thickness, hydroxyproline content of the skin and the number of dermal myofibroblasts in bleomycin-induced SSc in mice when administered in a preventive dose-regimen. (Example A: Table 1, Table 2). These data suggest an antifibrotic effect in Systemic Sclerosis when these compounds are given preventively.

sGC stimulators or sGC activators, i.e. the compound of formula 27 significantly reduced dermal thickness, hydroxyproline content of the skin and the number of dermal myofibroblasts in bleomycin-induced SSc in mice when administered in a therapeutic dose-regimen after established fibrosis. (Example B: Table 3). These data suggest an antifibrotic effect and regression of established fibrosis in Systemic Sclerosis when the compounds are given therapeutically.

sGC stimulators or sGC activators, i.e. the compound of formula 27 significantly reduced dermal thickness, hydroxyproline content of the skin and the number of dermal myofibroblasts in TSK mice. Since TSK mice already exhibited established fibrosis before start of the treatment the compound of formula 27 caused fibrosis-regression (Example C: Table 4). These data suggest an antifibrotic effect and regression of established fibrosis in Systemic Sclerosis when the compounds are given therapeutically.

sGC stimulators of sGC activators, i.e. the compound of formula 27, the compound of formula 3, the compound of formula 4, the compound of formula 6 were investigated in conscious mice with telemetric implants and blood pressure and heart rate was monitored (Example D). The compound of formula 27, the compound of formula 3, the compound of formula 4, the compound of formula 7 did not or only moderately, change the heamodynamic profile of the mice in dosages with antifibrotic properties (Example D: FIGS. 1, 2A, 2B, 3A, 3B, 4A, 4B). These data suggest a direct antifibrotic mode of action of sGC stimulators and sGC activators independent of blood pressure reduction by these compounds.

sGC stimulators or sGC activators, i.e. the compound of formula 27, alone and in combination with PDE5 inhibitors (i.e. Vardenafil) blocked TGF-induced collagen gene expression in vitro in human dermal fibroblasts (Example E). These data suggest a direct antifibrotic effect on the level of collagen production Thus, we found completely unexpected and for the first time that sGC stimulators or sGC activators i.e. the compound of formula 27, prevent fibrosis and regress established fibrosis in different animal models of inflammatory and non-inflammatory SSc including bleomycin-induced fibrosis models and the TSK-mouse model.

In addition there was no significant effect seen on systemic blood pressure which for the first time shows that these sGC stimulators have direct antifibrotic properties in SSc independent from blood pressure reduction.

Moreover sGC stimulators and sGC activators could block TGF-beta induce collagen synthesis implying a broad antifibrotic effect in other fibrotic disorders beyond SSc.

Taken together this data indicate for the first time that sGC stimulators and sGC activators, i.e. the compound of formula 27, the compound of formula 3, the compound of formula 4, the compound of formula 6 could represent a future treatment option for SSc.

DISCLOSURE OF THE INVENTION

Fibrotic disorders addressed by therapeutic agents of the invention which in particular and with substantial advantage can be treated by the above mentioned sGC stimulators or sGC activators alone or in combination with PDE5 inhibitors comprise but are not limited to Systemic Sclerosis (SSc), Systemic Sclerosis (SSc) concomitant fibrosis and fibrotic diseases.

Systemic Sclerosis (SSc) refers to but is not limited to diffuse Systemic Sclerosis (dSSc), limited Systemic Sclerosis (lSSc), overlap type of Systemic Sclerosis, undifferentiated type of Systemic Sclerosis, Systemic Sclerosis sine scleroderma, skin fibrosis, scleroderma, nephrogenic fibrosing dermopathy (NFD), nephrogenic systemic fibrosis (NSF), keloid formation.

SSc concomitant fibrosis refers to fibrosis of internal organs, comprising but not limited to the gut, the lung, the kidney and the blood vessels.

Fibrotic diseases comprises but are not limited to a condition in which collagen excess—independent of the etiology i.e. autoimmune disorders, radiation therapy, intoxications, diabetes, surgery—lead to fibrosis of the skin, gut, liver, lung, heart, bladder, prostate, blood vessels or any other localized or generalized fibrotic condition in tissues.

A preferred embodiment of the invention is compounds according to formulae (1)-(27) for the prevention and treatment of fibrotic diseases, such as systemic sclerosis, scleroderma, and the concomitant fibrosis of internal organs, as shown below:

2-[1-(2-Fluorbenzyl)-1H-pyrazolo[3,4-b]pyridine-3-yl]-5-(4-morpholinyl)-4,6-pyrimidine-diamine (1), disclosed as example 16 in WO 00/06569, 2-[1-(2-Fluorobenzyl)-1H-pyrazolo[3,4-b]pyridine-3-yl]-5-(4-pyridinyl)-4-pyrimidineamine (2), disclosed as example 1 in WO 02/42301, Methyl-4,6-diamino-2-[1-(2-fluorobenzyl)-1H-pyrazolo[3,4-b]pyridine-3-yl]-5-pyrimidinyl-(methyl)carbamate (3), disclosed as example 8 in WO 03/095451, Methyl-4,6-diamino-2-[1-(2-fluorobenzyl)-1H-pyrazolo[3,4-b]pyridine-3-yl]-5-pyrimidinyl-carbamate (4), disclosed as example 5 in WO 03/095451

4-({(4-carboxybutyl)[2-(2-{[4-(2-phenylethyl)benzyl]oxy}phenyl)ethyl]amino}methyl) carboxylic acid (5), disclosed as example 8a in WO 01/019780, Methyl-{4,6-diamino-2-[5-fluoro-1-(2-fluorobenzyl)-1H-pyrazolo[3,4-b]pyridine-3-yl]pyrimidine-5-yl}carbamate (6), Methyl-{4,6-diamino-2-[5-fluoro-1-(2-fluorobenzyl)-1H-pyrazolo[3,4-b]pyridine-3-yl]pyrimidine-5-yl}methylcarbamate (7), Methyl-{4,6-diamino-2-[5-fluoro-1-(2-fluorobenzyl)-1H-pyrazolo[3,4-b]pyridine-3-yl]pyrimidine-5-yl}(2,2,2-trifluoroethyl)carbamate (8), 5-Chloro-2-(5-chlorothiophene-2-sulfonylamino-N-(4-(morpholine-4-sulfonyl)-phenyl)-benzamide as sodium salt (9), disclosed in WO00/02851, 2-(4-Chloro-phenylsulfonylamino)-4,5-dimethoxy-N-(4-(thiomorpholine-4-sulfonyl)-phenyl)-benzamide (10), disclosed in WO00/02851, 1-{6-[5-Chloro-2-({4-trans-4-}trifluoromethyl)cyclohexyl]benzyl}oxy)phenyl]pyridine-2-yl}-5-(trifluoromethyl)-1H-pyrazol-4-carboxylic acid (11), disclosed in WO 2009/032249, 1-[6-(2-(2-Methyl-4-(4-trifluoromethoxyphenyl)benzyloxy)-phenyl)pyridine-2-yl]-5-trifluoromethyl-pyrazol-4-carboxylic acid (12), disclosed in WO 2009/071504, 1[6-(3,4-dichlorophenyl)-2-pyridinyl-5-(trifluoromethyl)-1H-pyrazole-4-caboxylic acid (13), disclosed in WO 2009/068652, 1-({2-[3-Chlor-5-(trifluoromethyl)phenyl]-5-methyl-1,3-thiazole-4-yl}methyl)-1H-pyrazole-4-carboxylic acid (14), 4-({2-[3-(Trifluoromethyl)phenyl]-1,3-thiazole-4-yl}methyl)benzoic acid (15) and 1-({2-[2-Fluoro-3-(trifluoromethyl)phenyl]-5-methyl-1,3-thiazole-4-yl}methyl)-1H-pyrazole-4-carboxylic acid (16) disclosed in WO 2009/123316, 4-Amino-2-[5-chloro-3(3,3,3-trifluoropropyl)-1H-indazol-1yl]-5,5-dimethyl-5,7-dihydro-6H-pyrrolo[2,3-d]pyrimidine-6-one (17), 4-Amino-2[5-chloro-3-(2,3,6-trifluorbenzyle)-1H-indazol-1yl]-5,5-dimethyl-5,7-dihydro-6H-pyrrolo[2,3-d]pyrimidine-6-one (18), 4-Amino-5,5-dimethyl-2-[3-(2,3,6-trifluorbenzyle) 1H-thieno[3,4-c]pyrazol-1-yl]-5,7-dihydro-6H-pyrrolo[2,3-d]pyrimidine-6-one (19), 4-Amino-5,5-dimethyl-2-[3-(2,3,6-trifluorbenzyle)-1H-thieno[2,3-d]pyrazole-1-yl]-5,5- dimethyl-5,7-dihydro-6H-pyrrolo[2,3-d]pyrimidine-6-one (20), 4-Amino-5,5-dimethyl-2-[7-(2,3,6-trifluorbenzyle)imidazo[1,5-b]pyridazine-5-yl]-5,7-dihydro-6H-pyrrolo[2,3-d]pyrimidine-6-one (21), 4-Amino-2-[6-chloro-3-(2,3,6-trifluorbenzyle)imidazo[1,5-a]pyridine-1-yl]]-5,5-dimethyl-5,7-dihydro-6H-pyrrolo[2,3-d]pyrimidine-6-one (22), 4-Amino-2-[6-fluoro-3-(2,3,6-trifluorbenzyle)imidazo[1,5-a]pyridine-1-yl]]-5,5-dimethyl-5,7-dihydro-6H-pyrrolo[2,3-d]pyrimidine-6-one (23), 4-Amino-2-[6-fluoro-3-(2,3,6-trifluorobenzyl) 6-fluoroimidazo[1,5-a]pyridine-1-yl]-5,5-dimethyl-5,7-dihydro-6H-pyrrolo[2,3-d]pyrimidine-6-one (24), 4-Amino-5,5-dimethyl-2-[3-(2,4,6-trifluorbenzyle)imidazo[1,5-a]pyridine-1-yl]]-5,7-dihydro-6H-pyrrolo[2,3-d]pyrimidine-6-one (25), 4-Amino-2-[3-(2-cyclopentylethyl)imidazo[1,5-a]pyridine-1-yl]-5,5-dimethyl-5,7-dihydro-6H-pyrrolo[2,3-d]pyrimidine-6-one (26), disclosed in WO 2010/065275, 3-(4-Amino-5-cyclopropylpyrimidin-2-yl)-1-(2-fluorobenzyl)-1H-pyrazolo[3,4-b]pyridine (27) known as BAY 41-2272 disclosed as example 1 in WO 00/06568.

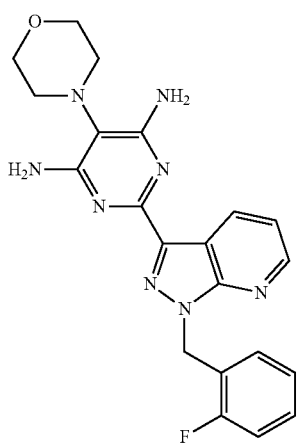
(1)

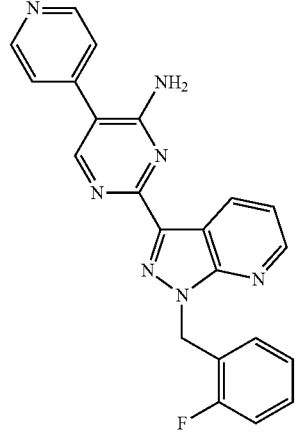
(2)

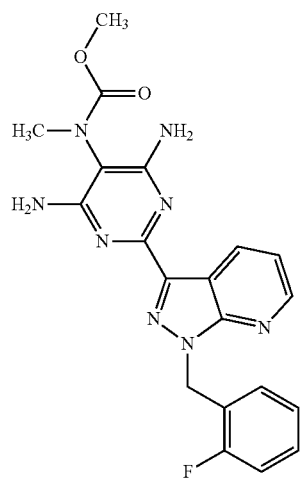
(3)

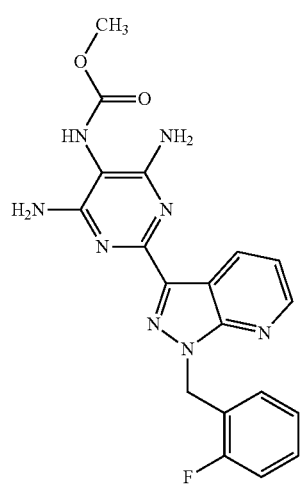
(4)

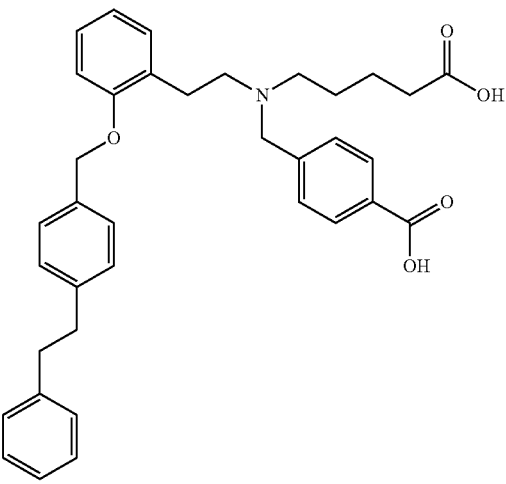
(5)

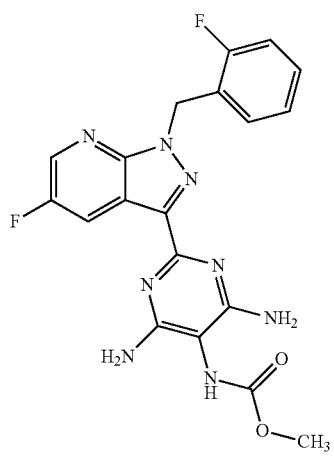
(6)
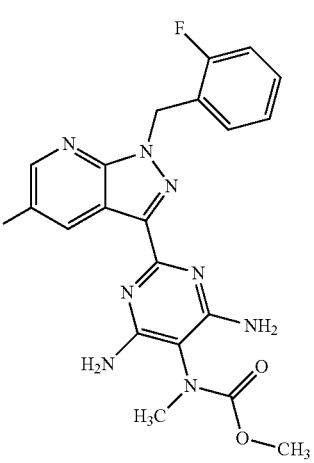
(7)
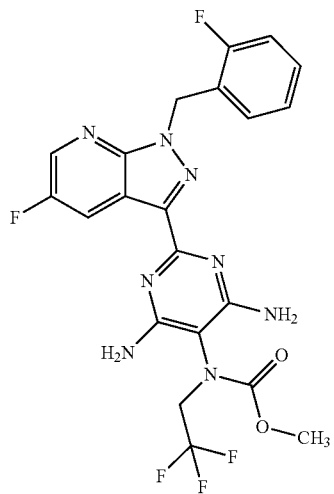
(8)
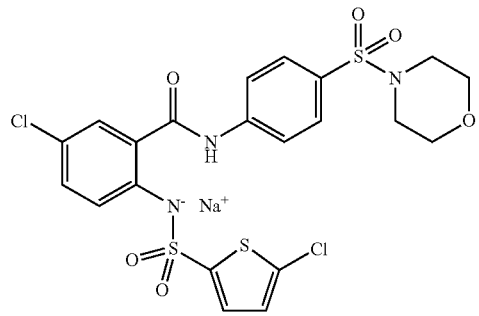
(9)
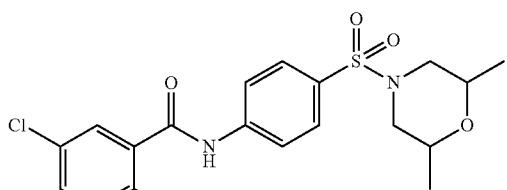
(10)
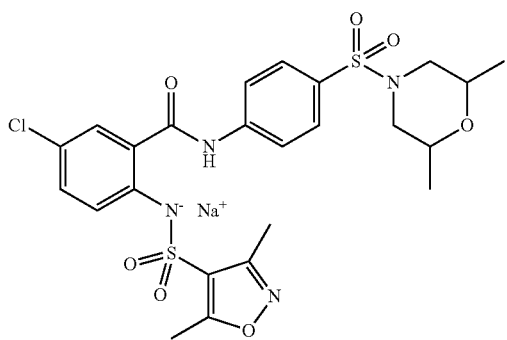
(11)
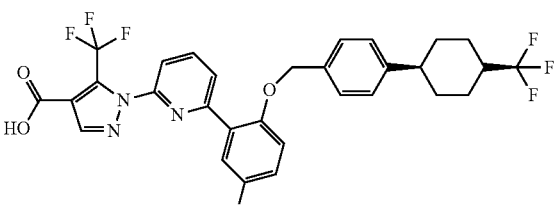
(12)
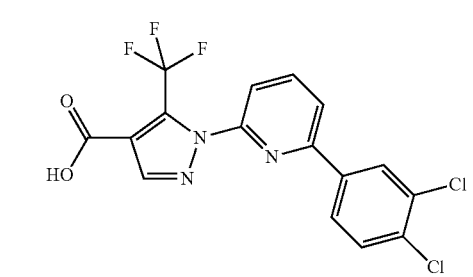
(13)
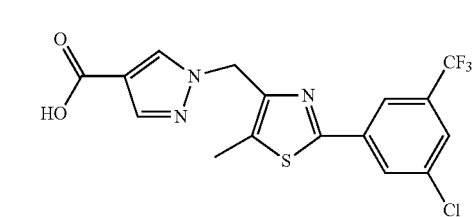
(14)

(15)
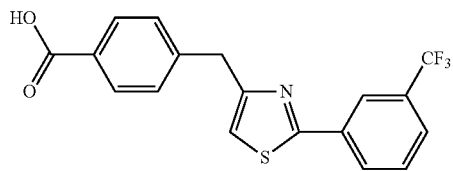
(16)
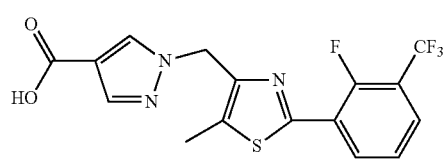
(17)
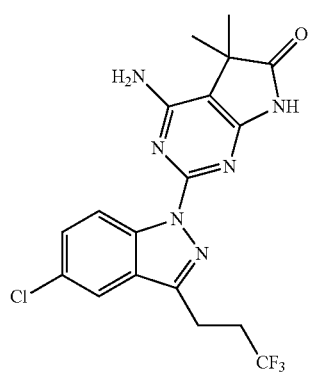
(18)
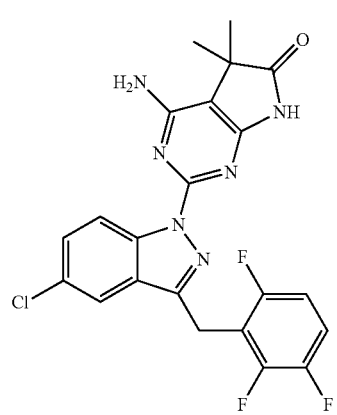
(19)
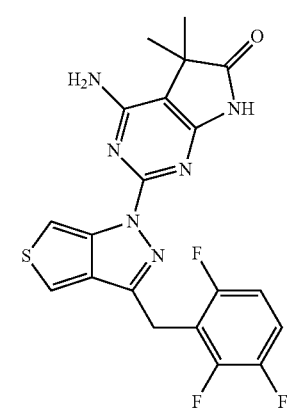
(20)
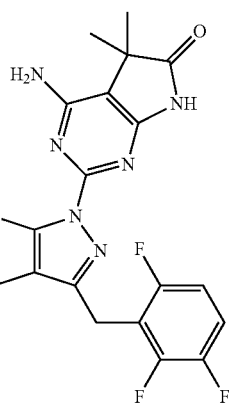
(21)
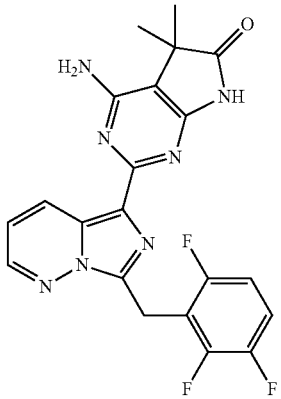
(22)
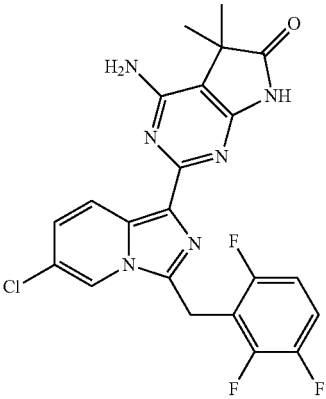
(23)
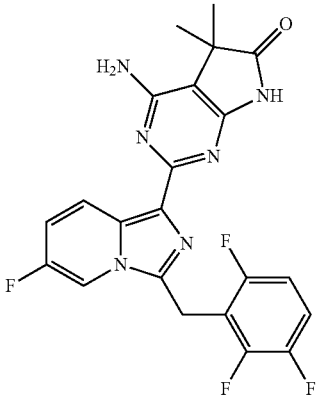

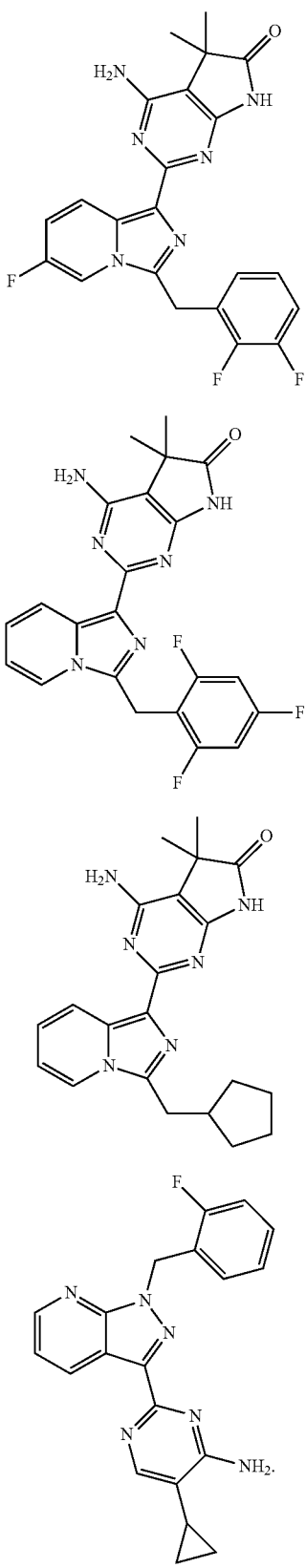

Compounds according to formulae (1), (2), (3), (4), (6)-(8) and (17)-(27) are known as sGC stimulators. Preferred are compounds according to formulae (1), (2), (3), (4), (6), (7) and (27). Especially preferred are compounds according to formulae (3), (4), (6) und (7).

Compounds according to formulae (5) und (9)-(16) are known as sGC activators. Preferred is the compound according to formula (5).

A further embodiment of the invention is the combination of stimulators and/or activators of the soluble guanylate cyclase with PDE5 inhibitors for the prevention and treatment of fibrotic diseases, such as Systemic Sclerosis, scleroderma, and the concomitant fibrosis of internal organs. The following PDE 5 inhibitors are preferred for the combination with sGC stimulators and/or activators:

Tadalafil ((6R,12aR)-2,3,6,7,12,12a-Hexahydro-2-methyl-6-(3,4-methylene-dioxyphenyl) pyrazino(1',2':1,6) pyrido(3,4-b)indole-1,4-dione), Vardenafil (2-(2-Ethoxy-5-(4-ethylpiperazin-1-yl-1-sulfonyl)phenyl)-5-methyl-7-propyl-3H-imidazo (5,1-f) (1,2,4)triazin-4-one), Sildenafil (3-[2-ethoxy-5-(4-methylpiperazin-1-yl)sulfonyl-phenyl]-7-methyl-9-propy 1-2,4,7,8-tetrazabicyclo[4.3.0]nona-3,8,10-trien-5-one), Udenafil 5-[2-propyloxy-5-(1-methyl-2-pyrrolidinylethylamidosulfonyl)phenyl]-methyl-3-propyl-1,6-dihydro-7H-pyrazolo(4,3-d)pyrimidine-7-one, Dasantafil 7-(3-Bromo-4-methoxybenzyl)-1-ethyl-8-[[(1,2)-2-hydroxycyclopentyl]amino]-3-(2-hydroxyethyl)-3,7-dihydro-1-purine-2,6-dione, Avanafil 4-{[(3-chloro-4-methoxyphenyl)methyl]amino}-2-[(2S)-2-(hydroxymethyl)pyrrolidin-1-yl]-N-(pyrimidin-2-ylmethyl)pyrimidine-5-carboxamide, Mirodenafil, Lodenafil, UK 369.003, UK 371.800, SLx 2101 of Surface Logix, LAS 34179Triazolo[1,2-]xanthine, 6-methyl-4-propyl-2-[2-propoxy-5-(4-methylpiperazino) sulfonyl]phenyl or salts, hydrates or hydrates of the salts.

Especially preferred are combinations of compounds according to formulae (1), (2), (3), (4), (6), (7), (27) and/or (5) with vardenafil and/or sildenafil Especially preferred are combinations of compounds according to formulae (3), (4), (6), (7) and/or (5) with vardenafil and/or sildenafil for use in the prevention and/or treatment of Systemic Sclerosis (SSc).

Especially preferred are compounds according to formulae 3, 4, 6, and/or 7 for use in the prevention and/or treatment of Systemic Sclerosis SSc.

Especially preferred are compounds according to formulae 3, 4 and/or 6 for use in the prevention and/or treatment of Systemic Sclerosis SSc.

Especially preferred is at least one compound according to formulae 3, 4, 6, and/or 7 in combination with vardenafil or sildenafil for use in the prevention and/or treatment of scleroderma.

A further embodiment of the invention is the combination of stimulators and/or activators of the soluble guanylate cyclase with imunosupressant therapy (i.e. cyclophosphamide CYP, methotrexate MTX), with kinase inhibitors, (i.e. sorafenib, regorafenib, imatinib, dasatinib), with glucocorticoids (i.e. prednisolon, methylprednisoln), with Anti-CD20 antibodies, with P144 beta-glycan, with abatacept.

A further embodiment of the invention is the combination of stimulators and/or activators of the soluble guanylate cyclase with ACE-inhibitors (i.e. captopril, enalapril), calcium channel blockers (i.e. nifedipine), prostanoids (i.e. iloprost), endothelin antagonists (i.e. bosentan).

Another preferred embodiment of the invention are compounds and/or combinations indicated above for use in the prevention and/or treatment of Systemic Sclerosis (SSc), diffuse Systemic Sclerosis (dSSc), limited Systemic Sclerosis (lSSc), overlap type of Systemic Sclerosis, undifferentiated type of Systemic Sclerosis, Systemic Sclerosis sine scleroderma, skin fibrosis, scleroderma, nephrogenic fibrosing dermopathy (NFD), keloid formation.

Another preferred embodiment of the invention are compounds and/or combinations indicated above for use in the prevention and/or treatment of scleroderma.

Another preferred embodiment of the invention are compounds and/or combinations indicated above for use in the prevention and/or treatment of Systemic Sclerosis SSc concomitant fibrosis of internal organs, comprising the gut, the lung, the kidney and the blood vessels.

Another preferred embodiment of the invention is the use for the production of a medicament for prevention and/or treatment of Systemic Sclerosis (SSc) comprising an effective amount of a compound and/or a combination as indicated above.

Another preferred embodiment of the invention is the use for the production of a medicament for prevention and/or treatment of scleroderma comprising an effective amount of a compound and/or a combination as indicated above.

Another preferred embodiment of the invention is the use for the production of a medicament for prevention and/or treatment of Systemic Sclerosis (SSc), diffuse Systemic Sclerosis (dSSc), limited Systemic Sclerosis (lSSc), overlap type of Systemic Sclerosis, undifferentiated type of Systemic Sclerosis, Systemic Sclerosis sine scleroderma, skin fibrosis, scleroderma, nephrogenic fibrosing dermopathy (NFD), keloid formation comprising an effective amount of a compound and/or a combination as indicated above.

Another preferred embodiment of the invention is the use for the production of a medicament for prevention and/or treatment of Systemic Sclerosis SSc concomitant fibrosis of internal organs, comprising the gut, the lung, the kidney and the blood vessels comprising an effective amount of a compound and/or a combination as indicated above.

Another preferred embodiment of the invention is the pharmaceutical formulation comprising at least one compound or one combination as indicated above for the use in the prevention and/or treatment of Systemic Sclerosis (SSc).

Another preferred embodiment of the invention is the pharmaceutical formulation comprising at least one compound or one combination as indicated above for the use in the prevention and/or treatment of Systemic Sclerosis (SSc), diffuse Systemic Sclerosis (dSSc), limited Systemic Sclerosis (lSSc), overlap type of Systemic Sclerosis, undifferentiated type of Systemic Sclerosis, Systemic Sclerosis sine scleroderma, skin fibrosis, scleroderma, nephrogenic fibrosing dermopathy (NFD), keloid formation.

Another preferred embodiment of the invention is the pharmaceutical formulation comprising at least one compound or one combination as indicated above for the use in the prevention and/or treatment of Systemic Sclerosis (SSc).

Another preferred embodiment of the invention is the pharmaceutical formulation comprising at least one compound or one combination as indicated above for the use in the prevention and/or treatment of Systemic Sclerosis SSc concomitant fibrosis of internal organs, comprising the gut, the lung, the kidney and the blood vessels.

Another preferred embodiment of the invention is a kit comprising at least one sGC stimulator and/or activator as indicated above or a combination as indicated above for the use in the prevention and/or treatment of Systemic Sclerosis (SSc).

Another preferred embodiment of the invention is a kit as indicated above for the use in the prevention and/or treatment of Systemic Sclerosis (SSc), diffuse Systemic Sclerosis (dSSc), limited Systemic Sclerosis (lSSc), overlap type of Systemic Sclerosis, undifferentiated type of Systemic Sclerosis, Systemic Sclerosis sine scleroderma, skin fibrosis, scleroderma, nephrogenic fibrosing dermopathy (NFD), keloid formation.

Another preferred embodiment of the invention is a kit comprising at least one sGC stimulator and/or activator as indicated above or a combination as indicated above for the use in the prevention and/or treatment of scleroderma.

Another preferred embodiment of the invention is a kit as indicated above for the use in the prevention and/or treatment of Systemic Sclerosis SSc concomitant fibrosis of internal organs, comprising the gut, the lung, the kidney and the blood vessels.

A pharmaceutical composition of the invention is formulated to be compatible with its intended route of administration. Examples of routes of administration include parenteral e.g., intravenous, intradermal, subcutaneous' oral (e.g. 'inhalation)' transdermal (topical) transmucosal and rectal administration. Pharmaceutical compositions suitable for injectable use include sterile aqueous solutions (where water soluble) or dispersions and sterile powders for the extemporaneous preparation of sterile injectable solutions or dispersions. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents for example, parabens, chlorobutanol, phenol, ascorbic acid, thimerosal, and the like. In many cases, it will be preferable to include isotonic agents, for example, sugars, polyalcohols such as maitol sorbitol sodium chloride in the composition.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or coni starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g. 'a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Bio degradable, biocompatible polymers can be used, such as ethylene vinyl acetate, polyanhydrides, polyglycolic acid, collagen, polyorthoesters, and polylactic acid.

DRAWINGS

FIG. 1: Effects of the compound of formula 27 on mean arterial blood pressure (left) and heart rate (right).

Figures 1, 1A, 2, 3:
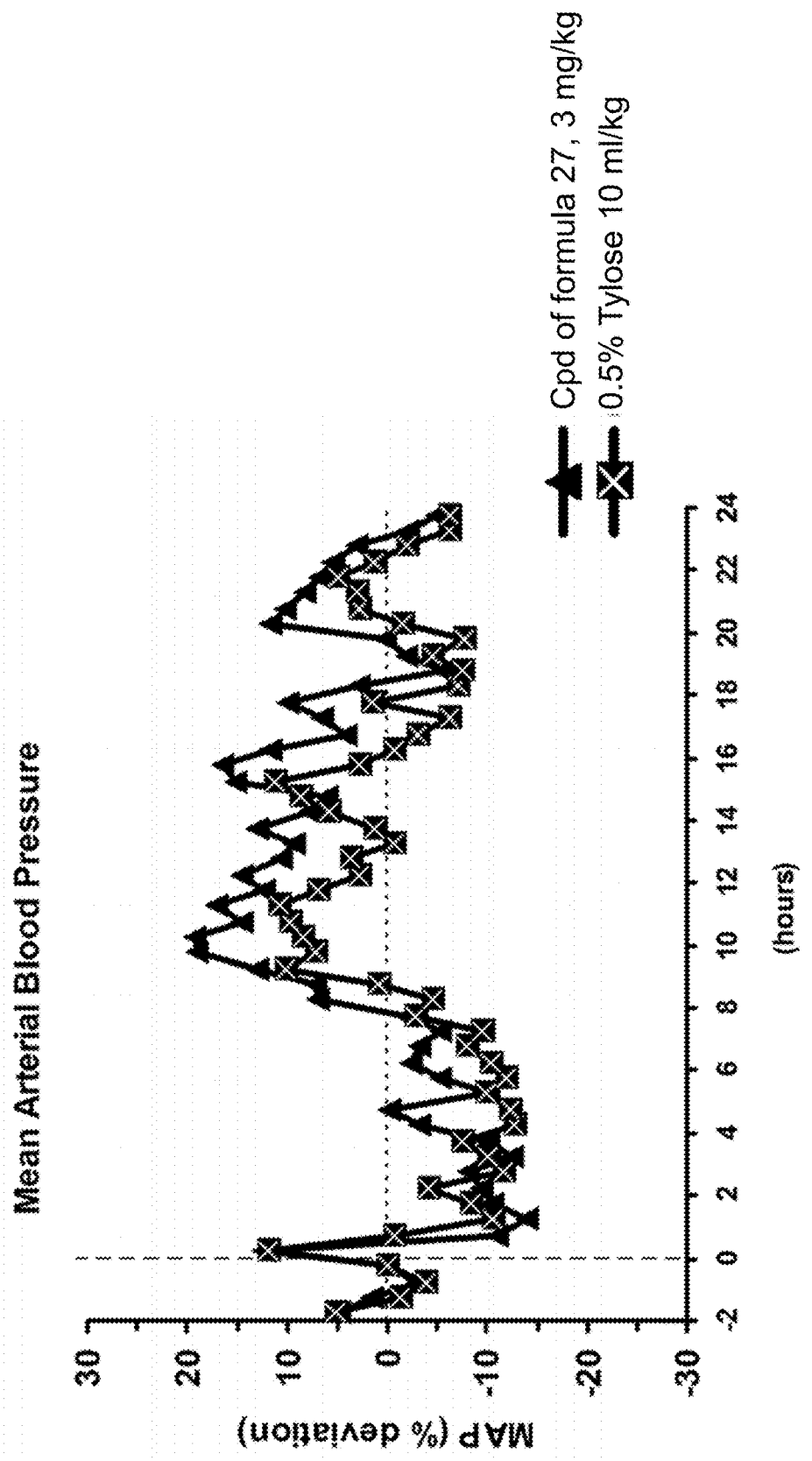
Figure 1B:
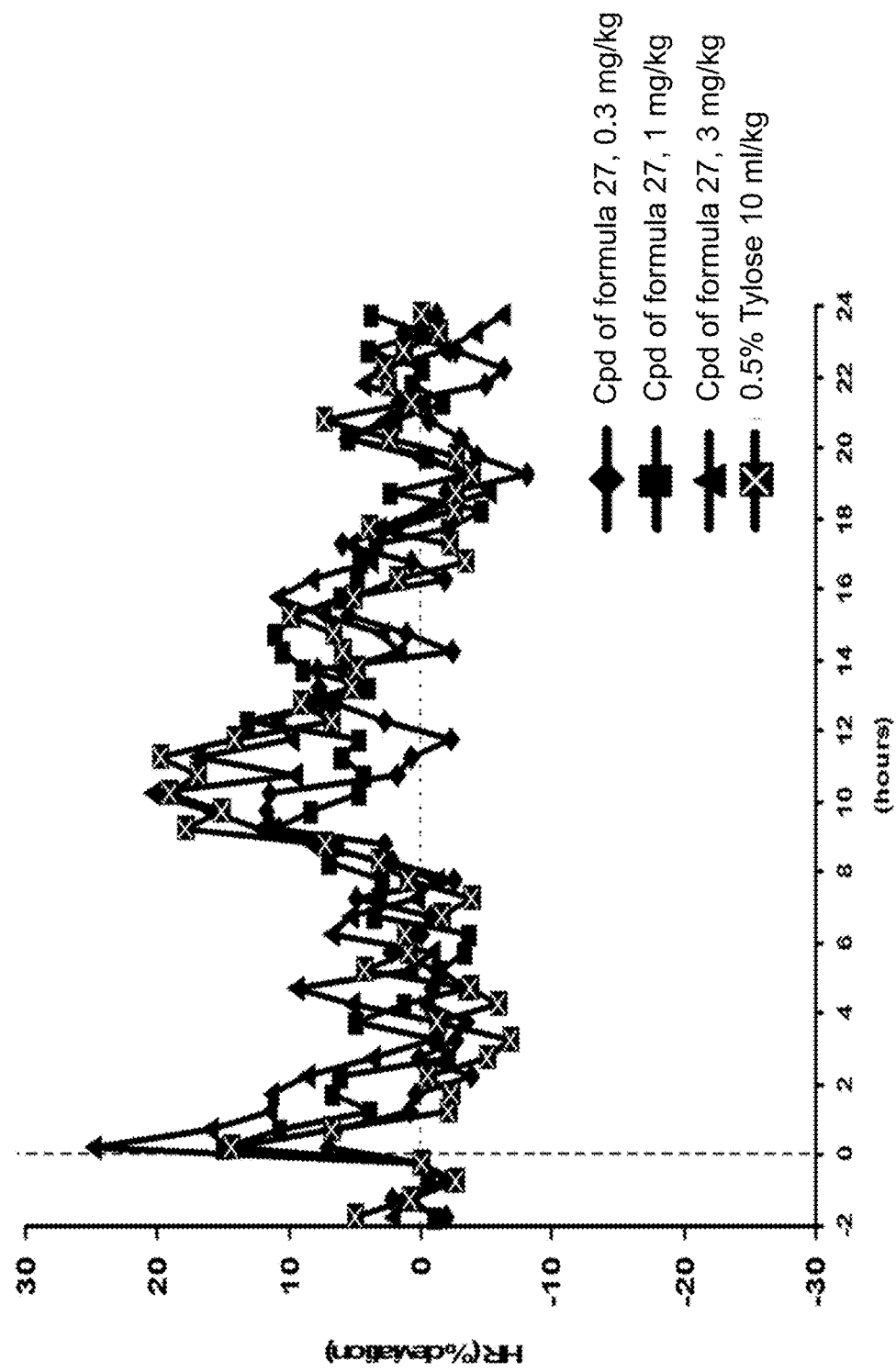
Figures 1, 1B:
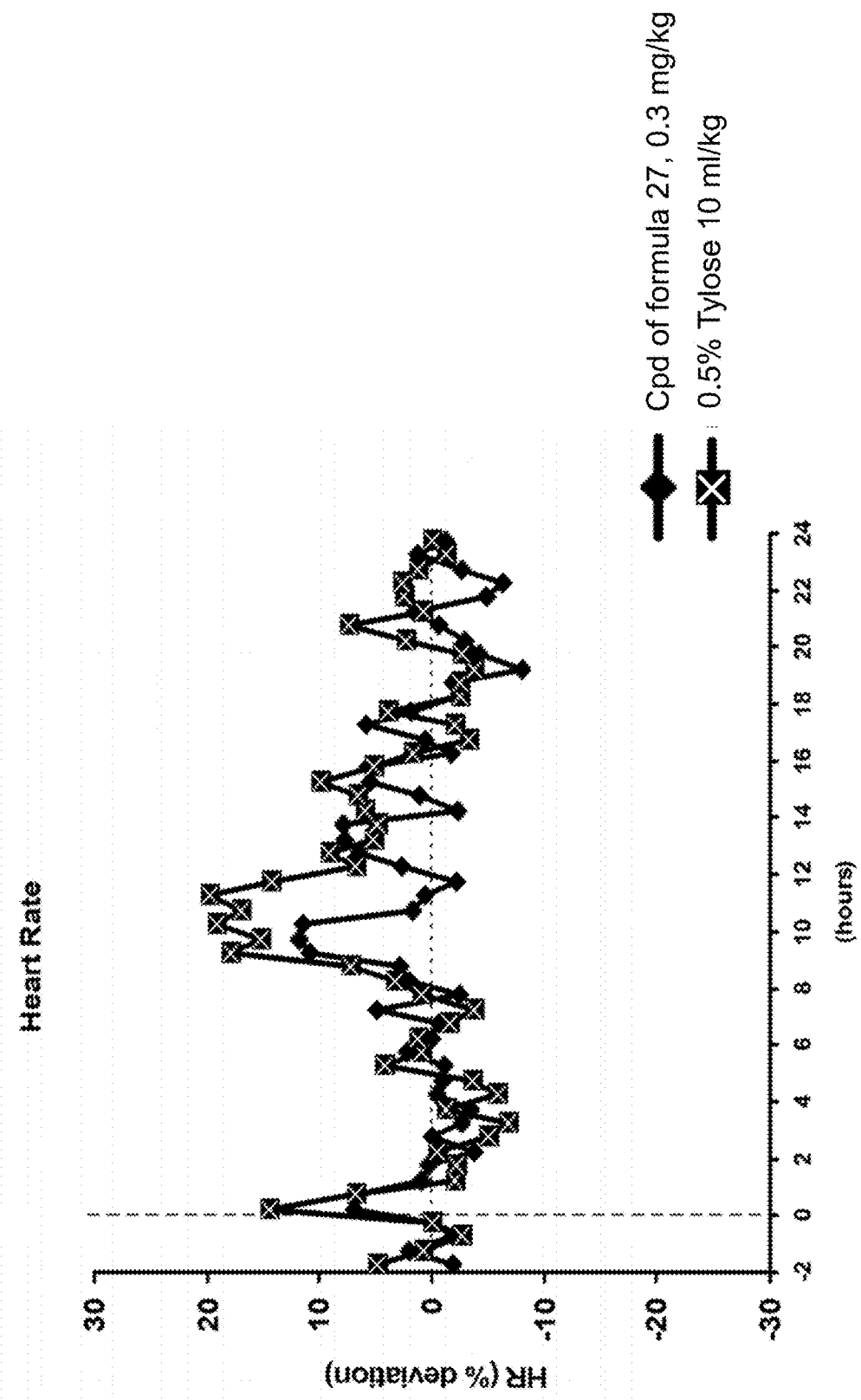
Figures 1, 1B, 2:
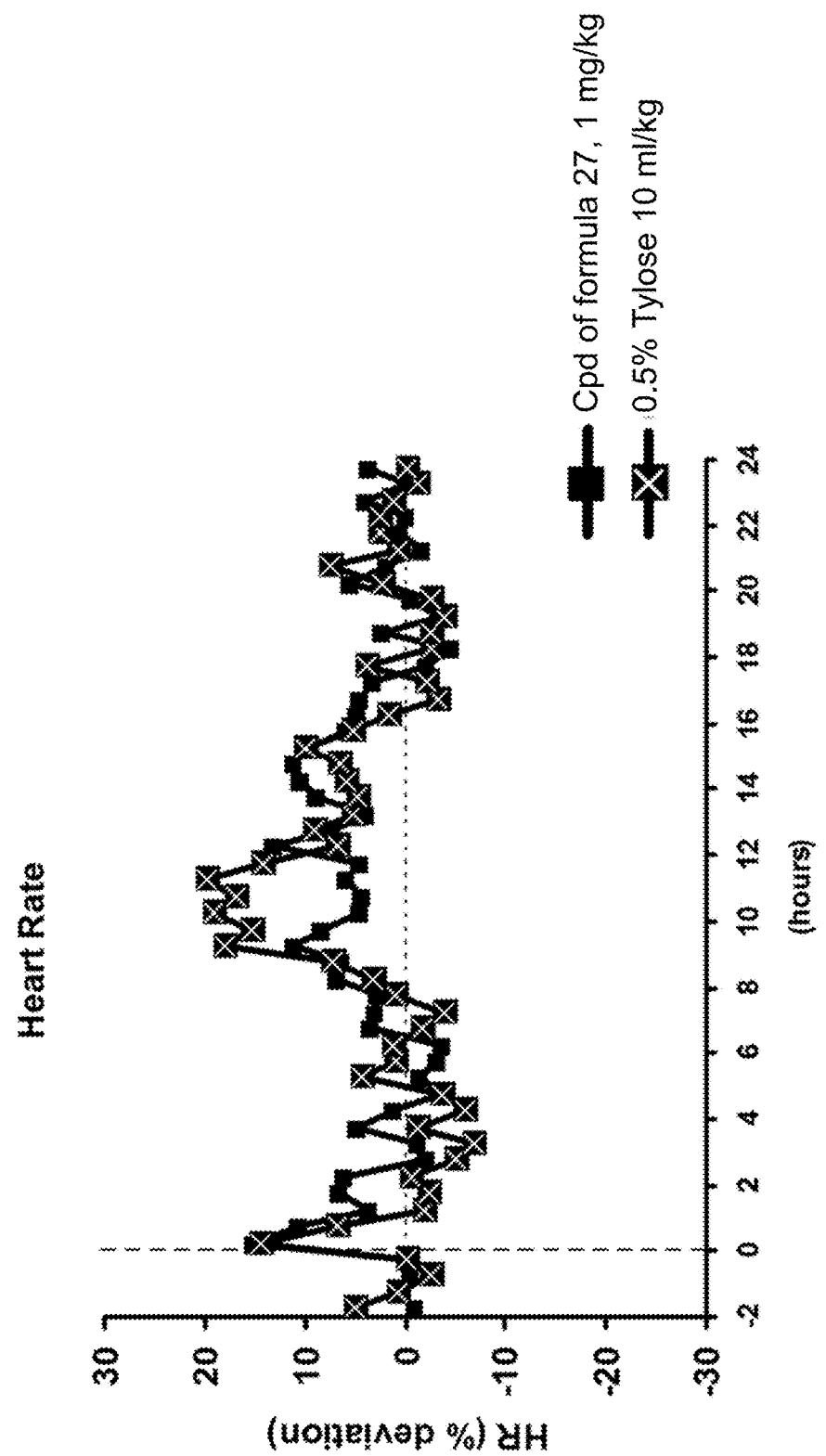
Figures 1, 1B, 2, 3:
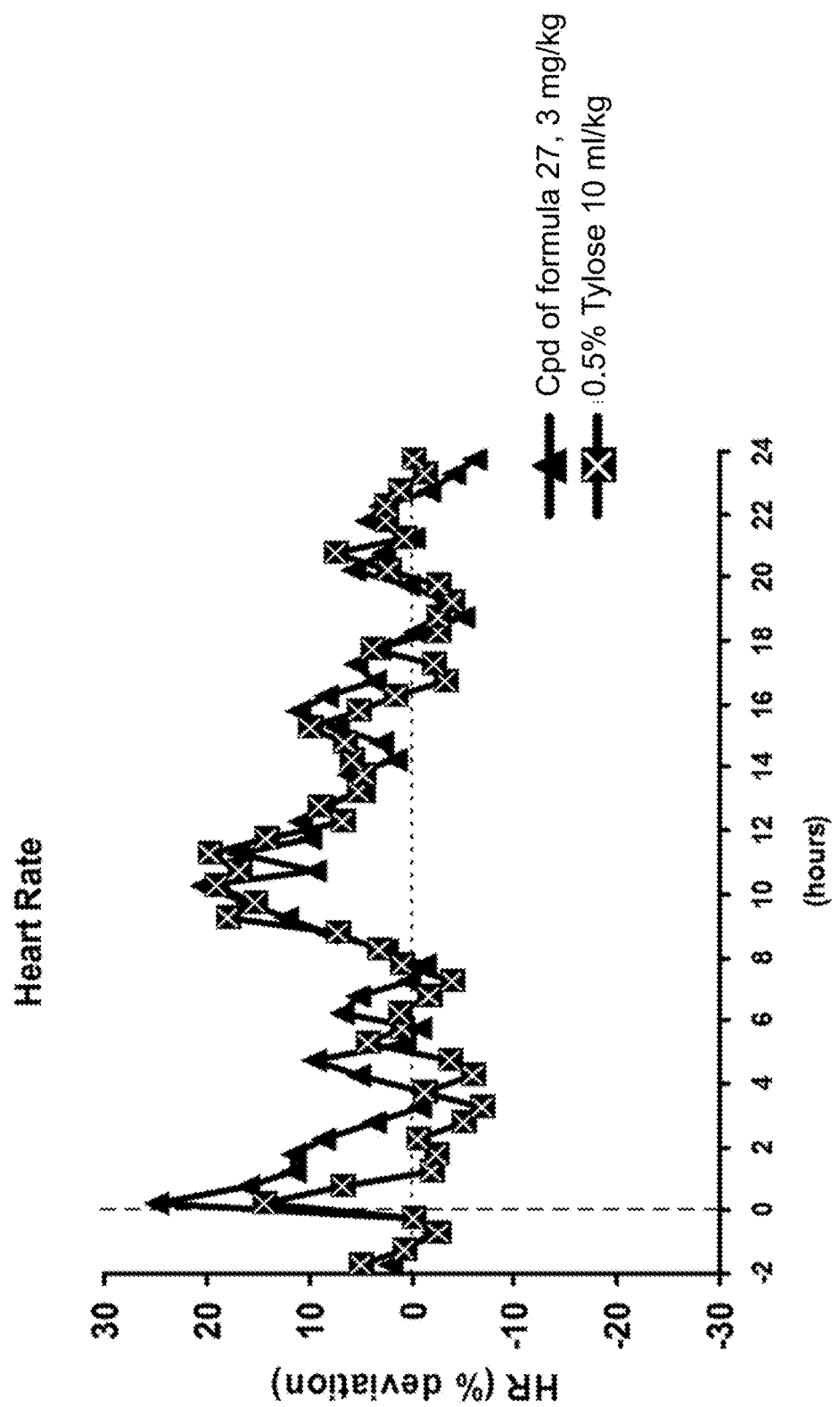
Figures 1, 2A:
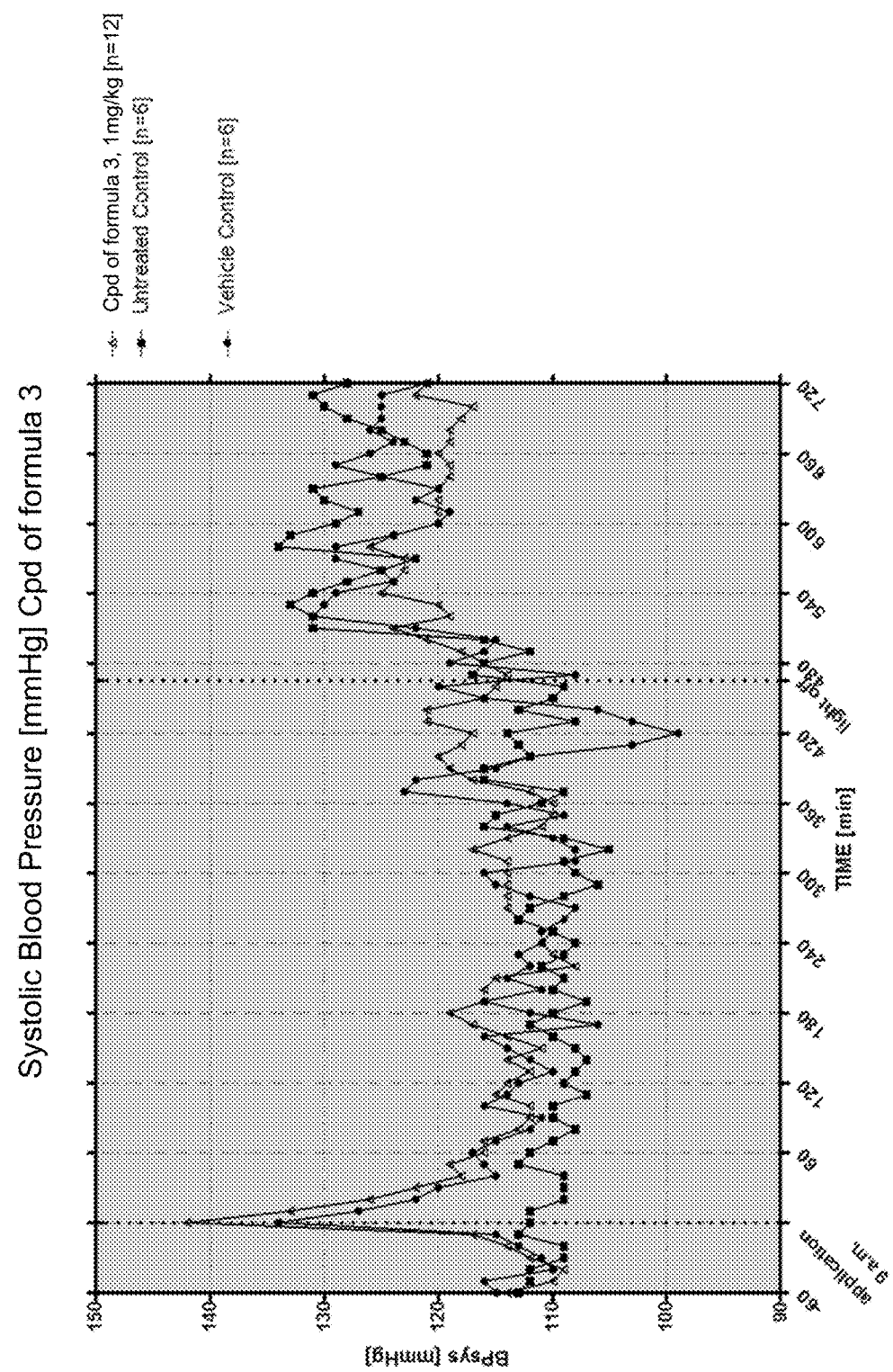
Figures 2, 2A:
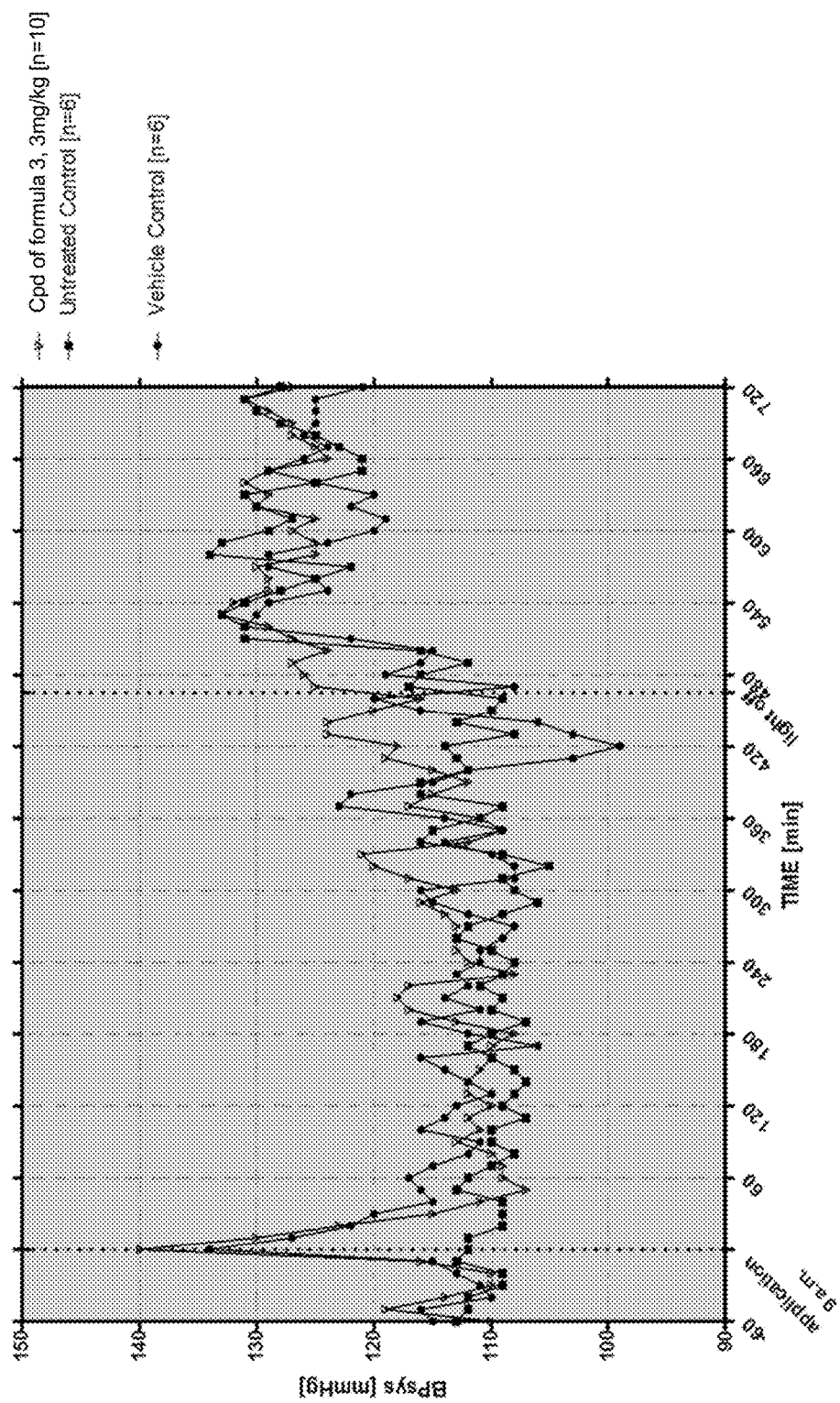
Figures 2, 2A, 3:
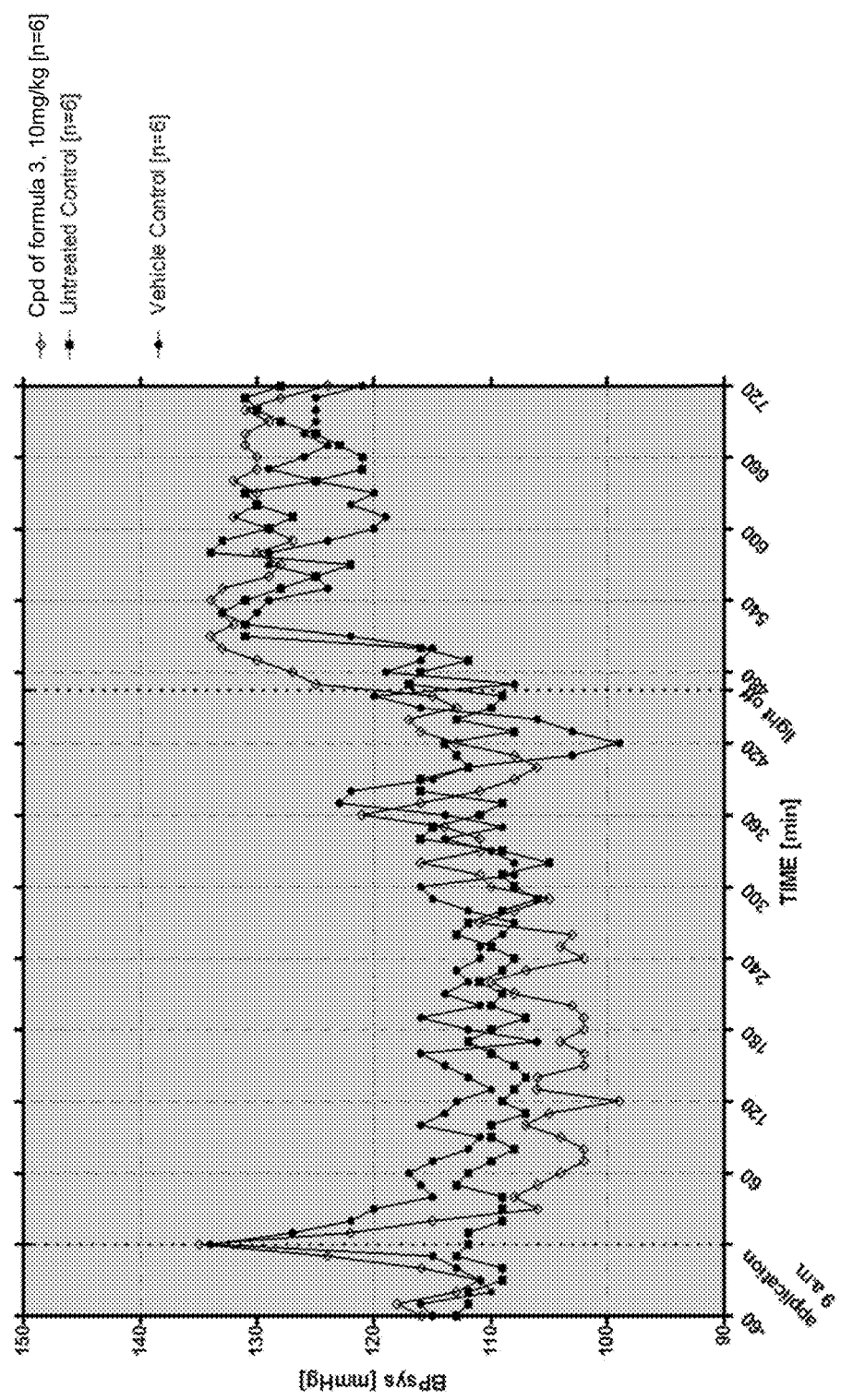

FIG. 2A and FIG. 2B: Effects of the compound of formula 3 on systolic blood pressure (2A) and heart rate (2B)

Figures 1, 3A:
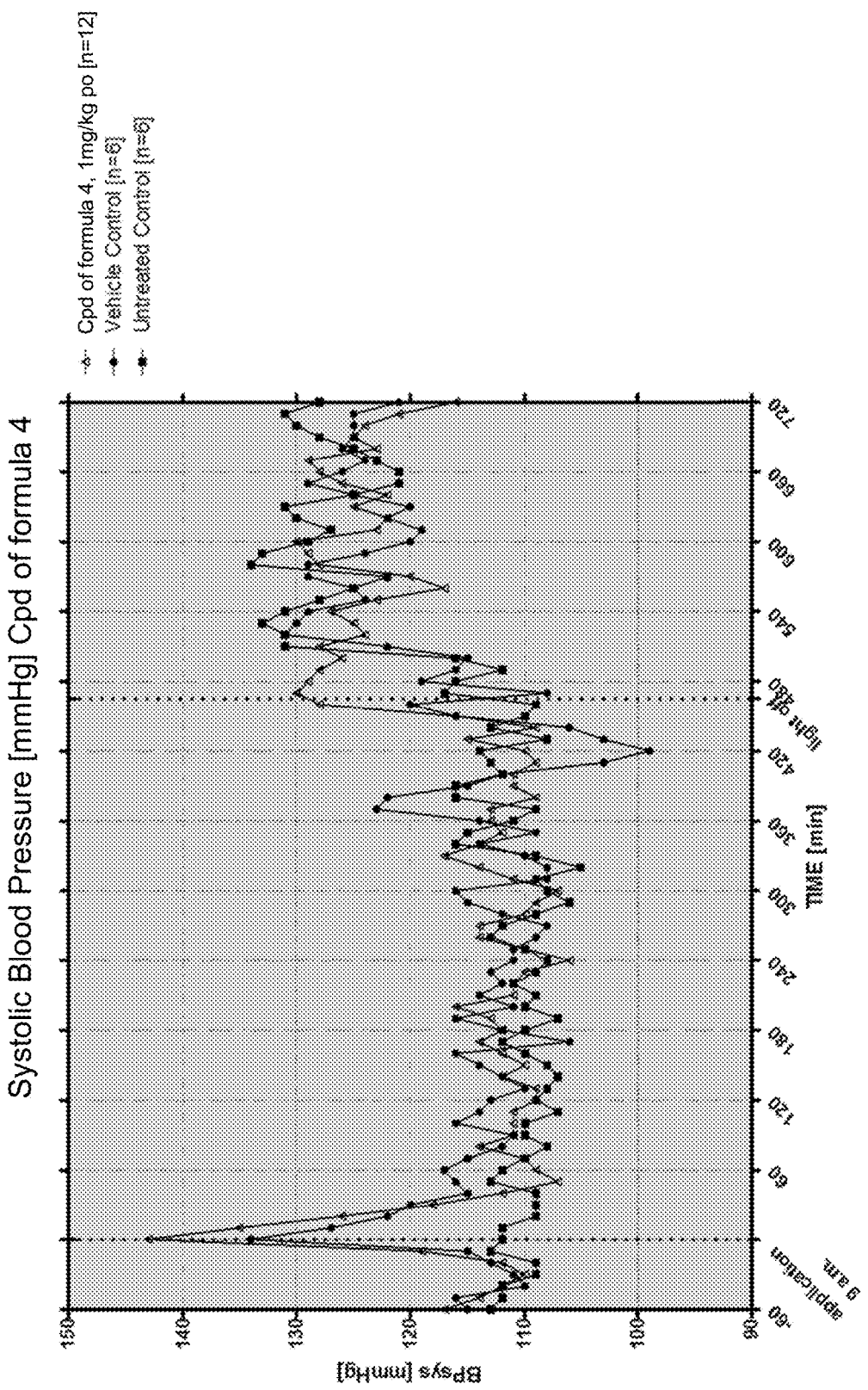
Figures 2, 3A:
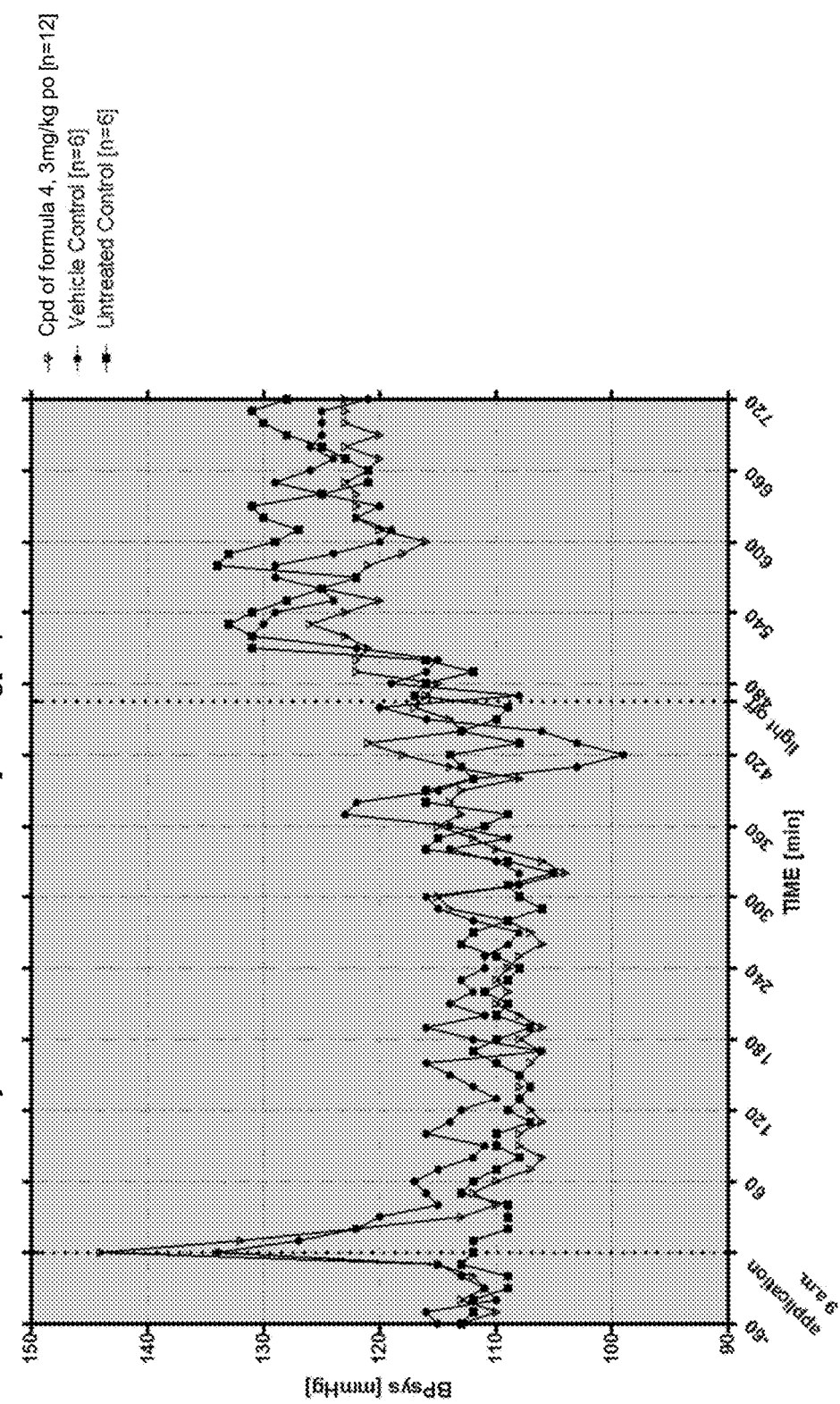
Figures 3, 3A:
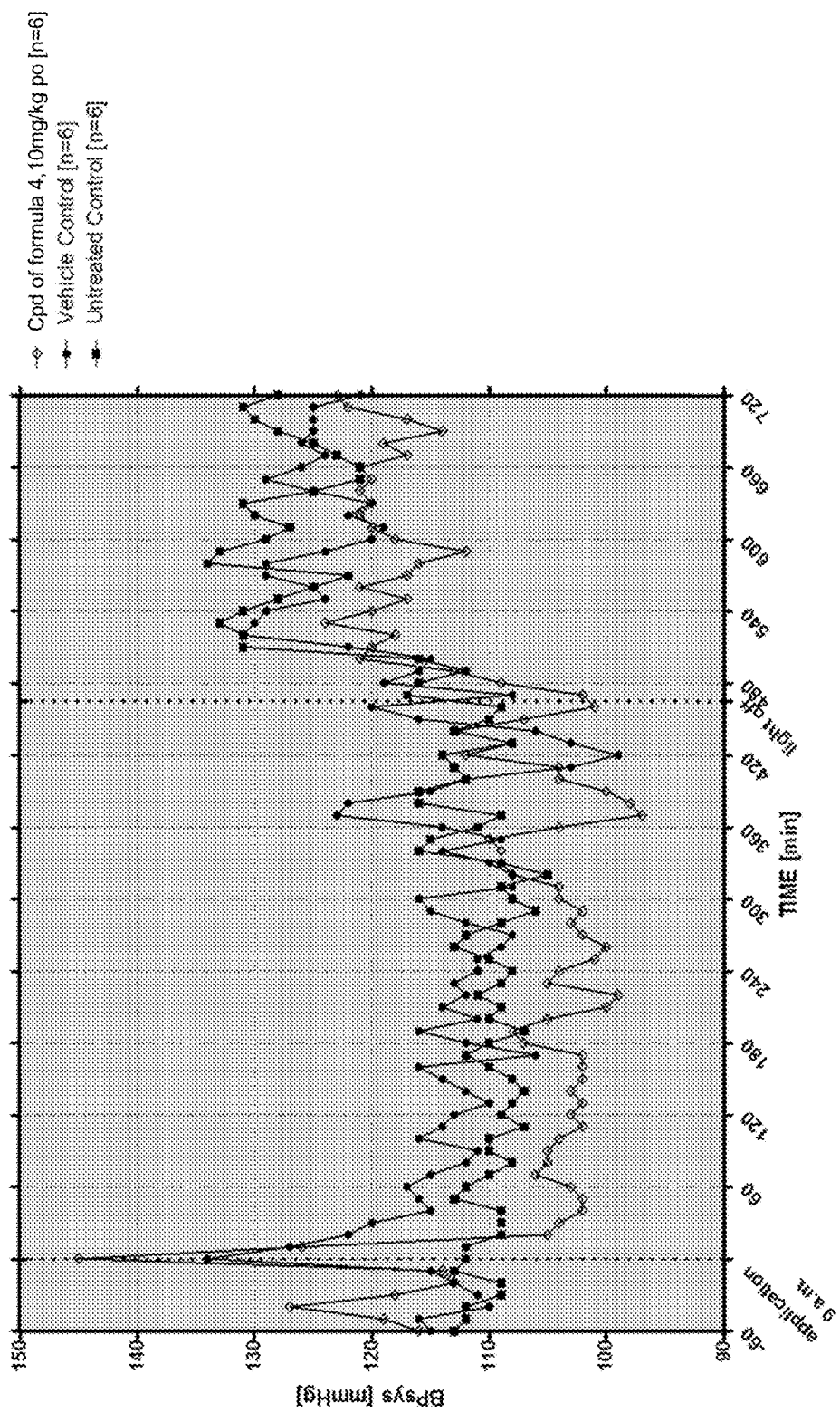
Figures 1, 3B:
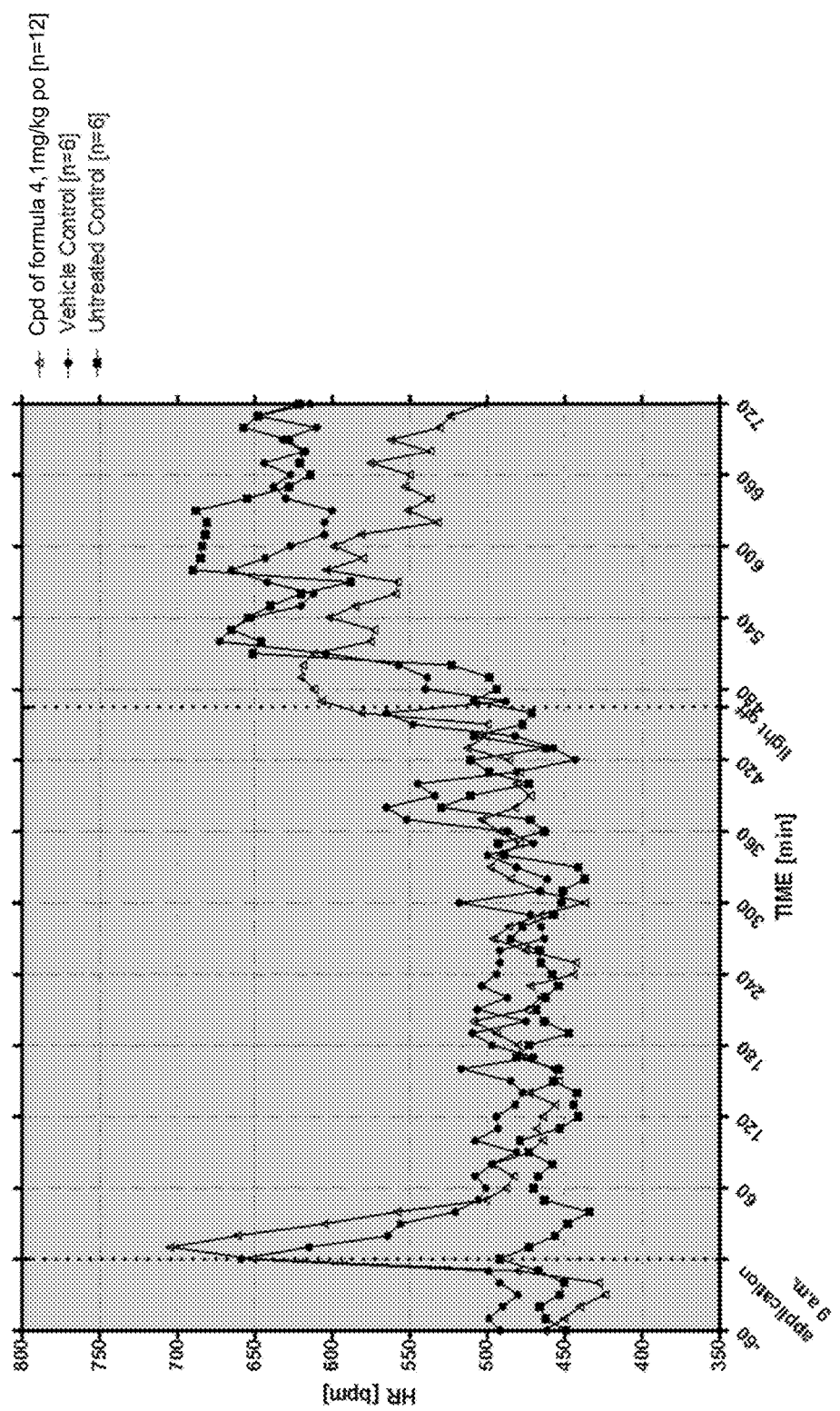
Figures 2, 3B:
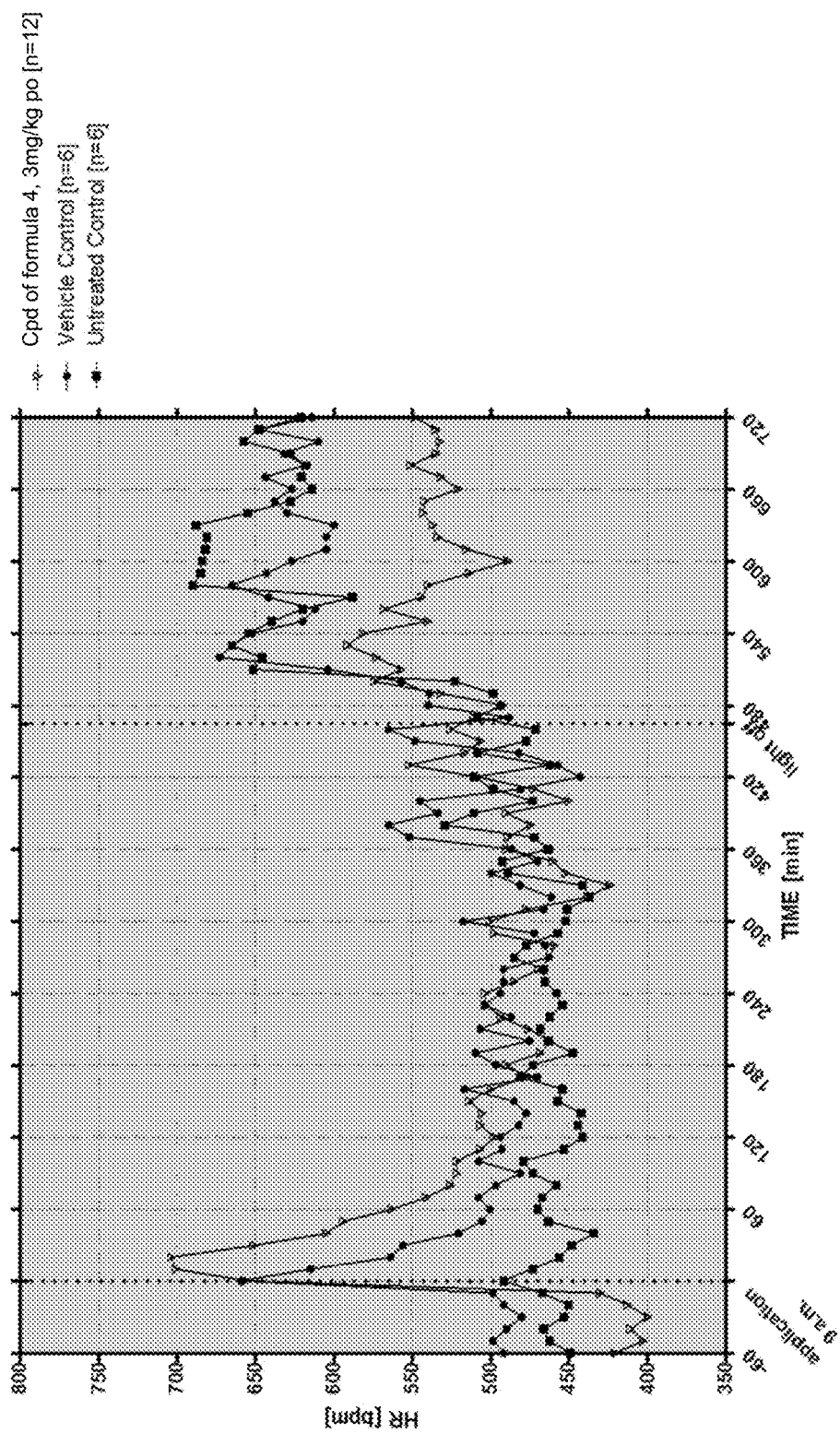

FIG. 3A and FIG. 3B: Effects of the compound of formula 4 on systolic blood pressure (3A) and heart rate (3B)

Figure 4A:
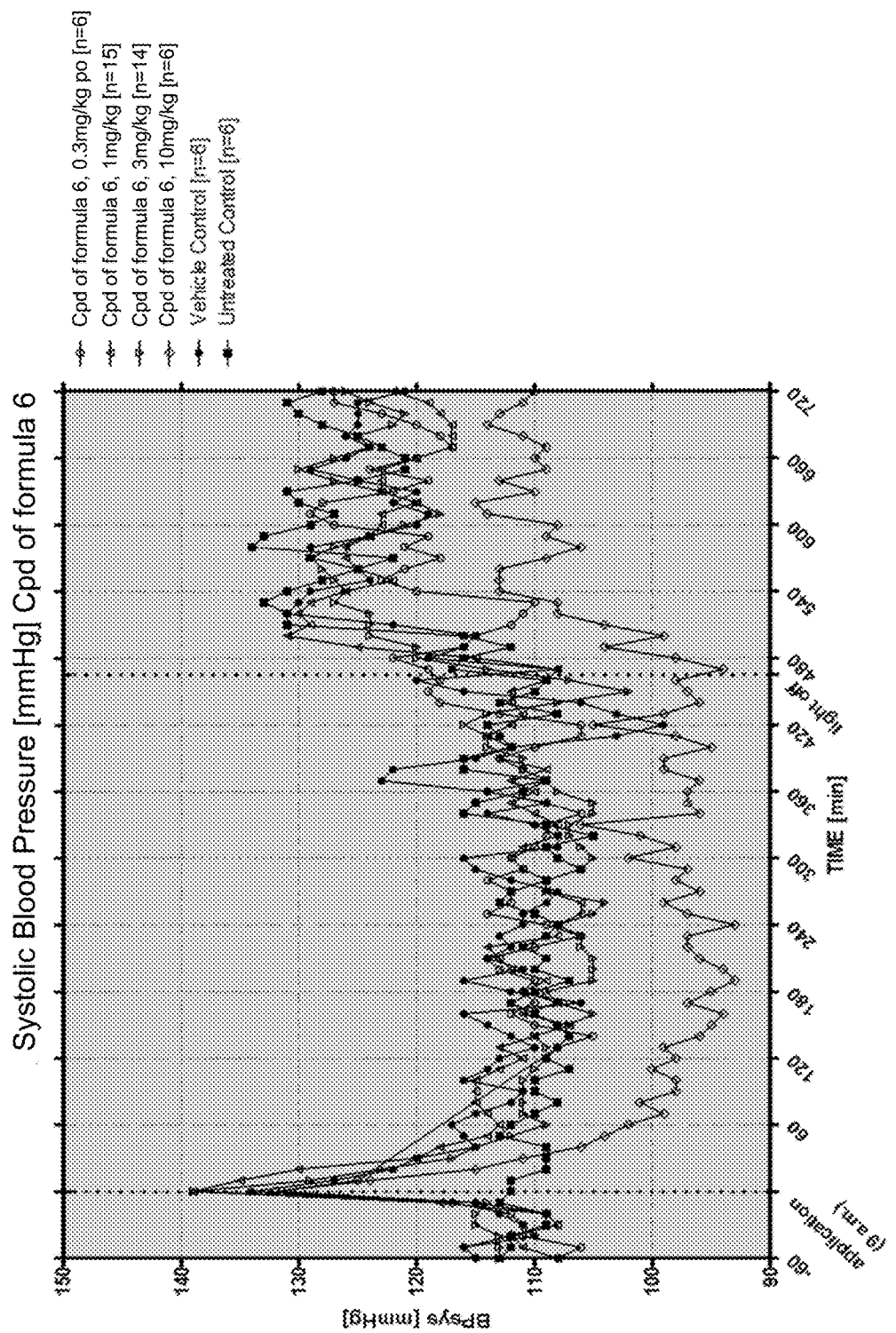
Figures 1, 4A:
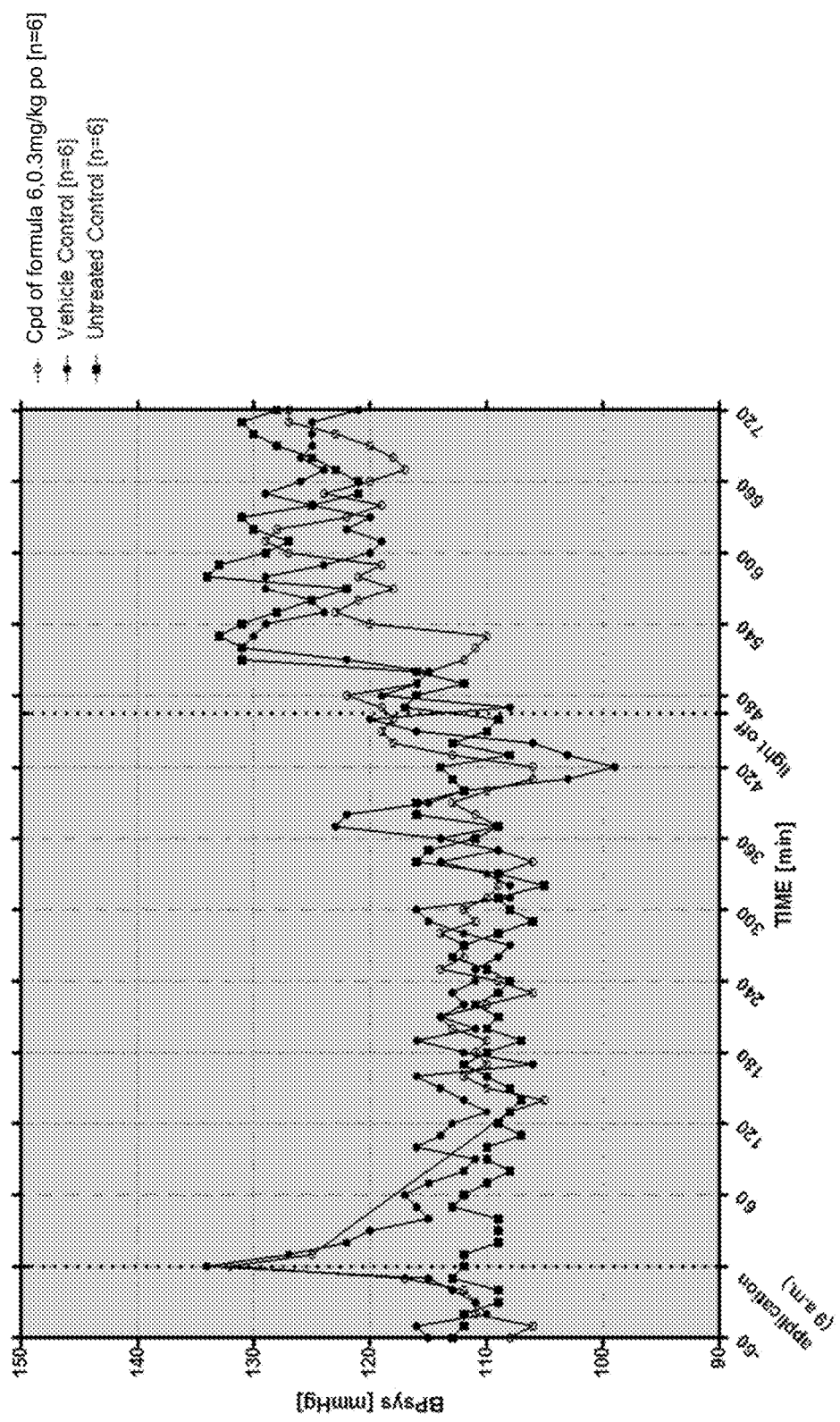
Figures 2, 4A:
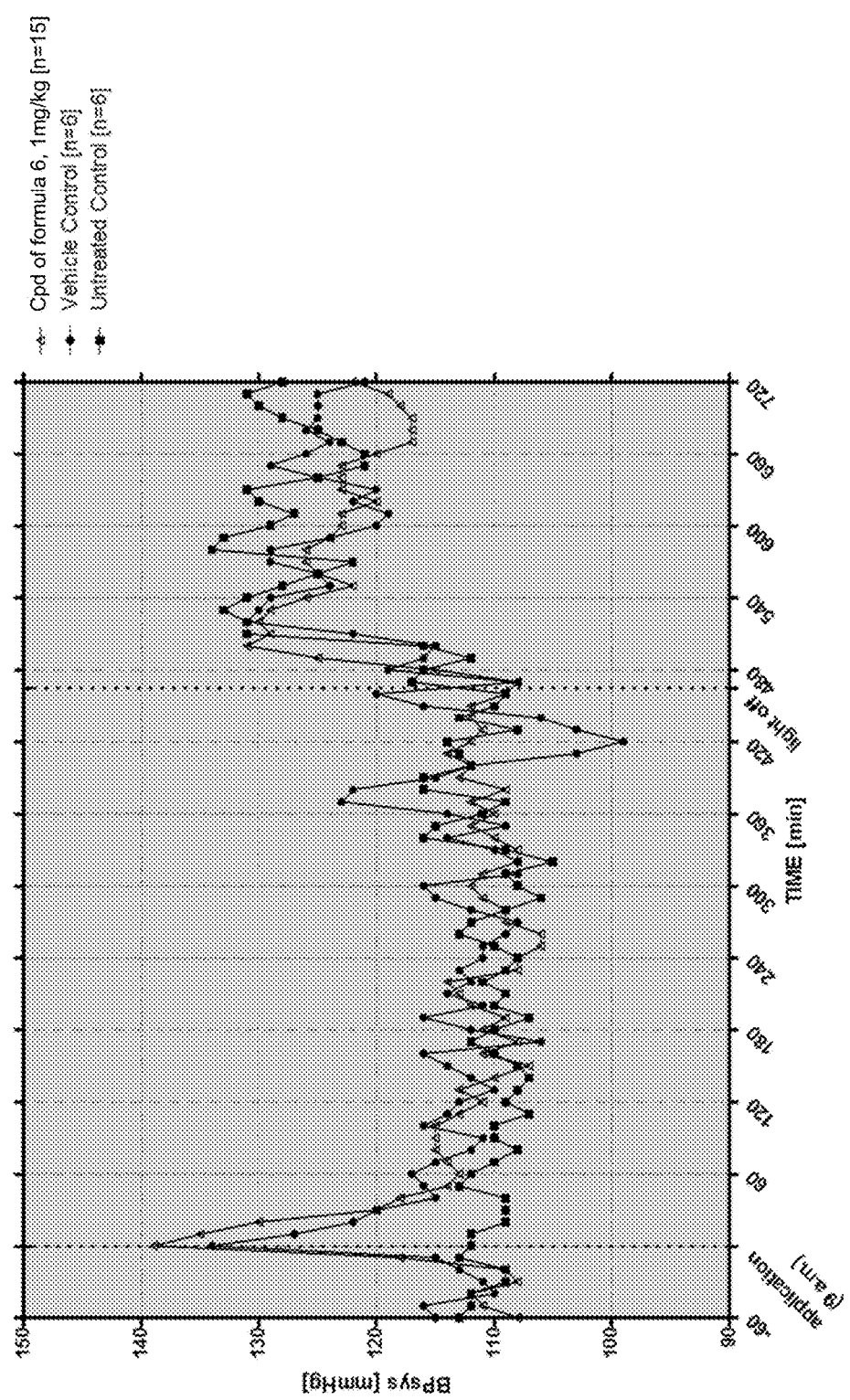
Figures 3, 4A:
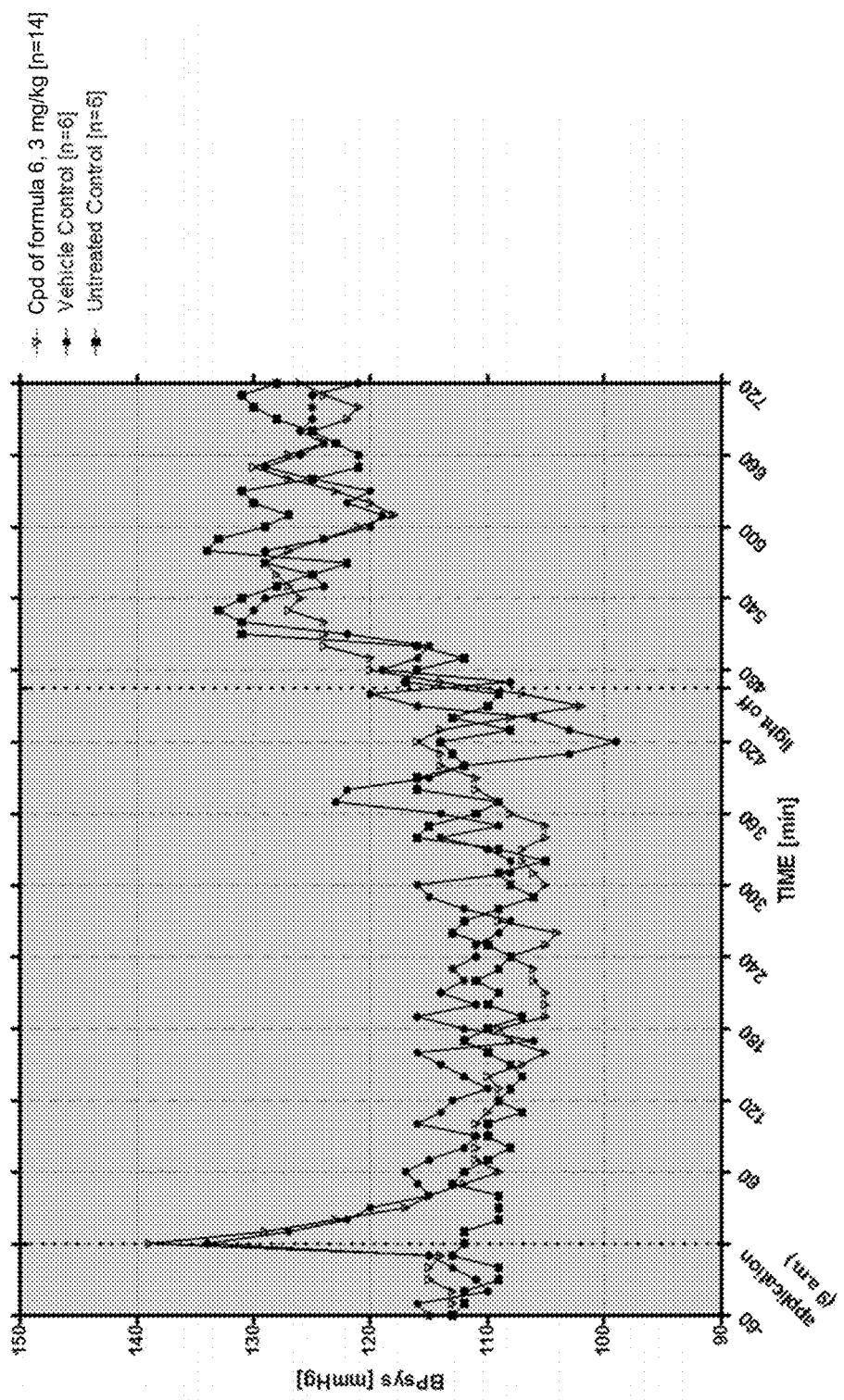
Figures 4, 4A:
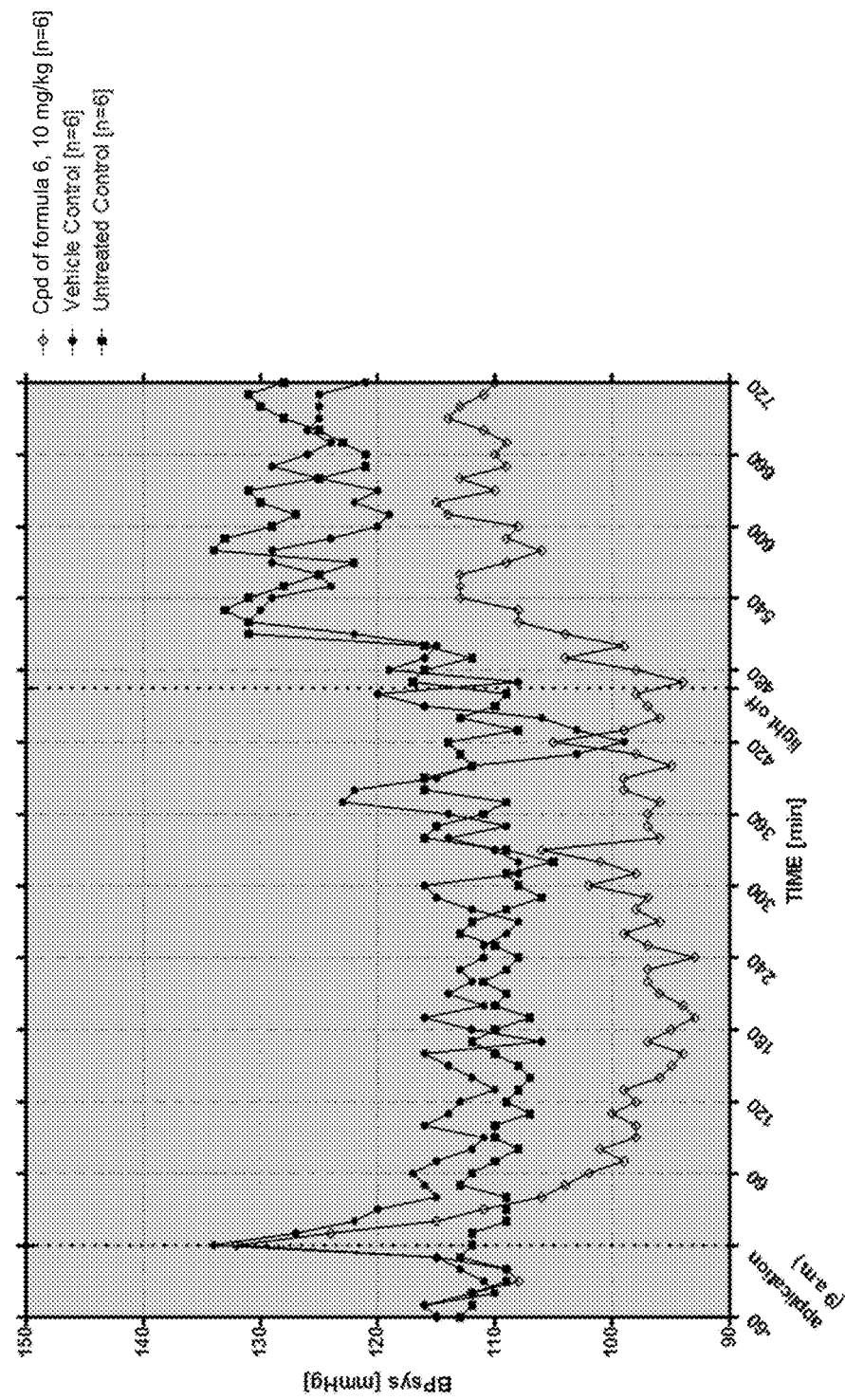
Figure 4B:
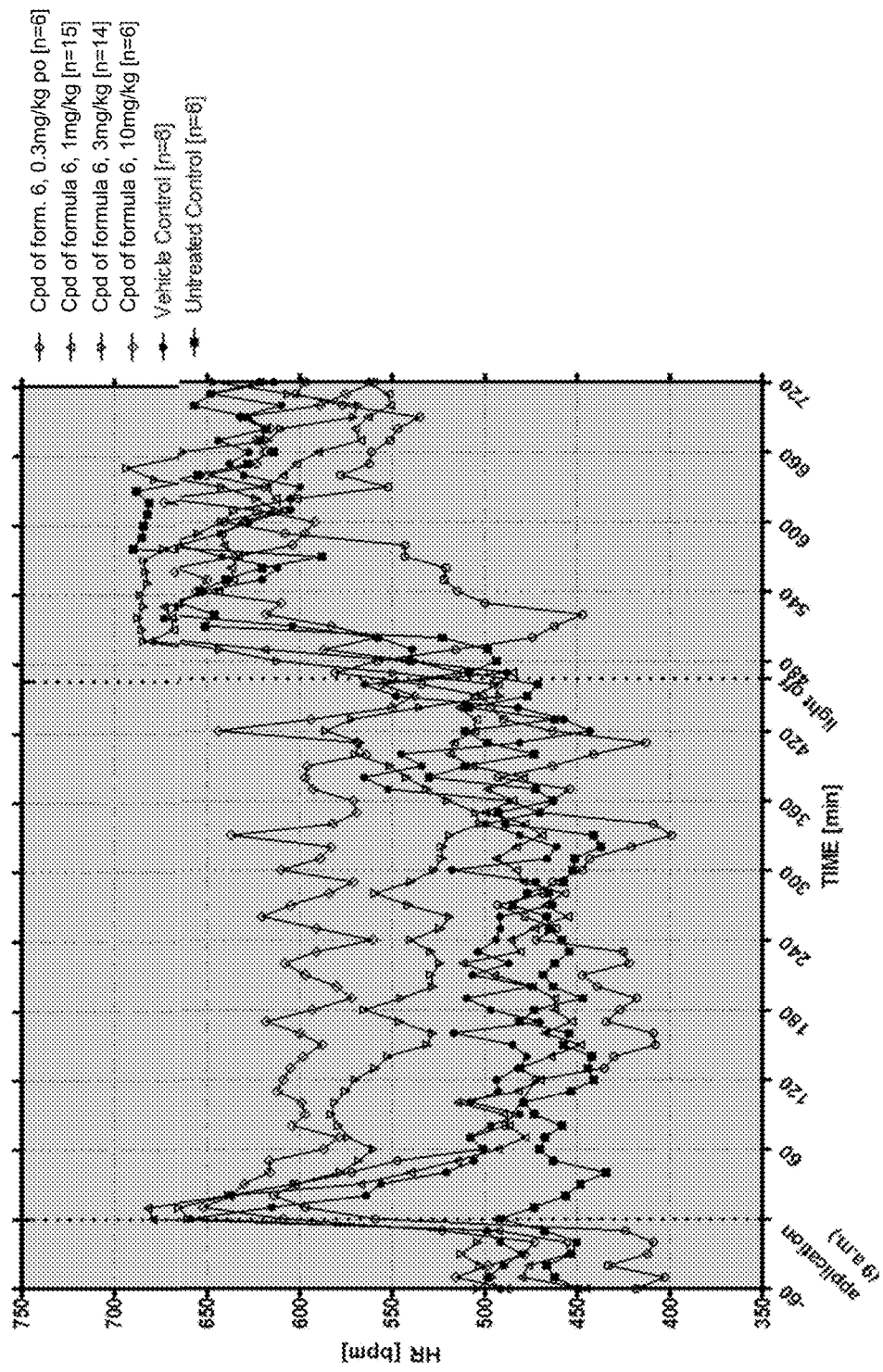
Figures 1, 4B:
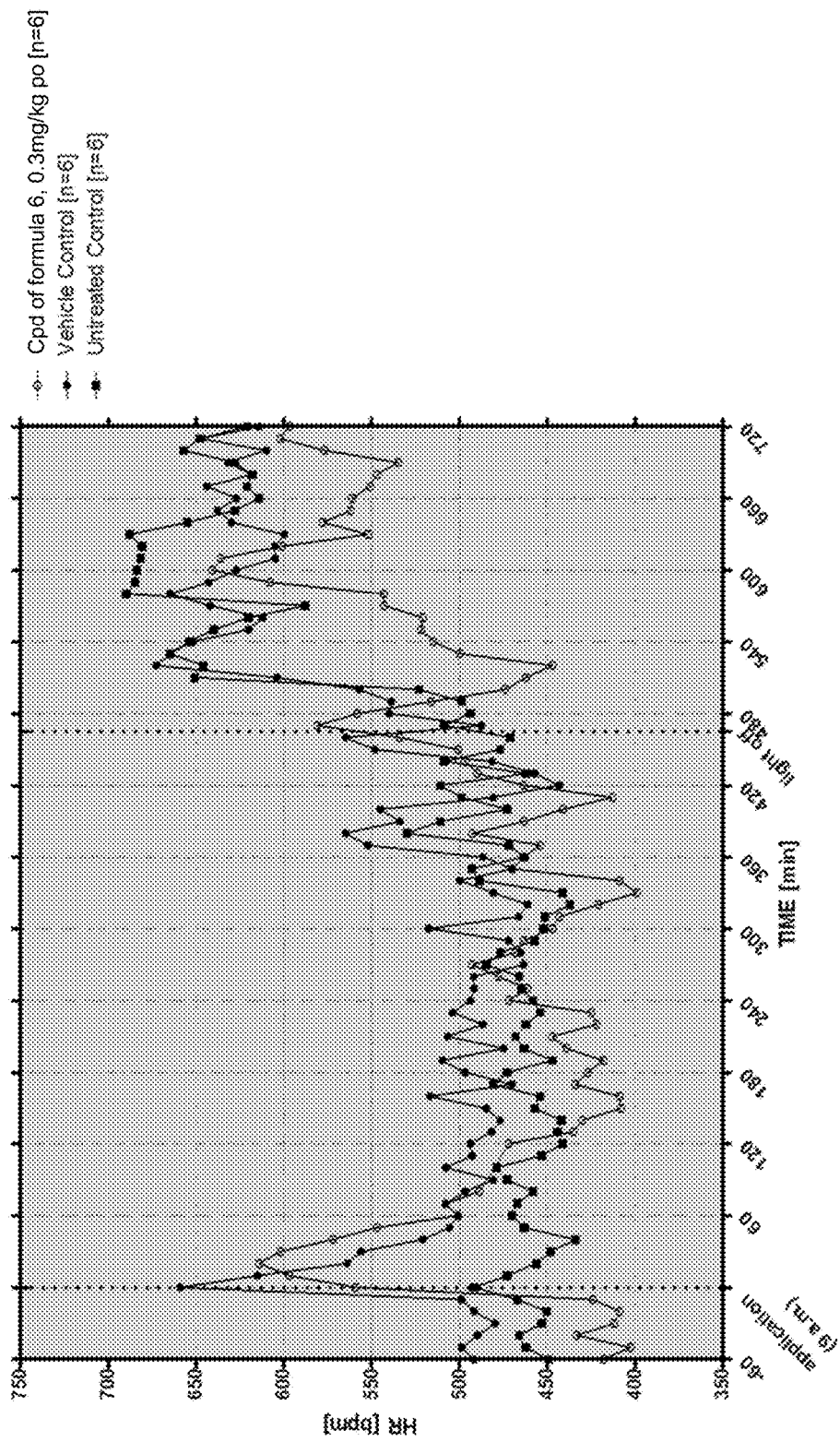
Figures 2, 4B:
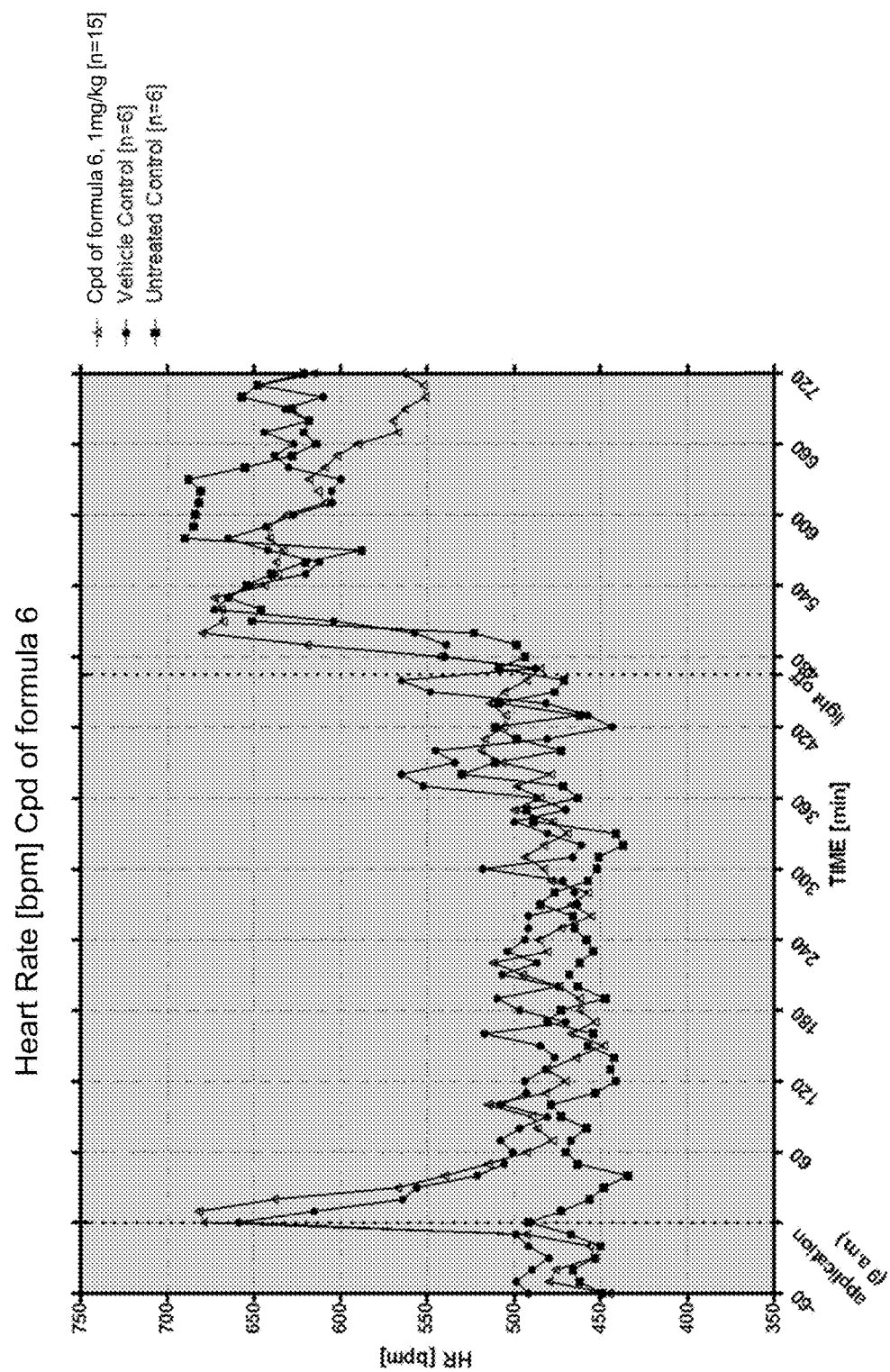
Figures 3, 4B:
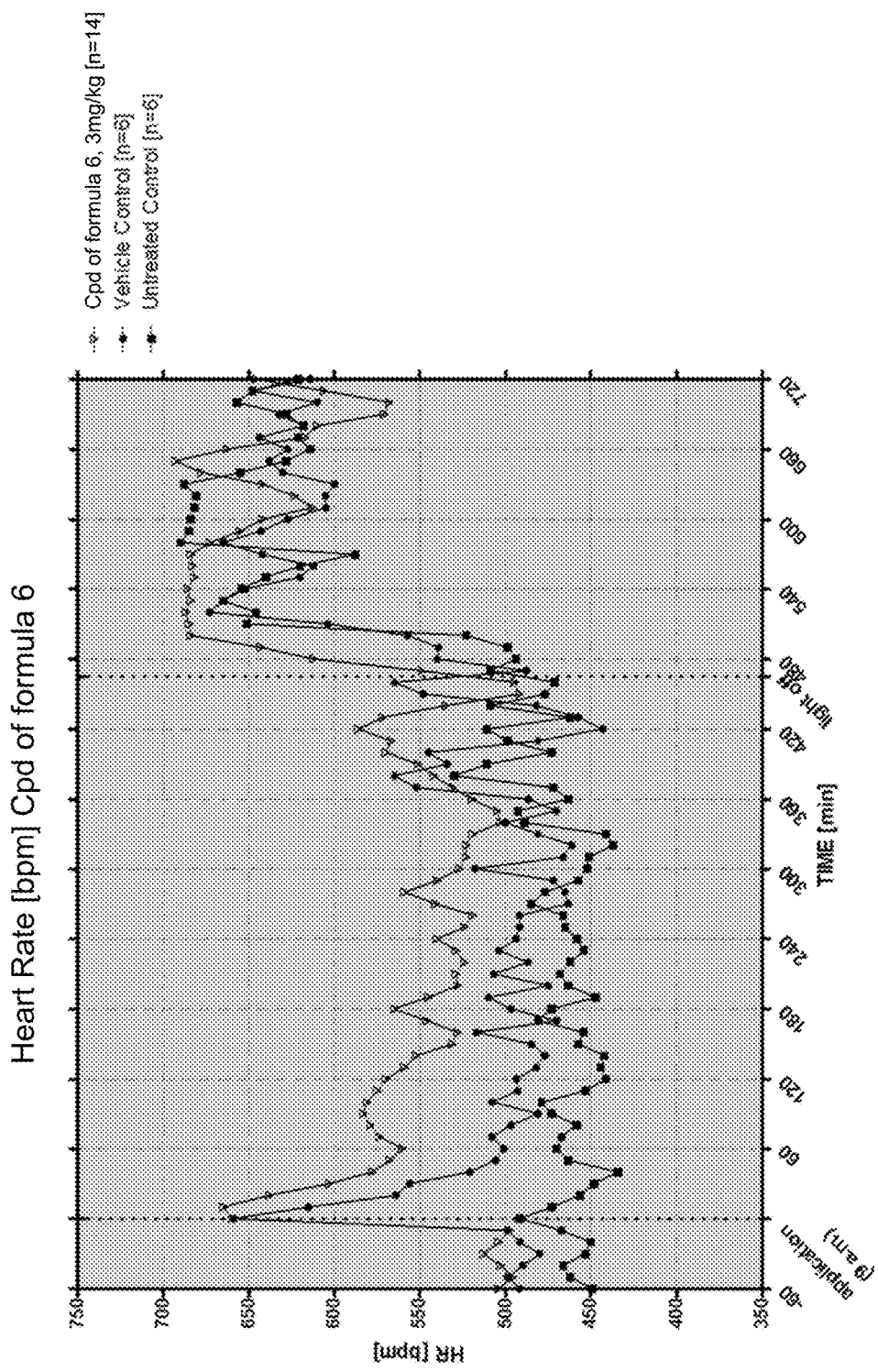

FIG. 4A and FIG. 4B: Effects of the compound of formula 7 on systolic blood pressure (4A) and heart rate (4B)

EXPERIMENTAL PART

A. Examples

Abbreviations and Acronyms aq. aqueous solution
calc. calculated
DCI direct chemical ionization (in MS)
DMF dimethylformamide
DMSO dimethyl sulfoxide
of th. of theory (in yield)
eq. equivalent(s)
ESI electrospray ionization (in MS)
Et ethyl
fnd. found
h hour(s)
HPLC high-pressure, high-performance liquid chromatography
HRMS high-resolution mass spectrometry
conc. concentrated
LC/MS liquid chromatography-coupled mass spectrometry
LiHMDS lithium hexamethyldisilazide
Me methyl
min minute(s)
MS mass spectrometry
NMR nuclear magnetic resonance spectrometry
$Pd_2dba_3$ tris(dibenzylideneacetone)dipalladium
Ph phenyl
RT room temperature
$R_t$ retention time (in HPLC)
THF tetrahydrofuran
UV ultraviolet spectrometry
v/v volume to volume ratio (of a solution)
XPHOS dicyclohexyl(2',4',6'-triisopropylbiphenyl-2-yl)phosphine LC/MS-Methods:

Method 1: MS instrument: Waters ZQ; HPLC instrument: Agilent 1100 Series; UV DAD; Column: Thermo Hypersil GOLD 3μ 20 mm×4 mm; Eluent A: 1 l water+0.5 ml 50% formic acid, Eluent B: 1 l acetonitrile+0.5 ml of 50% formic acid; Gradient: 0.0 min 100% A→3.0 min 10% A→4.0 min 10% A→4.1 min 100% A (flow rate 2.5 ml/min); Oven: 55° C.; Flow rate: 2 ml/min; UV detection: 210 nm.

Method 2: Instrument: Waters ACQUITY SQD UPLC System; Column: Waters Acquity UPLC HSS T3 1.8μ 50×1 mm; Eluent A: 1 l water+0.25 ml 99% formic acid, Eluent B: 1 l acetonitrile+0.25 ml 99% formic acid; Gradient: 0.0 min 90% A→1.2 min 5% A→2.0 min 5% A; Oven: 50° C.; Flow rate: 0.40 ml/min; UV detection: 210-400 nm.

Starting Compounds and Intermediates

Example 1A 2,6-Dichloro-5-fluoronicotinamide

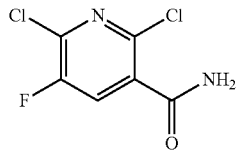

A suspension of 25 g (130.90 mmol) of 2,6-dichloro-5-fluoro-3-cyanopyridine in conc. sulphuric acid (125 ml) was stirred at 60-65° C. for 1 h. After cooling to RT, the contents of the flask were poured into ice-water and extracted three times with ethyl acetate (100 ml each time). The combined organic phases were washed with water (100 ml) and then with saturated aqueous sodium hydrogen carbonate solution (100 ml), dried and concentrated on a rotary evaporator. The material obtained was dried under a high vacuum.

Yield: 24.5 g (90% of theory)

$^1$H NMR (400 MHz, DMSO-$d_6$): δ=7.95 (br s, 1H), 8.11 (br s, 1H), 8.24 (d, 1H).

Example 2A

2-Chloro-5-fluoronicotinamide

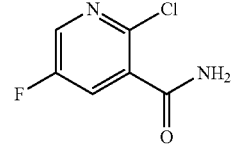 [SMILES: NC(=O)c1cc(F)cnc1Cl]

A suspension of 21.9 g (335.35 mmol) of zinc in methanol (207 ml) was admixed at RT with 44 g (210.58 mmol) of 2,6-dichloro-5-fluoronicotinamide. Then acetic acid (18.5 ml) was added and the mixture was heated with stirring at reflux for 24 h. Thereafter the contents of the flask were decanted from the zinc, and ethyl acetate (414 ml) and saturated aqueous sodium hydrogen carbonate solution (414 ml) were added, followed by intense extractive stirring. Subsequently the reaction mixture was filtered with suction over kieselguhr and the filter product was washed three times with ethyl acetate (517 ml each time). The organic phase was separated off and the aqueous phase was washed with ethyl acetate (258 ml). The combined organic phases were washed once with saturated aqueous sodium hydrogen carbonate solution (414 ml), dried and concentrated under

Example 3A

2-Chloro-5-fluornicotinonitrile

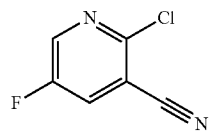

A suspension of 46.2 g (264.66 mmol) of 2-chloro-5-fluoronicotinamide in dichloromethane (783 ml) was admixed with 81.2 ml (582.25 mmol) of triethylamine and cooled to 0° C. Then, with stirring, 41.12 ml (291.13 mmol) of trifluoroacetic anhydride were added slowly dropwise and the mixture was stirred at 0° C. for 1.5 h. The reaction solution was subsequently washed twice with saturated aqueous sodium hydrogen carbon solution (391 ml each time), dried and concentrated under reduced pressure.

Yield: 42.1 g (90% of theory).

$^1$H NMR (400 MHz, DMSO-$d_6$): δ=8.66 (dd, 1H), 8.82 (d, 1H).

Example 4A

5-Fluoro-1H-pyrazolo[3,4-b]pyridin-3-amine

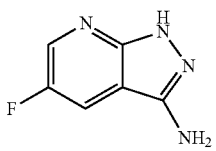 [SMILES: Nc1n[nH]c2ncc(F)cc12]

A suspension of 38.5 g (245.93 mmol) of 2-chloro-5-fluoronicotinonitrile was introduced in 1,2-ethanediol (380 ml) and subsequently admixed with hydrazine hydrate (119.6 ml, 2.459 mol). The mixture was heated at reflux with stirring for 4 h. On cooling, the product precipitated. The yellow crystals were admixed with water (380 ml) and subjected to extractive stirring at RT for 10 min. Then the suspension was filtered with suction over a frit, and the filter product was washed with water (200 ml) and with −10° C. cold THF (200 ml). The residue was dried under a high vacuum over phosphorus pentoxide.

Yield: 22.8 g (61% of theory)

$^1$H NMR (400 MHz, DMSO-$d_6$): δ=5.54 (s, 2H), 7.96 (dd, 1H), 8.38 (m, 1H), 12.07 (m, 1H).

reduced pressure. The resulting crystals were admixed with dichloromethane (388 ml) and extractively stirred for 20 min. Filtration with suction was carried out again, and the filter product was washed with diethyl ether and sucked dry.

Yield: 20.2 g (53% of theory)

$^1$H NMR (400 MHz, DMSO-$d_6$): δ=7.87 (br s, 1H), 7.99 (dd, 1H), 8.10 (br s, 1H), 8.52 (d, 1H).

Example 5A

5-Fluoro-3-iodo-1H-pyrazolo[3,4-b]pyridine

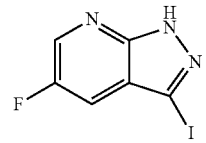 [SMILES: Fc1cnc2[nH]nc(I)c2c1]

In THF (329 ml), 10 g (65.75 mmol) of 5-fluoro-1H-pyrazolo[3,4-b]pyridin-3-amine were introduced and cooled to 0° C. Then 16.65 ml (131.46 mmol) of boron trifluoride diethyl ether complex were slowly added. The reaction mixture was cooled further to −10° C. Then a solution of 10.01 g (85.45 mmol) of isopentyl nitrite in THF (24.39 ml) was added slowly, followed by stirring for a further 30 min. The mixture was diluted with cold diethyl ether (329 ml) and the resulting solid was isolated by filtration. The diazonium salt thus prepared was added in portions to a 0° C. cold solution of 12.81 g (85.45 mmol) of sodium iodide in acetone (329 ml), and the mixture was stirred at RT for 30 min. The reaction mixture was poured into ice-water (1.8 l) and extracted twice with ethyl acetate (487 ml each time). The collected organic phases were washed with saturated aqueous sodium chloride solution (244 ml), dried, filtered and concentrated. This gave 12.1 g (86% purity, 60% of th.) of the desired compound in the form of a brown solid. The crude product was reacted without further purification.

LC-MS (Method 1): $R_t$=1.68 min; MS (ESIpos): m/z=264 (M+H)$^+$

Example 6A

5-Fluoro-1-(2-fluorobenzyl)-3-iodo-1H-pyrazolo[3,4-b]pyridine

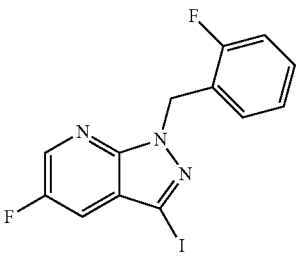 [SMILES: Fc1cnc2c(c1)c(I)nn2Cc1ccccc1F]

In DMF (2538 ml), 141 g (462.11 mmol) of the compound from Example 5A were introduced and then 96.09 g (508.32 mmol) of 2-fluorobenzyl bromide and 165.62 g (508.32 mmol) of cesium carbonate were added. The mixture was stirred at RT for two hours. The reaction mixture was then poured into saturated aqueous sodium chloride solution (13 670 ml) and extracted twice with ethyl acetate (5858 ml) The collected organic phases were washed with saturated aqueous sodium chloride solution (3905 ml), dried, filtered and concentrated. The residue was chromatographed on silica gel (eluent: petroleum ether/ethyl acetate 97:3) and the product fractions were concentrated. The resulting solid was dissolved in dichloromethane and washed once with saturated aqueous sodium thiosulphate solution (500 ml) and then with saturated aqueous sodium chloride solution (500 ml). The product was concentrated to dryness and the residue was suspended with diethyl ether, isolated by filtration with suction and dried under a high vacuum. This gave 106.6 g (62% of theory) of the desired compound.

LC-MS (Method 1): $R_t$=2.57 min

MS (ESIpos): m/z=372 (M+H)$^+$ $^1$H NMR (400 MHz, DMSO-d$_6$): δ=5.73 (s, 2H), 7.13-7.26 (m, 3H), 7.33-7.41 (m, 1H), 7.94 (dd, 1H), 8.69-8.73 (m, 1H).

Example 7A

2-[5-Fluoro-1-(2-fluorobenzyl)-1H-pyrazolo[3,4-b]pyridin-3-yl]-5-nitropyrimidine-4,6-diamine

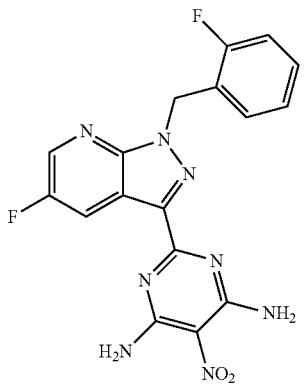 [SMILES: Nc1nc(-c2nn(Cc3ccccc3F)c3ncc(F)cc23)nc(N)c1[N+](=O)[O-]]

In 1,4-dioxane (86 ml), 860 mg (2.32 mmol) of the compound from Example 6A were introduced under argon and the reaction mixture was flushed with argon for 10 min. Then 3.51 ml (6.95 mmol) of hexabutylditin and 483 mg (2.55 mmol) of 2-chloro-5-nitropyrimidine-4,6-diamine (prepared by the method of *Helvetica Chimica Acta* (1951), 34, 835-40) were added. Subsequently 860 mg (0.744 mmol) of tetrakis(triphenylphosphine)palladium(0) were added and the reaction mixture was heated at reflux overnight. It was then cooled to RT, admixed with water and extracted twice with ethyl acetate. The collected organic phases were dried over sodium sulphate, filtered and concentrated. The residue was subjected to extractive stirring in ethyl acetate, and the solid was isolated by filtration and dried under a high vacuum. This gave 355 mg (62% purity, 24% of th.) of the desired compound. The crude product was reacted without further purification.

LC-MS (Method 2): $R_t$=1.03 min

MS (ESIpos): m/z=399 (M+H)$^+$

Example 8A

5-Fluoro-1-(2-fluorobenzyl)-1H-pyrazolo[3,4-b]pyridine-3-carbonitrile

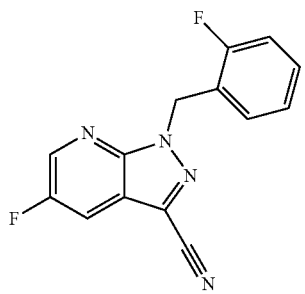 [SMILES: N#Cc1nn(Cc2ccccc2F)c2ncc(F)cc12]

A suspension of 16.03 g (43.19 mmol) of 5-fluoro-1-(2-fluorobenzyl)-3-iodo-1H-pyrazolo[3,4-b]pyridine (Example 6A) and 4.25 g (47.51 mmol) of copper cyanide were introduced in DMSO (120 ml) and stirred at 150° C. for 2 h. After cooling, the contents of the flask were cooled to about 40° C., poured into a solution of conc. aqueous ammonia (90 ml) and water (500 ml), admixed with ethyl acetate (200 ml) and subjected to brief extractive stirring. The aqueous phase was separated off and extracted twice more with ethyl acetate (200 ml each time). The combined organic phases were washed twice with 10% strength aqueous sodium chloride solution (100 ml each time), dried and concentrated under reduced pressure. The crude product was reacted without further purification.

Yield: 11.1 g (91% of theory)

$^1$H NMR (400 MHz, DMSO-d$_6$): δ=5.87 (s, 2H), 7.17-7.42 (m, 4H), 8.52 (dd, 1H), 8.87 (dd, 1H).

Example 9A

5-Fluoro-1-(2-fluorobenzyl)-1H-pyrazolo[3,4-b]pyridine-3-carboximidamide acetate

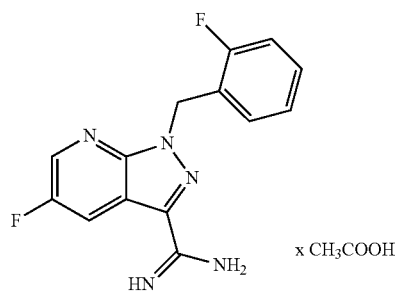 [SMILES: N=C(N)c1nn(Cc2ccccc2F)c2ncc(F)cc12]

To 2.22 g (41.07 mmol) of sodium methoxide in methanol (270 ml) were added 11.1 g (41.07 mmol) of 5-fluoro-1-(2-fluorobenzyl)-1H-pyrazolo[3,4-b]pyridine-3-carbonitrile (Example 8A) and the mixture was stirred at RT for 2 h. Then 2.64 g (49.29 mmol) of ammonium chloride and acetic acid (9.17 ml) were added and the mixture was heated at reflux overnight. It was then concentrated to dryness and the residue was taken up in water (100 ml) and ethyl acetate (100 ml) and adjusted to a pH of 10 using 2N aqueous sodium hydroxide solution. It was stirred intensively at RT for about 1 h. The resulting suspension was filtered with suction and the filter product was washed with ethyl acetate (100 ml), with water (100 ml) und again with ethyl acetate (100 ml). The residue was dried under a high vacuum over phosphorus pentoxide.

Yield: 9.6 g (78% of th.)

MS (ESIpos): m/z=288 (M+H)$^+$ $^1$H NMR (400 MHz, DMSO-d$_6$): δ=1.85 (s, 3H), 5.80 (s, 2H), 7.14-7.25 (m, 3H), 7.36 (m, 1H), 8.42 (dd, 1H), 8.72 (dd, 1H).

Example 10A

2-[5-Fluoro-1-(2-fluorobenzyl)-1H-pyrazolo[3,4-b]pyridin-3-yl]-5-[(E)-phenyldiazenyl]pyrimidine-4,6-diamine

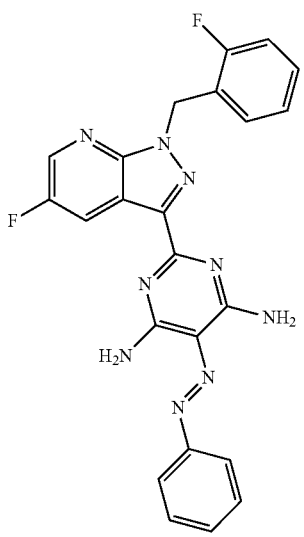 [SMILES: Nc1nc(-c2nn(Cc3ccccc3F)c3ncc(F)cc23)nc(N)c1/N=N/c1ccccc1]

Water (40 ml) and concentrated hydrochloric acid (7.07 ml) were admixed with stirring with 3.85 g (41.34 mmol) of aniline and this mixture was cooled to 0° C. Then a solution of 2.85 g (41.34 mmol) of sodium nitrite in water (21 ml) was added dropwise at between 0° C. and 5° C., followed by stirring at 0° C. for 15 min. Thereafter, at 0° C., a solution of 4.28 g (52.25 mmol) of sodium acetate in water (19 ml) was added rapidly dropwise, and then, with thorough stirring, a solution of 2.73 g (41.34 mmol) of malononitrile in ethanol (10 ml) was added dropwise. After 2 h at 0° C., the resulting precipitate was isolated by filtration with suction and washed three times with water (50 ml each time) and with petroleum ether (50 ml). The residue, still moist, was dissolved in DMF (46 ml) and added dropwise at precisely 85° C. to a solution of 9.5 g (33.07 mmol) of 5-fluoro-1-(2-fluorobenzyl)-1H-pyrazolo[3,4-b]pyridin-3-carboximidamide acetate (Example 9A) in DMF (46 ml) and triethylamine (5.76 ml). The mixture was then stirred at 100° C. for 4 h and left to cool to RT overnight. The mixture was poured into water (480 ml) and subjected to extractive stirring at RT for 1 h. After the precipitate had been isolated by filtration with suction, it was washed twice with water (100 ml each time) and twice with methanol (50 ml each time) and then dried under a high vacuum.

Yield: 9.6 g (59% of theory)

LC-MS (Method 2): R$_t$=1.21 min

MS (ESIpos): m/z=458 (M+H)$^+$

Example 11A

2-[5-Fluoro-1-(2-fluorobenzyl)-1H-pyrazolo[3,4-b]pyridin-3-yl]pyrimidine-4,5,6-triamine

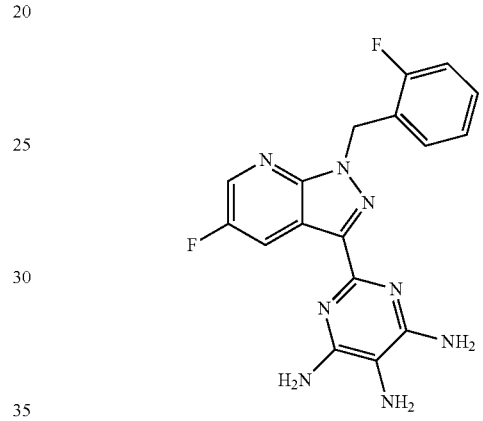

Variant A: Preparation starting from Example 7A:

In pyridine (30 ml), 378 mg (0.949 mmol) of the compound from Example 7A were introduced and then 143 mg (0.135 mmol) of palladium (10% on carbon) were added. The mixture was hydrogenated overnight at RT under standard hydrogen pressure. The suspension was then filtered through kieselguhr and the filtercake was washed with ethanol. The filtrate was concentrated and yielded 233 mg (81% purity, 51% of theory) of the desired compound, which was reacted without further purification.

Variant B: Preparation starting from Example 10A:

In DMF (800 ml), 39.23 g (85.75 mmol) of the compound from Example 10A were introduced and then 4 g of palladium (10% on carbon) were added. The mixture was hydrogenated with stirring overnight under standard hydrogen pressure. The batch was filtered over kieselguhr and the filter product was washed with a little DMF and then with a little methanol, and concentrated to dryness. The residue was admixed with ethyl acetate and stirred vigorously, and the precipitate was filtered off with suction, washed with ethyl acetate and diisopropyl ether and dried under a high vacuum over Sicapent.

Yield: 31.7 g (100% of theory)

LC-MS (Method 2): R$_t$+=0.81 min

MS (ESIpos): m/z=369 (M+H)$^+$

Working Examples

Example 1

Methyl {4,6-diamino-2-[5-fluoro-1-(2-fluorobenzyl)-1H-pyrazolo[3,4-b]pyridin-3-yl]pyrimidin-5-yl}carbamate

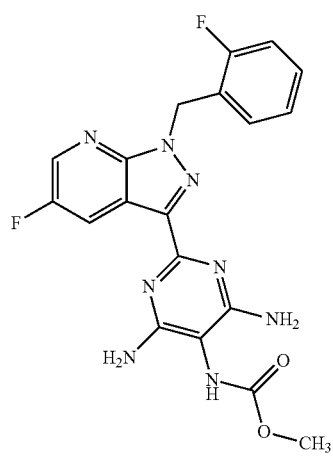 [SMILES: COC(=O)Nc1c(N)nc(-c2nn(Cc3ccccc3F)c3ncc(F)cc23)nc1N]

In pyridine (600 ml), 31.75 g (86.20 mmol) of the compound from Example 11A were introduced under argon and cooled to 0° C. Then a solution of 6.66 ml (86.20 mmol) of methyl chloroformate in dichloromethane (10 ml) was added dropwise and the mixture was stirred at 0° C. for 1 h. Thereafter the reaction mixture was brought to RT, concentrated under reduced pressure and co-distilled repeatedly with toluene. The residue was stirred with water/ethanol and then filtered off on a frit, after which it was washed with ethanol and ethyl acetate. Subsequently the residue was again stirred with diethyl ether, isolated by filtration with suction and then dried under a high vacuum.

Yield: 24.24 g (65% of theory)

LC-MS (Method 2): $R_t$=0.79 min

MS (ESIpos): m/z=427 (M+H)+

$^1$H NMR (400 MHz, DMSO-$d_6$): δ=3.62 (br. s, 3H), 5.79 (s, 2H), 6.22 (br. s, 4H), 7.10-7.19 (m, 2H), 7.19-7.26 (m, 1H), 7.32-7.40 (m, 1H), 7.67 (br. s, 0.2H), 7.99 (br. s, 0.8H), 8.66 (m, 1H), 8.89 (d, 1H).

Example 2

Methyl {4,6-diamino-2-[5-fluoro-1-(2-fluorobenzyl)-1H-pyrazolo[3,4-b]pyridin-3-yl]pyrimidin-5-yl}methylcarbamate

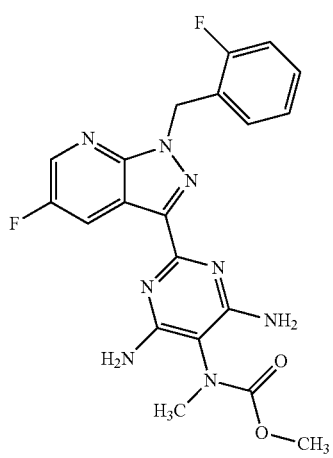 [SMILES: COC(=O)N(C)c1c(N)nc(-c2nn(Cc3ccccc3F)c3ncc(F)cc23)nc1N]

A quantity of 200 mg (0.469 mmol) of methyl {4,6-diamino-2-[5-fluoro-1-(2-fluorobenzyl)-1H-pyrazolo[3,4-b]pyridin-3-yl]pyrimidin-5-yl}carbamate (Example 1) was introduced in THF (5 ml) at 0° C. Then 0.704 ml (0.704 mmol) of lithium hexamethyldisilazane solution (1M in THF) was added and the mixture was stirred at this temperature for 20 min. Subsequently 43.8 µl (0.704 mmol) of iodomethane were added and the mixture was warmed to RT. After 1 h at this temperature, reaction was terminated with water (1 ml) and the reaction mixture was concentrated, the residue being separated by means of preparative RP-HPLC (water (+0.05% formic acid)-acetonitrile gradient).

Yield: 90 mg (44% of theory)

LC-MS (Method 2): $R_t$=0.85 min

MS (ESIpos): m/z=441 (M+H)$^+$ $^1$H NMR (400 MHz, DMSO-$d_6$): δ=3.00 (s, 3H), 3.53 (s, 2.2H), 3.66 (s, 0.8H), 5.81 (s, 2H), 6.57 (br. s, 4H), 7.13 (m, 2H), 7.22 (m, 1H), 7.35 (m, 1H), 8.67 (m, 1H), 8.87 (dd, 1H).

Example 3

Methyl {4,6-diamino-2-[5-fluoro-1-(2-fluorobenzyl)-1H-pyrazolo[3,4-b]pyridin-3-yl]pyrimidin-5-yl}(2,2,2-trifluoroethyl)carbamate

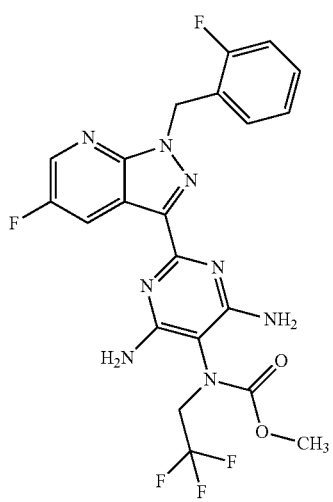 [SMILES: COC(=O)N(CC(F)(F)F)c1c(N)nc(-c2nn(Cc3ccccc3F)c3ncc(F)cc23)nc1N]

A quantity of 3.470 g (8.138 mmol) of the compound from Example 1 was suspended in 35 ml of THF, admixed at 0° C. with 358 mg (8.952 mmol) of sodium hydride (60% suspension in mineral oil) and stirred at 0° C. for 90 min, in the course of which a solution was formed. A quantity of 2.519 g (8.952 mmol) of 2,2,2-trifluoroethyl trichloromethanesulphonate was added and the mixture was stirred at RT for 48 h. It was then stirred with water and concentrated on a rotary evaporator. The residue was taken up in ethyl acetate, and the organic phase was washed twice with water and dried over sodium sulphate. This gave 5.005 g of the target compound (79% of th., purity by HPLC 65%). A quantity of 250 mg of the residue was purified by means of preparative HPLC (Eluent: methanol/water, gradient 30:70→90:10).

LC-MS (Method 2): $R_t$=0.97 min; MS (EIpos): m/z=509 [M+H]$^+$.

$^1$H NMR (400 MHz, DMSO-$d_6$): δ [ppm]=3.63 (s, 3H), 4.06-4.15 (m, 2H), 5.80 (s, 2H), 6.46 (s br, 4H) 7.11-7.15 (m, 2H), 7.20-7.25 (m, 1H), 7.33-7.38 (m, 1H), 8.66 (dd, 1H), 8.91 (dd, 1H).

Example A

Bleomycin-Induced Skin Fibrosis

Local skin fibrosis was induced in 6-week-old, pathogen-free, female DBA/2 mice (Charles River, Sulzfeld, Germany) by repeated (every other day) subcutaneous injections of bleomycin (0.5 mg/ml in saline) in a defined area of the upper back. Control mice were injected in the same manner with saline only and served as reference. For all groups the injection volume was 100 μl. Concomitant to bleomycin treatment, the mice were treated orally with test drug or vehicle. Mice were treated a) with vehicle b) with 1 mg/kg compound of formula 27, and c) with 3 mg/kg compound of formula 27, twice a day via gavage for 21 days. After this 3 weeks treatment period, the animals were sacrificed and skin samples were obtained for analysis.

Histological Analysis

The injected skin areas were fixed in 4% formalin and embedded in paraffin. Histological sections were stained with hematoxylin and eosin for the determination of dermal thickness. The dermal thickness was determined by measuring the largest distance between the epidermal-dermal junction and the dermal-subcutaneous fat junction. The measurements were performed by an examiner blinded to the treatment of the mice.

Hydroxyproline Assay

To analyze the collagen content in skin samples, hydroxyproline assay was performed. After digestion of punch biopsies (Ø 3 mm) in 6M HCl for three hours at 120° C., chloramine T (0.06 M) was added and samples were mixed and incubated for 20 min at room temperature. 3.15 M perchloric acid and 20% p-dimethylaminobenzaldehyde were added and samples were incubated for additional 20 min at 60° C. The absorbance was determined at 557 nm.

Immunohistochemistry for α-Smooth Muscle Actin

The expression of α-smooth muscle actin (αSMA) was analyzed in paraffin embedded sections. After deparaffinization, samples were incubated with 3% bovine serum albumin followed by incubation with 3% $H_2O_2$. αSMA positive cells in mouse sections were detected by incubation with monoclonal anti-αSMA antibodies (clone 1A4, Sigma-Aldrich, Steinheim, Germany). Irrelevant isotype antibodies in the same concentration were used for control (Santa Cruz Biotechnology, Santa Cruz, Calif., USA). Antibodies labeled with horseradish peroxidase (Dako, Hamburg, Germany) were used as secondary antibodies. The expression of the NICD and αSMA was visualized with DAB peroxidase substrate solution (Sigma-Aldrich). The number of myofibroblasts was counted from 4 different sections of lesional skin for each mouse by an examiner blinded to the treatment of the mice.

TABLE 1

Effects of the compound of formula 27 on development of Bleomycin-induced skin fibrosis.

|  | a) Bleomycin + vehicle | b) Bleomycin + 1 mg/kg compound of formula 27 | c) Bleomycin + 3 mg/kg compound of formula 27 |
| --- | --- | --- | --- |
| Dermal thickness | 1.70 | 1.37 | 1.19 |
| Collagen content | 1.31 | 1.19 | 1.11 |
| Myofibroblast count | 3.72 | 3.23 | 1.90 |

Fibrosis parameters expressed as x-fold change with respect to vehicle-treated control.

These dose dependent and significant effects were seen with other examples i.e. the compound of formula 3, the compound of formula 6 in a similar manner.

Fibrosis parameters expressed as x-fold change with respect to vehicle-treated control

TABLE 2

Effects of the compound of formula 3 and the compound of formula 6 on development of Bleomycin-induced skin fibrosis.
Fibrosis parameters expressed as x-fold change with respect to vehicle-treated control

|  | a) Bleomycin + vehicle | b) Bleomycin + 1.0 mg/kg compound of formula 3 | c) Bleomycin + 0.3 mg/kg compound of formula 6 | d) Bleomycin + 1 mg/kg compound of formula 6 | e) Bleomycin + 3 mg/kg compound of formula 6 |
|---|---|---|---|---|---|
| Dermal thickness | 1.71 | 1.38 | 1.41 | 1.24 | 1.19 |
| Collagen content | 1.56 | 1.38 | 1.41 | 1.28 | 1.20 |
| Myofibroblast count | 3.86 | 2.55 | 3.13 | 2.05 | 1.49 |

Example B

Bleomycin-Induced Skin Fibrosis

Local skin fibrosis was induced in 6-week-old, pathogen-free, female DBA/2 mice (Charles River, Sulzfeld, Germany) by repeated (every other day) subcutaneous injections of bleomycin (0.5 mg/ml in saline) in a defined area of the upper back. Control mice were injected in the same manner with saline only. For all groups the injection volume was 100 µl. The study comprises 4 arms with
a) mice receiving saline injection for 6 weeks (serving as reference)
b) mice receiving Bleomycin injection for 6 weeks
c) mice receiving Bleomycin injection for 6 weeks and additional treatment with the compound of formula 27 (3 mg/kg) twice a day via gavage for the last 3 weeks
d) mice receiving the first 3 weeks bleomycin injections and the second 3 weeks saline injection.

After 6 weeks the animals were sacrificed and skin samples were obtained for analysis.

Histological analysis, hydroxyproline assay and immuno-histochemistry for α-smooth muscle actin were performed as described in the Example 1 section.

TABLE 3

Effects of the compound of formula 27 (3 mg/kg p.o.) on established Bleomycin-induced skin fibrosis Fibrosis parameters expressed as x-fold change with respect to vehicle-treated control (group a)

|  | b) Bleomycin 6 weeks | c) Bleomycin 6 weeks + 3 weeks the compound of formula 27 | d) Bleomycin 3 weeks + 3 weeks NaCl |
|---|---|---|---|
| Dermal thickness | 1.57 | 1.26 | 1.40 |
| Myofibroblast count | 3.87 | 1.68 | 3.50 |

Example C

Tight Skin Mouse Model

In addition to the mouse model of bleomycin-induced dermal fibrosis, the tight-skin (Tsk-1) mouse model of systemic sclerosis was used to evaluate the anti-fibrotic potential of test drugs. Due to a dominant mutation in fibrillin-1, the phenotype of Tsk-1 is characterized by an increased hypodermal thickness. Genotyping of Tsk-1 mice was performed by PCR with the following primers: mutated fibrillin-1/Tsk-1 forward primer: 5'-GTTGGCAACTATAC-CTGCAT-3', reverse primer: 5'-CCTTTCCTGG-TAACATAGGA-3'. Tsk-1 mice were treated daily with test drug or vehicle, respectively, by oral gavage. In addition, a group of corresponding wild type(pa/pa) mice was treated with vehicle. The treatment was started at an age of five weeks. After five weeks of treatment, mice were sacrificed by cervical dislocation and skin samples were obtained for analysis.

Histological analysis, hydroxyproline assay and immuno-histochemistry for α-smooth muscle actin were performed as described in the Example 1 section.

TABLE 4

Effects of the compound of formula 27 on established skin fibrosis in Tsk-mice

|  | Tsk-1 + vehicle | Tsk-1 + 1 mg/kg the compound of formula 27 | Tsk-1 + 3 mg/kg the compound of formula 27 |
|---|---|---|---|
| hypodermal thickness | 5.03 | 3.46 | 2.88 |
| Collagen content | 2.46 | 1.61 | 1.67 |
| Myofibroblast count | 2.64 | 2.12 | 1.70 |

Fibrosis parameters expressed as x-fold change with respect to vehicle-treated wild type mice Example D The haemodynamic effects of i.e. example, the compound of formula 3, the compound of formula 4, the compound of formula 6 were analyzed in conscious mice. Telemetric implants (DSI®) were used. Signals were received with RMC1-DSI® receiver plates, compiled and analyzed with PONEMAH® physiology platform software.

The mice received either placebo (tylose), 0.3 mg/kg the compound of formula 27, 1 mg/kg the compound of formula 27, 3 mg/kg the compound of formula 27 (FIG. 1), 1.0 mg/kg the compound of formula 3, 3.0 mg/kg the compound of formula 3, 10.0 mg/kg the compound of formula 3 (FIG. 2A,2B), 1.0 mg/kg the compound of formula 4, 3.0 mg/kg the compound of formula 4, 10.0 mg/kg the compound of formula 4 (FIG. 3A/3B), 0.3 mg/kg the compound of formula 6, 1.0 mg/kg the compound of formula 6, 3.0 mg/kg, 10.0 mg/kg the compound of formula 6 (FIG. 4A/4B). The blood pressure and heart rate was monitored before and after application of placebo or the compounds. FIG. 1 shows effects of the compound of formula 27 on blood pressure (left) and heart rate (right), FIG. 2 shows the effect of the compound of formula 3 on blood pressure (FIG. 2A) and heart rate (FIG. 2B), FIG. 3 shows the effects of the compound of formula 4 on blood pressure (FIG. 3A) and heart rate (FIG. 3B), FIG. 4 shows the effect of the compound of formula 6 on blood pressure (FIG. 4A) and heart rate (FIG. 4B).

Example E

The effects of the compound of formula 27 and vardenafil as stand alone and in combination were analyzed in vitro in human dermal fibroblasts in vitro. The compound of formula 27, vardenafil and combinations thereof significantly blocked the TGFbeta-induced Collagen gene expression and Hydroxyproline (HP) deposition.

REFERENCES

Evgenov O V, Pacher P, Schmidt P M et al. (2006): NO-independent stimulators and activators of soluble guanylate cyclase: discovery and therapeutic potential. Nat. Rev. Drug. Discov. 5(9):755-68 symptoms associated with benign prostatic hyperplasia: a randomized, double-blind trial. J. Urol. 177: 1071-1077.

McVary K T, Roehrborn C G, Kaminetsky J C, Auerbach S M, Wachs B, Young J M, Esler A, Sides G D, Denes B S. (2007): Tadalafil relieves lower urinary tract symptoms secondary to benign prostatic hyperplasia. J Urol. 177: 1401-1407.

Ong V H and Denton C P (2010): Innovative therapies for systemic sclerosis Curr. Opin. Rheumatol. 22:264-272.

Porst H, Sandner P, Ulbrich E. (2008): Vardenafil in the treatment of lower urinary tract symptoms secondary to benign prostatic hyperplasia. Curr. Urol. Rep. 9:295-301.

Sandner P, Neuser D, Bischoff E (2009): Erectile dysfunction and lower urinary tract. Handb. Exp. Pharmacol. 191:507-531.

Spiera R, Gordon J, Mersten J, Magro C, Mehta M, Wildmann H, Kloiber S, Kirou K, Lyman S, Crow M (2011): Imatinib mesylate (Gleevec) in the treatment of diffuse cutaneous systemic sclerosis: results of a 1 year, phse IIa, single-arm open-label clinical trial. Ann. Rheum. Dis. Epub Mar. 11, 2011.

```
SEQUENCE LISTING

<160> NUMBER OF SEQ ID NOS: 2

<210> SEQ ID NO 1
<211> LENGTH: 20
<212> TYPE: DNA
<213> ORGANISM: artificial sequence
<220> FEATURE:
<223> OTHER INFORMATION: mutated fibrillin-1/Tsk-1 forward primer

<400> SEQUENCE: 1
gttggcaact atacctgcat                                               20

<210> SEQ ID NO 2
<211> LENGTH: 20
<212> TYPE: DNA
<213> ORGANISM: artificial sequence
<220> FEATURE:
<223> OTHER INFORMATION: mutated fibrillin-1/Tsk-1 reverse primer

<400> SEQUENCE: 2
cctttcctgg taacatagga                                               20
```

Ferrini M G, Kovanecz I, Nolazco G (2006): Effects of long-term vardenafil treatment on the development of fibrotic plaques in a rat model of Peyronie's disease. B. J. U. 97:625-633.

Harris E D, et al. (2005): Kelley's Textbook of Rhematology 7th edition. Elsevier Saunders, Philadelphia Pa.

Kaplan S A, Gonzalez R R (2007): Phosphodiesterase type 5 inhibitors for the treatment of male lower urinary tract symptoms. Rev. Urol. 9(2):73-77

Khanna D and Denton C P (2010) Evidence-based management of rapidly progressing systemic sclerosis. Best. Pract. Res. Clin. Rheumatol. 24:387-400

Knorr A, Hirth-Dietrich C, Alonso-Alija C. et al. (2008): Nitric oxide-independent activation of soluble guanylate cyclase by BAY 60-2770 in experimental liver fibrosis. Arzneimittelforschung 58:71-80.

MVary K K. T. McVary, W. Monnig, J. L. Camps, Jr., J. M. Young, L. J. Tseng and G. van den Ende (2007): Sildenafil citrate improves erectile function and ur inary symptoms in men with erectile dysfunction and lower urinary tract

The invention claimed is:

1. A method for reducing collagen production in dermal fibroblasts, reducing myofibroblast differentiation and/or for triggering redifferentiation of myofibroblast in a patient suffering from a fibrotic disease selected from the group consisting of systemic sclerosis (SSc), diffuse systemic sclerosis (dSSc), limited systemic sclerosis (lSSc), overlap type of systemic sclerosis, undifferentiated type of systemic sclerosis, systemic sclerosis sine scleroderma, skin fibrosis, nephrogenic fibrosing dermopathy (NFD), nephrogenic systemic fibrosis (NSF), systemic sclerosis (SSc) concomitant fibrosis of internal organs, and keloid formation, comprising administering an effective amount of a compound according to one of formulae (3), (6) or (27)

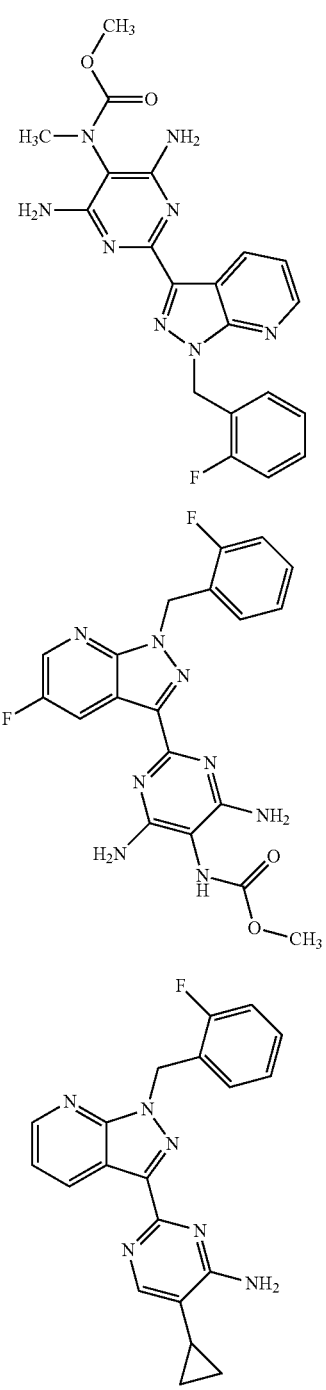

to the patient in need thereof; wherein reduction of collagen production in dermal fibroblasts, reduction of myofibroblast differentiation and/or triggering redifferentiation of myofibroblast occurs without vasodilation.

2. The method of claim 1, comprising administering the compound of one of formulae (3), (6) or (27) in combination with at least one PDE5 inhibitor selected from the group consisting of: tadalafil ((6R,12aR)-2,3,6,7,12,12a-hexahydro-2-methyl-6-(3,4-methylene-dioxyphenyl) pyrazino (1',2':1,6) pyrido(3,4-b)indole-1,4-dione), vardenafil (2-(2-ethoxy-5-(4-ethylpiperazin-1-yl-1-sulfonyl)phenyl)-5-methyl-7-propyl-3H-imidazo (5,1-f) (1,2,4)triazin-4-one), sildenafil (3-[2-ethoxy-5-(4-methylpiperazin-1-yl)sulfonylphenyl]-7-methyl-9-propyl-2,4,7,8-tetrazabicyclo [4.3.0] nona-3,8,10-trien-5-one), udenafil (5-[2-propyloxy-5-(1-methyl-2-pyrrolidinylethylamidosulfonyl)phenyl]-methyl-3-propyl-1,6-dihydro-7H-pyrazolo(4,3-d)pyrimidine-7-one), dasantafil (7-(3-bromo-4-methoxybenzyl)-1-ethyl-8-[[(1,2)-2-hydroxycyclopentyl]amino]-3-(2-hydroxyethyl)-3, 7-dihydro-1-purine-2,6-dione), avanafil (4-{[(3-chloro-4-methoxyphenyl)methyl]amino}-2-[(2S)-2-(hydroxymethyl) pyrrolidin-1-yl]-N-(pyrimidin-2-ylmethyl)pyrimidine-5-carboxamide), mirodenafil, lodenafil, LAS 34179 (triazolo [1,2-]xanthine,6-methyl-4-propyl-2-[2-propoxy-5-(4-methylpiperazino)sulfonyl]phenyl) or a salt, hydrate or hydrate of a salt thereof.

3. The method of claim 2, wherein the PDE5 inhibitor is sildenafil or vardenafil.

4. The method of claim 1, wherein the fibrotic disease is systemic sclerosis (SSc) concomitant fibrosis of internal organs.

5. The method of claim 1, wherein the fibrotic disease is diffuse systemic sclerosis (dSSc).

6. A method for reducing collagen production in dermal fibroblasts, reducing myofibroblast differentiation and for triggering redifferentiation of myofibroblast in a patient suffering from a fibrotic disease selected from the group consisting of systemic sclerosis (SSc), diffuse systemic sclerosis (dSSc), limited systemic sclerosis (lSSc), overlap type of systemic sclerosis, undifferentiated type of systemic sclerosis, systemic sclerosis sine scleroderma, skin fibrosis, nephrogenic fibrosing dermopathy (NFD), nephrogenic systemic fibrosis (NSF), keloid formation, and systemic sclerosis (SSc) concomitant fibrosis of internal organs, comprising administering an effective amount of a compound having the formula (3)

to the patient in need thereof; wherein reduction of collagen production in dermal fibroblasts, reduction of myofibroblast differentiation and/or triggering redifferentiation of myofibroblast occurs without vasodilation.

7. The method of claim 6, wherein the fibrotic disease is systemic sclerosis (SSc) concomitant fibrosis of internal organs.

* * * * *